United States Patent
Azuma et al.

(10) Patent No.: US 10,901,197 B2
(45) Date of Patent: Jan. 26, 2021

(54) MEDICAL OBSERVATION DEVICE AND LENS BARREL OF MEDICAL OBSERVATION DEVICE

(71) Applicant: SONY CORPORATION, Tokyo (JP)

(72) Inventors: Ryuhei Azuma, Kanagawa (JP); Hiroshi Mashima, Tokyo (JP); Takashi Kato, Kanagawa (JP); Takashi Terai, Kanagawa (JP); Shintaro Miyatani, Tokyo (JP); Daisuke Ikeda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 440 days.

(21) Appl. No.: 15/510,483

(22) PCT Filed: Jul. 29, 2015

(86) PCT No.: PCT/JP2015/071541
§ 371 (c)(1),
(2) Date: Mar. 10, 2017

(87) PCT Pub. No.: WO2016/042922
PCT Pub. Date: Mar. 24, 2016

(65) Prior Publication Data
US 2017/0285321 A1    Oct. 5, 2017

(30) Foreign Application Priority Data
Sep. 19, 2014    (JP) .................. 2014-191598

(51) Int. Cl.
*G02B 23/12*    (2006.01)
*G03B 11/00*    (2006.01)
(Continued)

(52) U.S. Cl.
CPC .............. *G02B 23/12* (2013.01); *A61B 90/20* (2016.02); *A61B 90/361* (2016.02); *G02B 7/006* (2013.01);
(Continued)

(58) Field of Classification Search
CPC ...... G02B 23/12; G02B 26/008; G02B 21/22; G02B 21/0012; G02B 7/021; G02B 7/006;
(Continued)

(56) References Cited

U.S. PATENT DOCUMENTS 4,713,683 A * 12/1987 Fujimori .............. A61B 1/0638
348/269
6,452,732 B1 * 9/2002 Okada .................. G02B 26/007
351/107
(Continued)

FOREIGN PATENT DOCUMENTS

AU    7796401 A    2/2002
CN    1451230 A    10/2003
(Continued)

OTHER PUBLICATIONS

International Search Report and Written Opinion of PCT Application No. PCT/JP2015/071541, dated Nov. 2, 2015, 09 pages of English Translation and 08 pages of ISRWO.
(Continued)

*Primary Examiner* — Joseph G Ustaris
*Assistant Examiner* — Jill D Sechser
(74) *Attorney, Agent, or Firm* — Chip Law Group

(57) ABSTRACT

The present disclosure provides a medical observation device to achieve improvement in functionality resulting from switching of optical elements and miniaturization of the device. The medical observation device includes: an imaging optical system configured to capture an image of a subject; an image sensor configured to photoelectrically convert the image of the subject captured by the imaging optical system; and an element holding frame configured to hold a plurality of optical elements and to be capable of being rotated around a rotation shaft. An axial direction of
(Continued)

the rotation shaft is set to a direction orthogonal to an optical axis direction that is a direction of a line from the imaging optical system to the image sensor, and the element holding frame is rotated and thus at least one of the optical elements among the plurality of optical elements is positioned on an optical axis.

13 Claims, 49 Drawing Sheets

(51) Int. Cl.
| | | |
|---|---|---|
| G03B 15/14 | (2006.01) | |
| G03B 5/00 | (2006.01) | |
| G02B 21/00 | (2006.01) | |
| G03B 35/08 | (2006.01) | |
| G02B 21/22 | (2006.01) | |
| G02B 26/00 | (2006.01) | |
| A61B 90/20 | (2016.01) | |
| A61B 90/00 | (2016.01) | |
| G02B 7/00 | (2006.01) | |
| G02B 7/02 | (2006.01) | |
| H04N 5/225 | (2006.01) | |
| G03B 7/18 | (2006.01) | |
| A61B 90/25 | (2016.01) | |

(52) U.S. Cl.
CPC ......... *G02B 7/021* (2013.01); *G02B 21/0012* (2013.01); *G02B 21/22* (2013.01); *G02B 26/008* (2013.01); *G03B 5/00* (2013.01); *G03B 11/00* (2013.01); *G03B 15/14* (2013.01); *G03B 35/08* (2013.01); *H04N 5/2254* (2013.01); *A61B 90/25* (2016.02); *A61B 2090/371* (2016.02); *G03B 7/18* (2013.01)

(58) Field of Classification Search
CPC ......... G03B 35/08; G03B 15/14; G03B 5/00; G03B 11/00; G03B 7/18; A61B 90/361; A61B 90/20; A61B 90/25; A61B 2090/371; H04N 5/2254
See application file for complete search history.

(56) References Cited

U.S. PATENT DOCUMENTS

| | | | |
|---|---|---|---|
| 8,827,578 B2 | 9/2014 | Jikihara et al. | |
| 2001/0028498 A1* | 10/2001 | Haga | G02B 23/12 359/407 |
| 2004/0056966 A1 | 3/2004 | Schechner et al. | |
| 2004/0075739 A1 | 4/2004 | Wada | |
| 2007/0273364 A1* | 11/2007 | Takei | G02B 7/102 324/207.2 |
| 2008/0204908 A1* | 8/2008 | Blanding | G02B 7/003 359/823 |
| 2010/0027004 A1* | 2/2010 | Bonyuet | G01J 3/0235 356/326 |
| 2012/0008194 A1* | 1/2012 | Mizuta | G02B 21/025 359/377 |
| 2013/0038782 A1* | 2/2013 | Fish | H04N 5/2254 348/360 |
| 2013/0242390 A1* | 9/2013 | Nomura | G02B 27/281 359/483.01 |
| 2014/0333767 A1 | 11/2014 | Jikihara et al. | |

FOREIGN PATENT DOCUMENTS

| | | |
|---|---|---|
| CN | 1496135 A | 5/2004 |
| CN | 203587934 U | 5/2014 |
| CN | 203851197 U | 9/2014 |
| EP | 1397005 A2 | 3/2004 |
| EP | 2629148 A | 8/2013 |
| JP | 2004-505512 A | 2/2004 |
| JP | 2004-104242 A | 4/2004 |
| JP | 2012-103452 A | 5/2012 |
| KR | 10-2003-0028553 A | 4/2003 |
| RU | 139756 U1 | 4/2014 |
| WO | 2002/009424 A2 | 1/2002 |
| WO | 2012/063482 A1 | 5/2012 |

OTHER PUBLICATIONS

International Preliminary Report on Patentability of PCT Application No. PCT/JP2015/071541, dated Mar. 30, 2017, 10 pages of English Translation and 05 pages of IPRP.

* cited by examiner

MEDICAL OBSERVATION DEVICE AND LENS BARREL OF MEDICAL OBSERVATION DEVICE

CROSS REFERENCE TO RELATED APPLICATIONS

This application is a U.S. National Phase of International Patent Application No. PCT/JP2015/071541 filed on Jul. 29, 2015, which claims priority benefit of Japanese Patent Application No. JP 2014-191598 filed in the Japan Patent Office on Sep. 19, 2014. Each of the above-referenced applications is hereby incorporated herein by reference in its entirety.

TECHNICAL FIELD

The present technology relates to the technical field of a medical observation device and a lens barrel of the medical observation device in which optical elements positioned on an optical axis can be switched.

CITATION LIST

Patent Literature

Patent Literature 1: JP 2006-80984A

Patent Literature 2: JP 2006-74654A

BACKGROUND ART

There are medical observation devices for observing lesions of patients in medical procedures and thus achieving efficiency in medical procedures, for example, surgical operations, treatments, inspections carried out in medical institutes such as hospitals. Such a medical observation device is mounted at, for example, a leading end of a robot arm, or the like, and is used to enable a lesion of a patient to be observed in a desired direction by operating the arm to set a necessary orientation or angle, and an image or video that it captures is projected on a display unit such as a monitor or a display.

There are cases in medical procedures in which observation forms according to diseases of patients are necessary. For example, there are an observation form in a state in which infrared light is removed, an observation form in which fluorescence emitted by various test drugs that have been administered is observed, and the like. In addition, there is also an observation form in which, for example, brightness of an image, an imaging range, or the like when an image of a lesion is captured is changed.

Thus, it is desirable for a medical observation device to include a switch mechanism which switches various optical elements such as an optical filter, a lens, and a polarizing element, and to have a function of performing imaging in a necessary observation form considering differences in observation forms.

As such a switch mechanism of optical elements, for example, there is one which has a filter frame in which three optical filters of different kinds are arranged and mounted in the direction orthogonal to the optical axis direction, and of which the filter frame slides in the direction orthogonal to the optical axis direction enabling the optical filters to be switched (for example, refer to Patent Literature 1 and 2).

DISCLOSURE OF INVENTION

Technical Problem

However, medical observation devices are used in surgical operations and medical procedures for treatment, examination, and the like, and observers like doctors and examiners visually recognize states of lesions through images and videos captured with the medical observation devices and displayed on display units, and also with their eyes.

Thus, there is concern that a medical observation device may obstruct visual recognition when a doctor or the like views a lesion with his or her eyes depending on the size of the medical observation device. In addition, since doctors and the like perform treatment on lesions using medical instruments like a surgical knife during surgical operations and the like, there is also concern that installation of a medical observation device would obstruct a surgical operation if the size of the medical observation device is large.

If the size of a medical observation device that is very useful in medical procedures is large in medical practice, there is concern of causing obstructions of the medical practice, and thus miniaturization of medical observation devices is desirable; however, if the switch mechanisms described in Patent Literatures 1 and 2 are used in medical observation devices, a large movement space in the direction orthogonal to the optical axis direction is necessary for the filter frame, resulting in an increased size of the medical observation device, which causes the inconvenience of hindering miniaturization.

Therefore, a medical observation device and a lens barrel of the medical observation device according to the present technology aim to overcome the above-described problems and to achieve improvement in functionality resulting from switching of optical elements and miniaturization of the device.

Solution to Problem

First, according to the present technology, the medical observation device includes: an imaging optical system configured to capture an image of a subject; an image sensor configured to photoelectrically convert the image of the subject captured by the imaging optical system; and an element holding frame configured to hold a plurality of optical elements and to be capable of being rotated around a rotation shaft. An axial direction of the rotation shaft is set to a direction orthogonal to an optical axis direction that is a direction of a line from the imaging optical system to the image sensor, and the element holding frame is rotated and thus at least one of the optical elements among the plurality of optical elements is positioned on an optical axis.

Accordingly, the element holding frame is rotated around the rotation shaft whose axial direction is set to the direction orthogonal to the optical axis direction, and thus at least one of the optical elements among the plurality of optical elements is positioned on the optical axis.

Second, in the lens barrel, it is desirable that when one of the optical elements is positioned on the optical axis, at least one of the other optical elements be in parallel with the optical axis.

Accordingly, the optical element in the parallel state does not protrude in the direction orthogonal to the optical axis.

Third, in the lens barrel, it is desirable that: three or more of the optical elements be provided; and one of the optical elements and at least one of the other optical elements be disposed to be perpendicular to each other.

Accordingly, the distance between the optical elements disposed in the perpendicular state in the direction orthogonal to the optical axis becomes shorter.

Fourth, in the lens barrel, it is desirable that the optical elements be optical filters each having different selectivity of wavelengths that pass through.

Accordingly, different types of images are acquired according to subjects.

Fifth, in the lens barrel, it is desirable that: a position detection sensor configured to detect a rotation position of the element holding frame be provided; and image processing according to the optical element positioned on the optical axis be performed based on a detection result of the position detection sensor.

Accordingly, image processing according to the optical elements positioned on the optical axis is performed.

Sixth, in the lens barrel, it is desirable that: a support housing in which the element holding frame is supported to be freely rotatable be provided; a stopper-receiving part be provided in the element holding frame; and a stopper part of the support housing is configured to hold the element holding frame at a rotation end in contacting with the stopper-receiving part.

Accordingly, the element holding frame is held at the rotation end as the stopper-receiving parts provided in the element holding frame are brought into contact with the stopper parts provided in the support housing.

Seventh, in the lens barrel, it is desirable that an urging spring configured to press the stopper-receiving part toward the stopper part be provided.

Accordingly, the element holding frame is held at the rotation end as the urging force of the urging spring presses the stopper-receiving parts toward the stopper parts.

Eighth, in the lens barrel, it is desirable that: a first stopper part configured to hold the element holding frame at one rotation end and a second stopper part configured to hold the element holding frame at the other rotation end be provided as the stopper part; a first stopper-receiving part brought into contact with the first stopper part and a second stopper-receiving part brought into contact with the second stopper part be provided as the stopper-receiving part; and the urging spring press the first stopper-receiving part toward the first stopper part at the one rotation end and press the second stopper-receiving part toward the second stopper part at the other rotation end.

Accordingly, the element holding frame is held at the one rotation end as the urging force of the urging spring presses the first stopper-receiving part toward the first stopper part, and the element holding frame is held at the other rotation end as the urging force of the urging spring presses the second stopper-receiving part toward the second stopper part.

Ninth, in the lens barrel, it is desirable that: a manipulation lever configured to be manipulated to cause the element holding frame to rotate be provided; and an urging force of the urging spring be applied to the element holding frame via the manipulation lever.

Accordingly, the manipulation lever functions as a power transmission means that applies a rotation force to the element holding frame and as an urging force transmission means that applies an urging force to the element holding frame.

Tenth, in the lens barrel, it is desirable that: a support housing in which the element holding frame is supported to be freely rotatable be provided; two fixed lens groups be mounted in the support housing separately from each other in the optical axis direction; and the element holding frame be positioned between the two fixed lens groups.

Accordingly, the element holding frame and the optical elements held in the element holding frame are shielded by each part in which fixed lens groups are mounted in the optical axis direction.

11th, in the lens barrel, it is desirable that a support housing formed in a box shape in which the element holding frame is supported to be freely rotatable be provided; and the element holding frame be positioned inside the support housing.

Accordingly, the element holding frame and the optical elements held in the element holding frame are tightly sealed by the support housing.

12th, in the lens barrel, it is desirable that: the imaging optical system be provided as a binocular optical system; and the optical elements be positioned across the two optical axes of the binocular optical system.

Accordingly, light passing through two light paths passes through the same optical element.

13th, in the lens barrel, it is desirable that the imaging optical system be provided as a binocular optical system; and a light shielding wall be provided between two optical axes in the optical holding frame.

Accordingly, the light shielding wall regulates incidence of light passing through the one light path on the other light path, and regulates incidence of light passing through the other light path on the one light path.

According to the present technology, the lens barrel of a medical observation device includes: an imaging optical system configured to capture an image of a subject; an image sensor configured to photoelectrically convert the image of the subject captured by the imaging optical system; and an element holding frame configured to hold a plurality of optical elements and to be capable of being rotated around a rotation shaft An axial direction of the rotation shaft is set to a direction orthogonal to an optical axis direction that is a direction of a line from the imaging optical system to the image sensor, and the element holding frame is rotated and thus at least one of the optical elements among the plurality of optical elements is positioned on an optical axis.

Accordingly, the element holding frame is rotated around the rotation shaft whose axial direction is set to the direction orthogonal to the optical axis direction, and thus at least one optical element among the plurality of optical elements is positioned on the optical axis.

Advantageous Effects of Invention

According to the present technology, the element holding frame is rotated around a rotation shaft whose axial direction is set to the direction orthogonal to the optical axis direction and thus at least one of the plurality of optical elements is positioned on the optical axis, and therefore it is possible to achieve improvement in functionality resulting from switching of the optical elements and miniaturization of the device.

Note that effects described in the present specification are merely examples, and are not limitative, and other effects can be exhibited.

BRIEF DESCRIPTION OF DRAWINGS

FIG. 9 is a schematic front diagram illustrating a positional relation between an iris unit, a second zoom lens holding frame, a driving cam, and the like.

FIG. 25 is an enlarged bottom diagram illustrating an operating body, a detection switch, and the like.

MODE(S) FOR CARRYING OUT THE INVENTION

An embodiment for implementing the present technology will be described below with reference to the accompanying drawings.

A medical observation device according to the embodiment to be described below is an imaging device that can photograph dynamic images and still images, and is formed in a shape stretching in one direction, having an optical axis direction in the longitudinal direction.

Description will be provided below on the premise that the optical axis direction is the front-rear direction and predetermined respective directions orthogonal to the optical axis are the up-down direction and the left-right direction. In addition, description will be provided by setting a subject side as front and a direction in which an image of a subject is taken as rear.

Note that the front, rear, up, down, left, and right directions to be described below are for the sake of convenience in description, and an embodiment of the present technology is not limited to these directions.

Furthermore, a lens group to be described below is constituted of a single lens or a plurality of lenses, and may include the single lens or plurality of lenses and other optical elements such as a diaphragm or an iris.

[Schematic Configuration of Medical System]

Figure 1:
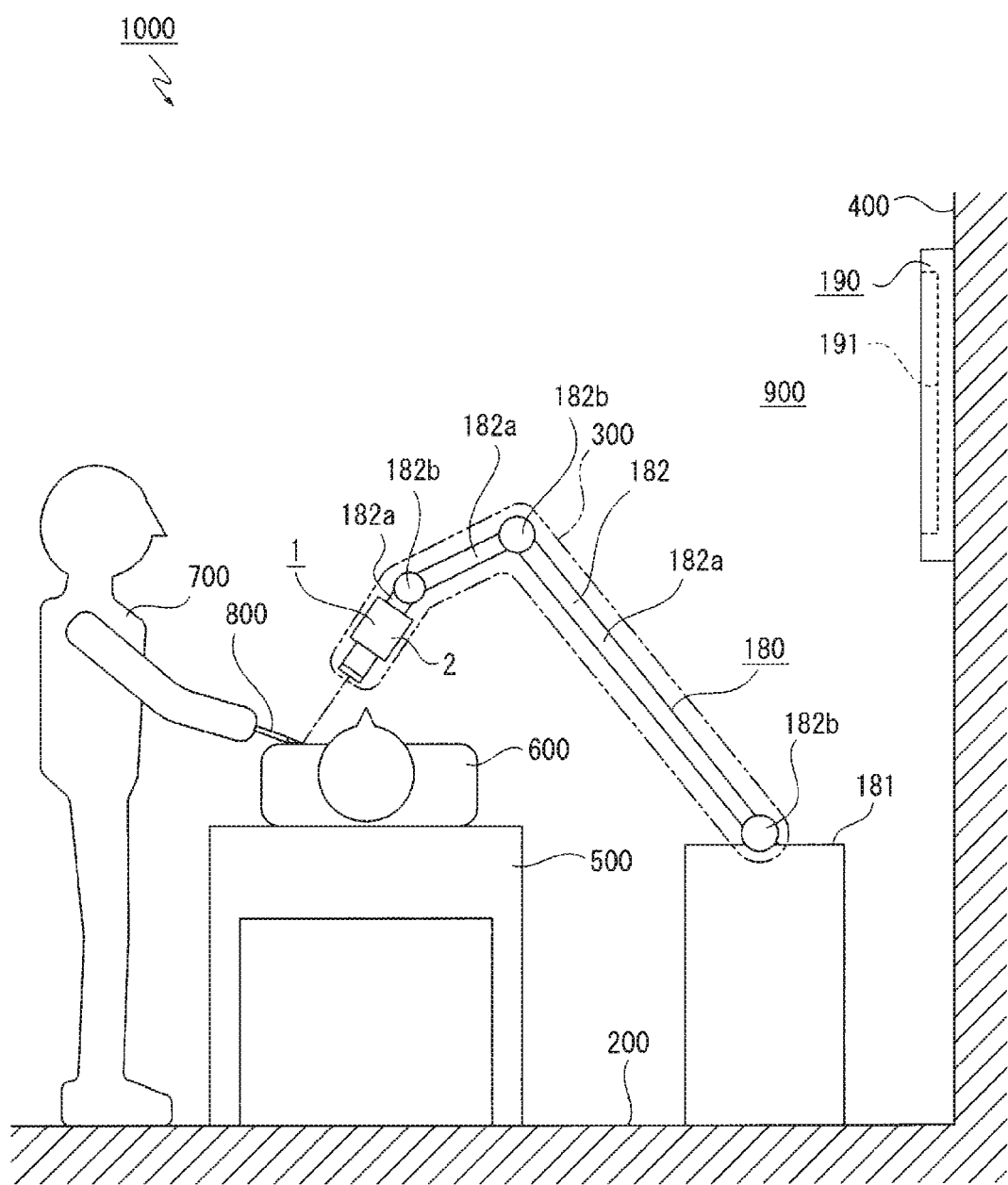
FIG. 1 is a schematic diagram of a medical system including a medical observation device, illustrating an embodiment of a medical observation device and a lens barrel of the medical observation device of the present technology along with FIGS. 2 to 56.

First, a schematic configuration of a medical system in which the medical observation device is used will be described (with reference to FIG. 1).

The medical system 1000 is a system installed in an indoor area 900, for example, an operation room or an examination room of a hospital, and includes a robot arm device 180 and a display device 190.

The robot arm device 180 has a base 181 installed on a floor 200, etc., and an arm 182 connected to the base 181.

The base 181 may be installed in a fixed state, and movable on the floor 200, or the like. The arm 182 has a plurality of links 182a, 182a, . . . , and joints 182b, 182b, . . . which connect the links 182a, 182a, . . . to be rotatable. The link 182a connected to the base 181 can be rotated with respect to the base 181 due to the joint 182b.

A medical observation device 1 is mounted in the link 182a on the most leading end side. Since the links 182a, 182a, . . . of the arm 182 are rotatable with respect to other the links 182a, 182a, . . . or the base 181 due to the joints 182b, 182b, the links 182a, 182a, . . . are rotated in a desired direction and by a desired angle, and thus the medical observation device 1 can be disposed at a desired position having a desired orientation.

When a medical procedure such as a surgical operation or an examination is performed in the indoor area 900, the robot arm device 180 and medical observation device 1 are covered by a sterilization-processed transparent protection sheet 300, which is called a drape. Thus, manual manipulation with respect to a manipulation unit of the medical observation device 1 by an operator 700, such as a doctor, is performed from the outside of the protection sheet 300 in a state in which the protection sheet 300 overlaps the manipulation unit and thus the operator grips them together.

The display device 190 is mounted in a wall 400, or the like, and has a display unit 191 such as a display on which images or videos captured by the medical observation device 1 are projected. Note that the display device 190 may be a monitor device disposed on a table in a fixed state or a movable state, or a monitor device installed to be fixed to or movable on the floor 200, or the like.

A procedure table 500, for example, an operating table, an examination bed, or the like is disposed in the indoor area 900, and a procedure subject 600 such as a patient or an examinee lies on the procedure table 500. The operator 700 such as a doctor performs, for example, a medical procedure on a lesion of the procedure subject 600 using a medical instrument 800 such as a scalpel or a forceps.

When the operator 700 performs the medical procedure for the procedure subject 600, an image or video of the lesion of the procedure subject 600 is captured by the medical observation device 1, and the captured image or video is projected on the display unit 191 of the display device 190. The operator 700 performs the medical procedure while viewing the image or video projected on the display unit 191 and the lesion.

Note that, during the medical procedure, or the like, the robot arm device 180 may be operated and the links 182a, 182a, . . . rotated electrically, or the operator 700, or the like may grip the medical observation device 1 or the links 182a, 182a, . . . to manually rotate the links 182a, 182a, . . . in a desired direction at a desired angle.

Thus, when the operator 700 or the like grips the medical observation device 1, in particular, it is desirable for the medical observation device 1 to be miniaturized in its radial direction in order to achieve enhancement in a grip property of the medical observation device 1.

In addition, the operator 700 often performs medical procedures while viewing lesions. Thus, miniaturizing the medical observation device 1 in its radial direction is particularly important to prevent the medical observation device 1 from obstructing visual recognition when a lesion is visually recognized.

Note that the medical observation device 1 may be configured to be rotatable with respect to the link 182*a* at the most leading end side in an arbitrary direction, and in this case, an orientation of the medical observation device 1 can be easily and smoothly set.

[Schematic Configuration of Medical Observation Device]

Figure 2:
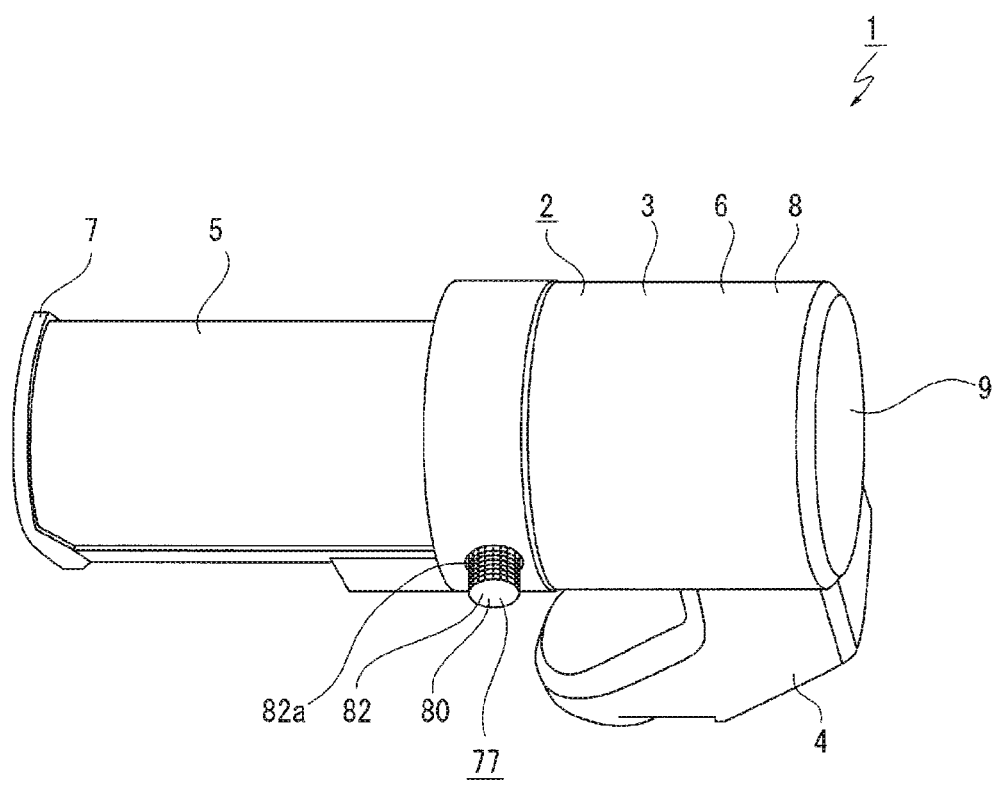
FIG. 2 is a schematic perspective diagram of the medical observation device.

Next, a schematic configuration of the medical observation device 1 will be described (with reference to FIG. 2).

The medical observation device 1 has a portion excluding a part of a lens barrel to be described below disposed inside an outer housing 2.

The outer housing 2 has a main body 3 formed in a shape stretching in the front-rear direction and a mounted section 4 that protrudes from a rear end of the main body 3.

The main body 3 is formed such that a front section 5 that is substantially a front half portion of the main body is smaller than a rear section 6 that is substantially a rear half portion thereof.

The front section 5 is formed in a cylindrical shape, and a cover 7 at least a part of which is transparent is mounted in the front end part of the front section 5.

The rear section 6 has an outer circumference part 8 formed in a substantially cylindrical shape and a circular rear face part 9 that is connected to the rear end of the outer circumference part 8. The outer circumference part 8 has insertion holes formed in the circumferential direction at the positions that are opposed to each other by about 180°.

The mounted section 4 protrudes to a side from a rear end part of the rear section 6. The mounted section 4 is mounted in the link 182*a* on the most leading end side of the robot arm device 180.

[Schematic Configuration of Lens Barrel]

Next, a schematic configuration of the lens barrel will be described (with reference to FIGS. 3 and 4).

The lens barrel 10 is formed combining the front barrel section 11, the intermediate barrel section 12, and the rear barrel section 13 in that order from the front side in a shape stretching in the front-rear direction as a whole. The lens barrel 10 has an imaging optical system having various lenses and the like to image a subject and an image sensor that photoelectrically converts an image of the subject captured by the imaging optical system, and the direction of a line from the imaging optical system to the image sensor (the front-rear direction) is set to be the optical axis direction.

The lens barrel 10 has the imaging optical system provided as a binocular optical system, respective elements of the imaging optical system such as lenses are disposed on the left and right in the intermediate barrel section 12 and the rear barrel section 13, and thus light coming during imaging is incident on the respective left optical system and right optical system, thereby forming two light paths. In this manner, the lens barrel 10 receives light incident on the two respective optical systems, and thus can acquire a stereoscopic image using parallax of the incident light.

Excluding a lens group disposed on the rear end side, elements of the imaging optical system of the front barrel section 11 such as lenses are not disposed from left to right, and light that is taken in has one path. The front barrel section 11 is designed to be an objective system and mainly has a function of taking in light and a focusing function of putting focus on the light that is taken in. Thus, a focusing mechanism is disposed on the front barrel section 11.

The intermediate barrel section 12 is an image-forming system, and mainly has a zooming function of changing magnification by changing the diameter of light that is taken in. Thus, a zooming mechanism is disposed in the intermediate barrel section 12.

The rear barrel section 13 is an image-forming system, and mainly has a function of acquiring images of light that is taken in with different spectral characteristics. Specifically, a switching mechanism which can switch a plurality of optical elements of different kinds, for example, optical filters, is disposed in the rear barrel section 13, and thus images with different spectral characteristics can be acquired as the switching mechanism switches the optical filters. In addition, two image sensors which photoelectrically convert subject images captured by the imaging optical system are disposed on the left and right in a rear end part of the rear barrel section 13.

[Specific Configuration of Lens Barrel]

Next, a specific configuration of the lens barrel 10 will be described.

The lens barrel 10 is configured by combining the front barrel section 11, the intermediate barrel section 12, and the rear barrel section 13 in order from the front side as described above, and thus description will be provided below in order of the front barrel section 11, the intermediate barrel section 12, and the rear barrel section 13.

<Configuration of Front Barrel Section>

First, a configuration of the front barrel section 11 will be described (refer to FIGS. 3 to 7).

Figure 3:
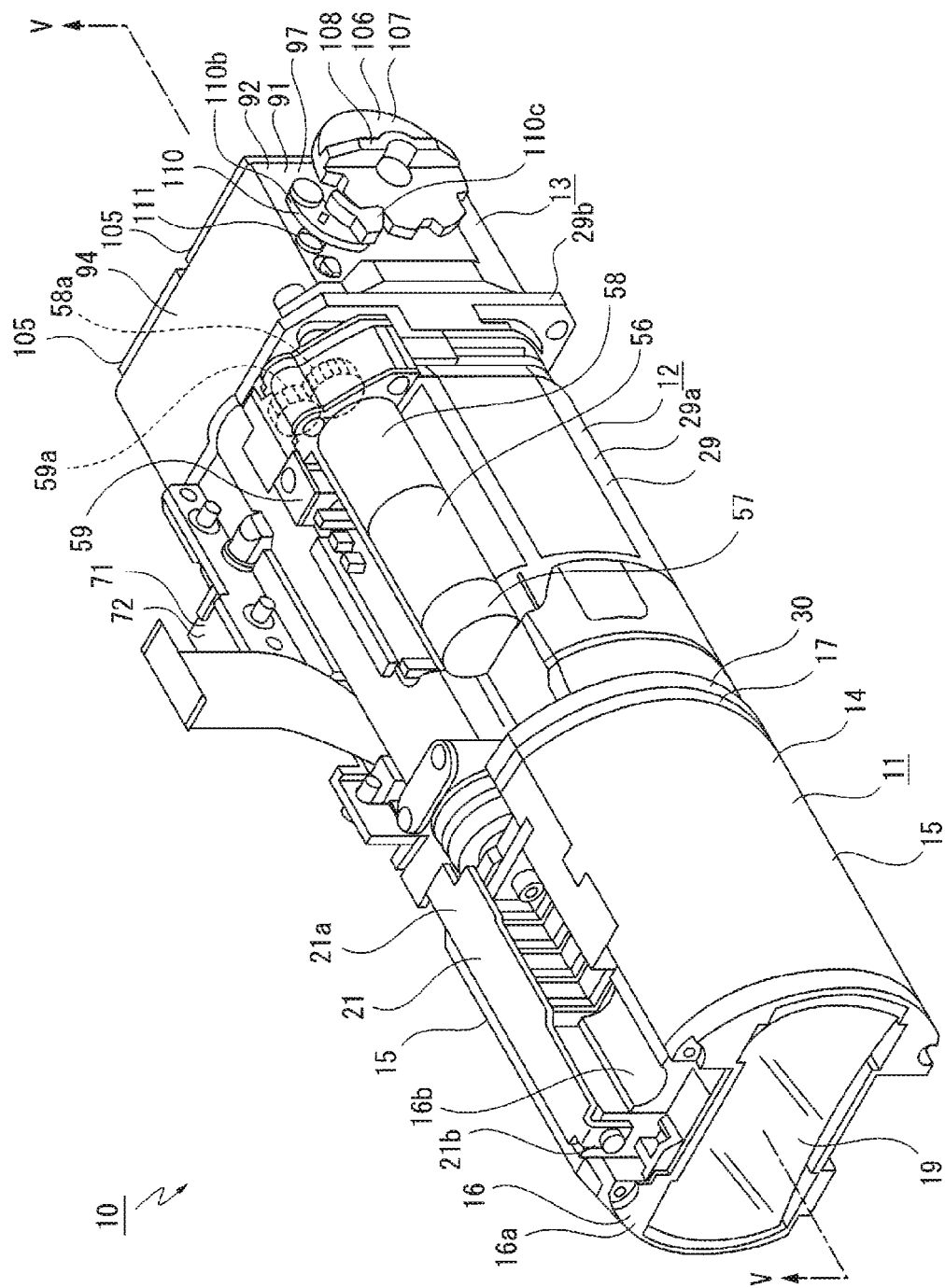
FIG. 3 is a perspective diagram of the lens barrel.
Figure 4:
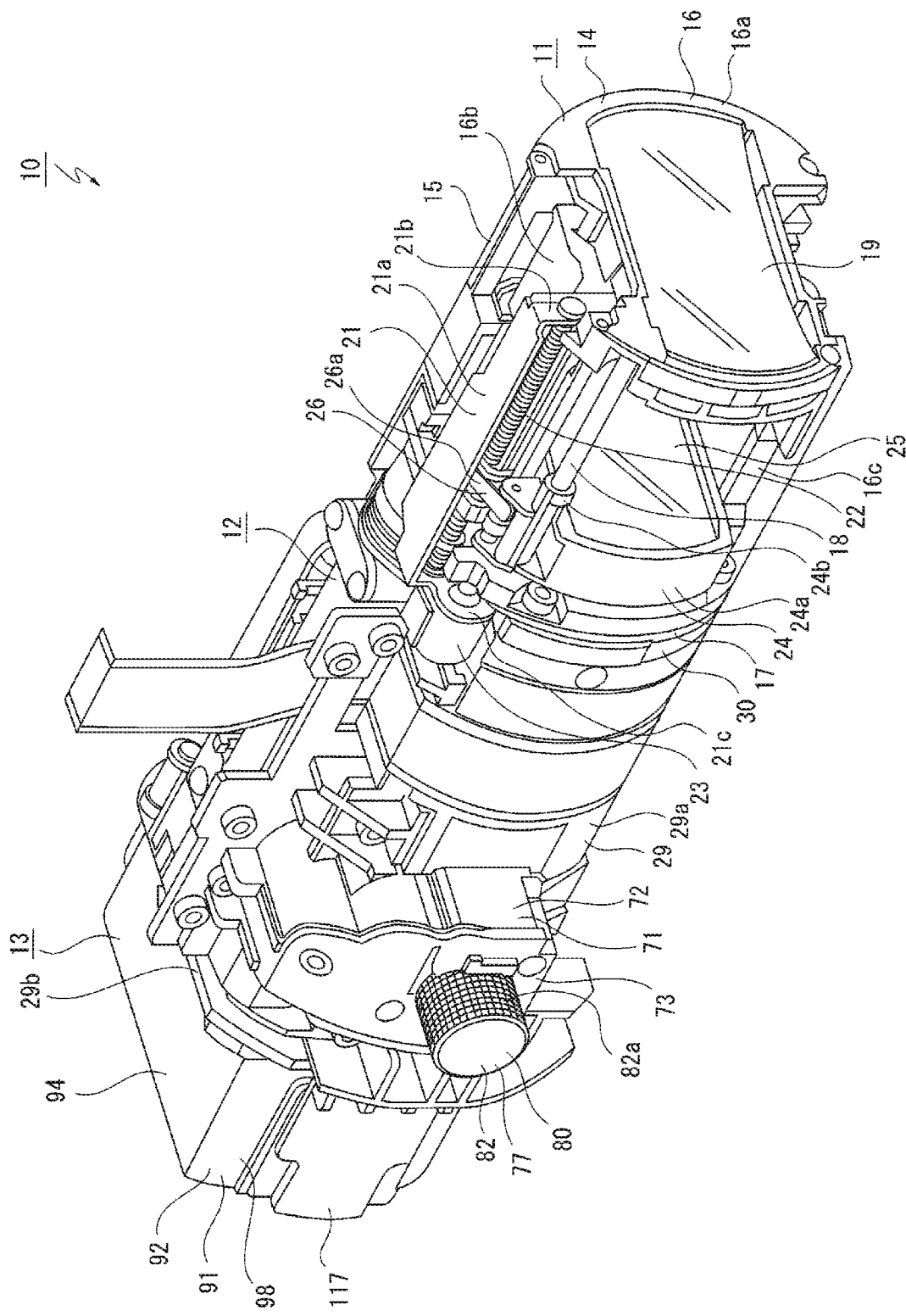
FIG. 4 is a perspective diagram of the lens barrel with an omitted part of a front part support housing when viewed in a different direction from FIG. 3.
Figure 5:
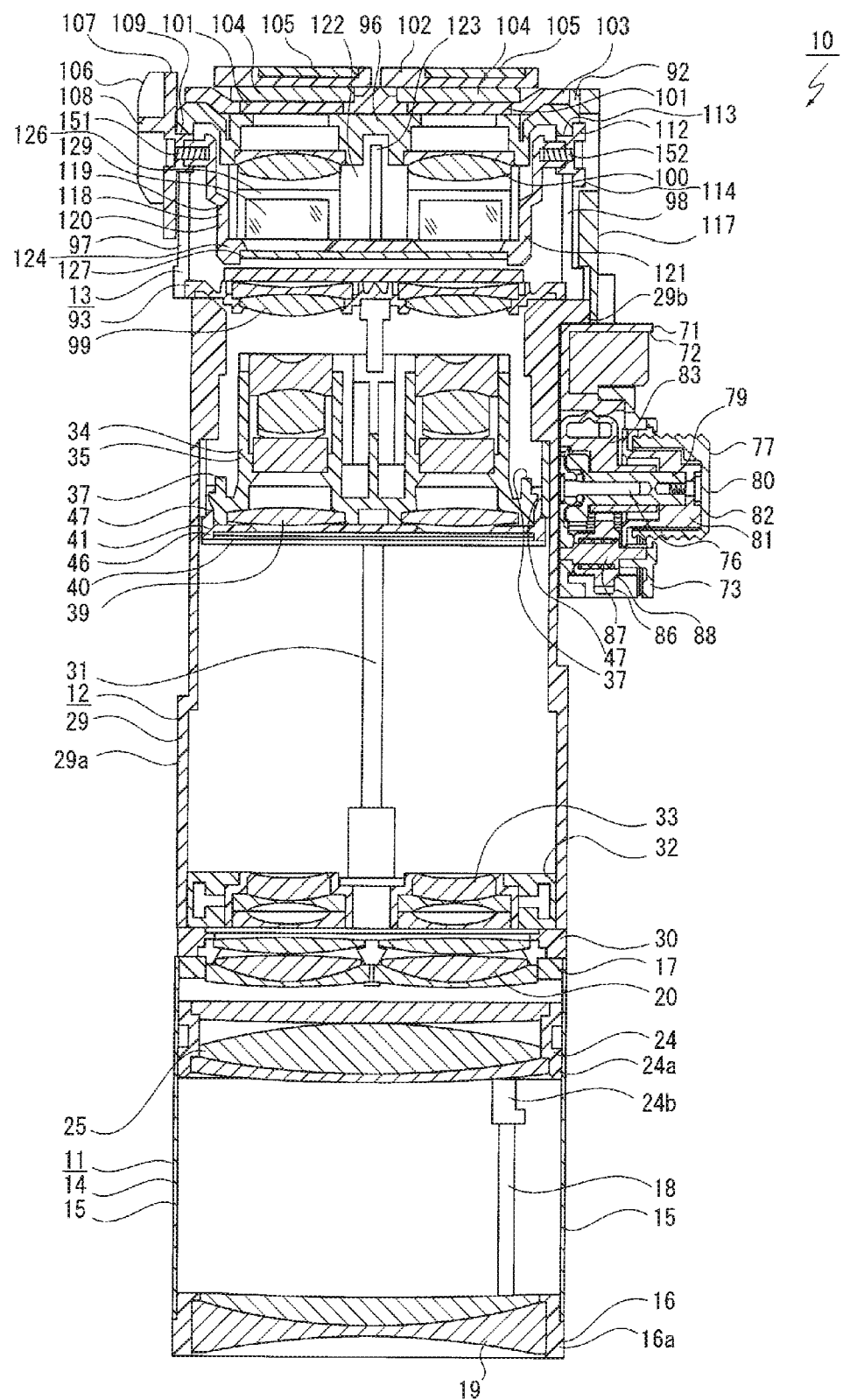
FIG. 5 is a cross-sectional diagram taken along the V-V line of FIG. 3.

The front barrel section 11 has respective necessary parts disposed inside and outside a front part support housing 14 (refer to FIG. 3 to FIG. 5). The front barrel section 11 is disposed inside the main body 3 of the outer housing 2.

The front part support housing 14 has outer circumferential members 15 and 15 that stretch forward and backward, a first coupling member 16 that is mounted on the outer circumferential members 15 and 15, and a frame-shaped second coupling member 17 that is mounted on the outer circumferential members 15 and 15.

The outer circumferential members 15 and 15 are positioned separately from each other on the left and right, and are formed in a substantially circular arc shape projecting outward (to the sides).

The first coupling member 16 has a frame shape part 16*a* having a hole penetrating it forward and backward, a protrusion part 16*b* that protrudes rearward from an upper end part of the frame shape part 16*a*, and a connection protrusion part 16*c* that protrudes rearward from a lower end part of the frame shape part 16*a*. The frame shape part 16*a* is mounted in the front end part of the outer circumferential members 15 and 15. The protrusion part 16*b* is positioned between the upper end parts of the outer circumferential members 15 and 15. The connection protrusion part 16*c* is positioned between the lower end parts of the outer circumferential members 15 and 15.

The second coupling member 17 is mounted on the rear end parts of the outer circumferential members 15 and 15.

The frame shape part 16*a* of the first coupling member 16 and the second coupling member 17 are formed in an oval shape that extends substantially horizontally, their upper and lower parts are formed to stretch to the left and right substantially linearly, and their left and right side parts are formed in a substantially circular arc shape projecting outward (to the sides). Thus, with the lens barrel 10 disposed inside the main body 3 of the outer housing 2, respective spaces are formed between the upper end parts and the lower end parts of the outer circumferential members 15 and 15, and thus the spaces are a first disposition space 11a and a second disposition space 11b (refer to FIG. 6).

Figure 6:
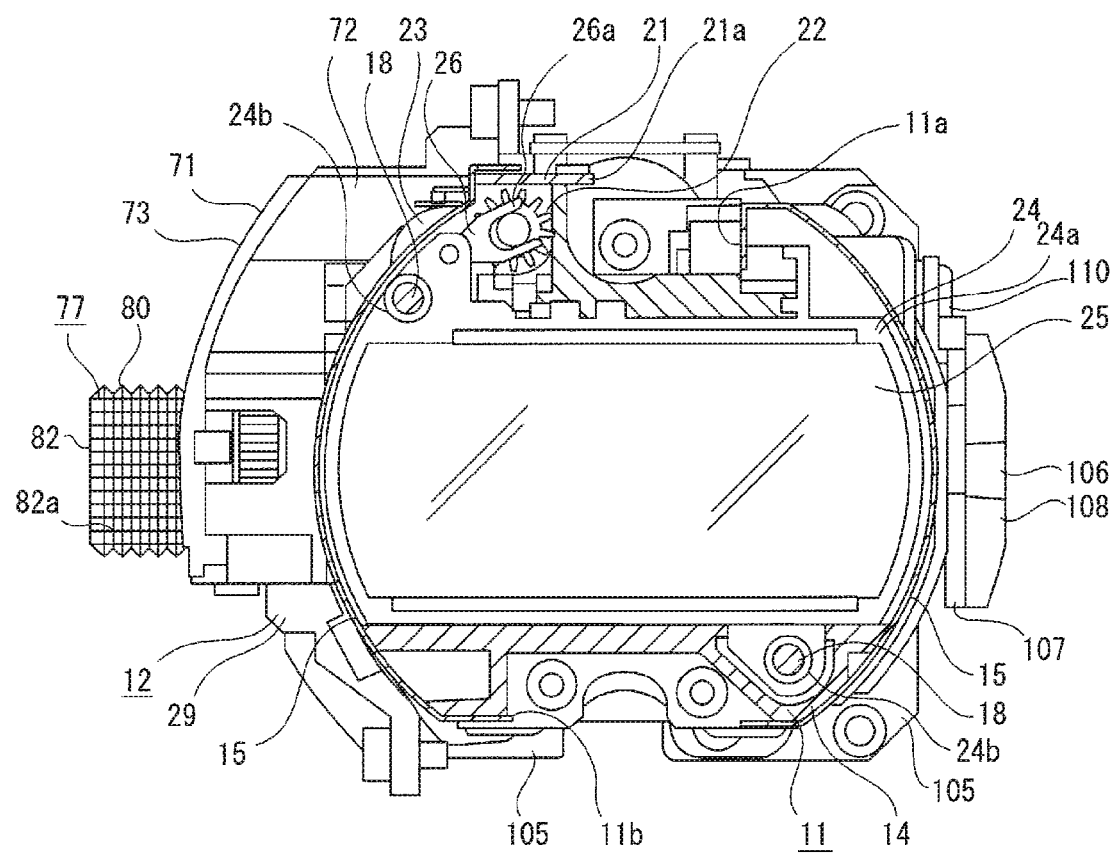
FIG. 6 is an enlarged cross-sectional diagram illustrating the inner structure of a front barrel section.

Guiding shafts 18 and 18 that stretch forward and backward are disposed separately from each other on the upper and lower sides between the frame shape part 16a of the first coupling member 16 and the second coupling member 17 (refer to FIG. 4 to FIG. 6). The front end parts of the guiding shafts 18 and 18 are mounted on the upper end part and the lower end part of the frame shape part 16a, and the rear end parts thereof are mounted on the upper end part and the lower end part of the second coupling member 17.

A front-end-side lens group 19 is held in the frame shape part 16a of the first coupling member 16 (refer to FIGS. 3 to 6). The front-end-side lens group 19 is disposed in a fixed state and formed in an oval shape that extends substantially horizontally.

First lens groups 20 and 20 are held on the left and right sides in the second coupling member 17 (refer to FIG. 5). The first lens groups 20 and 20 are disposed in a fixed state.

A support plate 21 is mounted on an upper end part of the front part support housing 14, and thus the support plate 21 is positioned in the first disposition space 11a (refer to FIGS. 3, 4 and 6). The support plate 21 has an extending face part 21a that stretches forward and rearward, a support face part 21b that protrudes downward from the front end part of the extending face part 21a, and a motor-mounted face part 21c that protrudes downward from the rear end part of the extending face part 21a.

A lead screw 22 that stretches forward and rearward supports the support plate 21. Both the front and rear ends of the lead screw 22 are supported to be freely rotated with respect to respective parts of the support plate 21, and positioned in the first disposition space 11a.

The focus motor 23 is mounted on the motor-mounted face part 21c of the support plate 21 (refer to FIGS. 4 and 6). A portion of the focus motor 23 excluding its motor shaft is mounted on the rear face side of the motor-mounted face part 21c, and the motor shaft penetrates the motor-mounted face part 21c from the rear side. The focus motor 23 is positioned on the outer face side of the front part support housing 14.

When the motor shaft rotates in the focus motor 23, a driving force of the focus motor 23 is transmitted to the lead screw 22 through the motor shaft, and thus the lead screw 22 rotates in the direction according to the rotation direction of the motor shaft.

A focus frame 24 is supported by the guiding shafts 18 and 18 to be freely slidable (refer to FIGS. 4 to 6). The focus frame 24 has a lens holding part 24a formed in an oval shape that extends substantially horizontally, and supported protrusion parts 24b and 24b that protrude upward and downward from the lens holding part 24a. The focus frame 24 is supported such that the supported protrusion parts 24b and 24b are freely slidable with respect to the guiding shafts 18 and 18.

A focus lens 25 is held by the lens holding part 24a of the focus frame 24. The focus lens 25 is formed in an oval shape that extends substantially horizontally.

A nut member 26 is supported by the supported protrusion parts 24b on the upper side of the focus frame 24. A part of the nut member 26 is provided as a screw part 26a, and thus the screw part 26a is screwed onto the lead screw 22. When a driving force of the focus motor 23 causes the lead screw 22 to rotate, the nut member 26 is sent in the direction according to the rotation direction of the lead screw 22, and the focus frame 24 holding the focus lens 25 is guided by the guiding shafts 18 and 18 and moved in the front-rear direction (the optical axis direction), and thereby focusing is performed.

Figure 7:
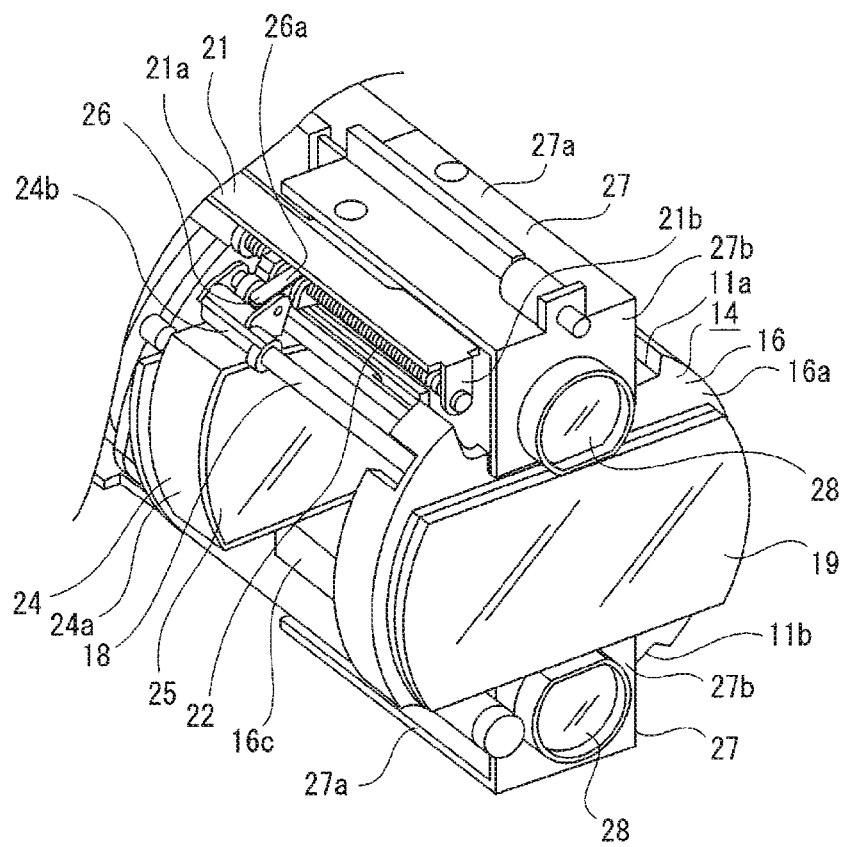
FIG. 7 is an enlarged perspective diagram illustrating the front end part of the front barrel section.

Mounting plates 27 and 27 are mounted on upper and lower end parts of the front part support housing 14 (refer to FIG. 7). Each mounting plate 27 has a mounted plate part 27a that stretches forward and rearward, and a mounting part 27b that protrudes upward and downward from the front end part of the mounted plate part 27a. The mounting parts 27b and 27b of the mounting plates 27 and 27 have light sources 28 and 28 such as light emitting diodes installed therein, and the light sources 28 and 28 are respectively immediately above and below the front-end-side lens group 19.

The light sources 28 and 28 have a function of improving visibility of a lesion of the procedure subject 600 by irradiating the lesion during a medical procedure and helping acquire bright and vivid images and videos.

The upper-side mounting plate 27 and the upper-side light source 28 are positioned in the first disposition space 11a, and the lower-side mounting plate 27 and the lower-side light source 28 are positioned in the second disposition space 11b.

In the medical observation device 1, the front-end-side lens group 19 and the focus lens 25 are formed in the oval shape that extends substantially horizontally as described above, thereby being formed in a so-called D-cut shape obtained by cutting upper and lower end parts of a circular shape out, the first disposition space 11a is formed on the upper side of the front part support housing 14, and the second disposition space 11b is formed on the lower side of the front part support housing 14.

Since the first disposition space 11a is formed on the upper side of the front part support housing 14 as described above, a focus driving mechanism having the support plate 21, the lead screw 22, and the like can be disposed in the first disposition space 11a, and thus it is unnecessary to increase the size of the front barrel section 11 to secure a disposition space of the focus driving mechanism, and the medical observation device 1 can be minimized with a sufficient disposition space of the focus driving mechanism secured.

In addition, the first disposition space 11a and the second disposition space 11b are formed on the upper and lower sides of the front part support housing 14 in the medical observation device 1.

Thus, the mounting plates 27 and 27 and the light sources 28 and 28 can be disposed in the first disposition space 11a and the second disposition space 11b, and it is accordingly unnecessary to increase the size of the front barrel section 11 to secure disposition spaces of the mounting plates 27 and 27 and the light sources 28 and 28, and thus the medical observation device 1 can be minimized with a sufficient disposition space of the mounting plates 27 and 27 and the light sources 28 and 28.

Furthermore, by disposing the support plate 21, the lead screw 22, the mounting plates 27 and 27, and the light sources 28 and 28 in the first disposition space 11a or the second disposition space 11b, the medical observation device 1 can be minimized, and thus can be easily gripped when the operator 700 or the like grips the medical observation device 1, and thereby a gripping property can be improved.

Moreover, the light sources 28 and 28 are positioned at the front end part of the medical observation device 1, and thus shadows are rarely generated on a lesion of the procedure subject 600 when the light sources 28 and 28 illuminate the lesion, and therefore visibility of the lesion can be improved and clear and vivid images and videos can be acquired.

<Configuration of Intermediate Barrel Section>

Next, a configuration of the intermediate barrel section 12 will be described (with reference to FIGS. 3, 4, and 5, and FIGS. 8 to 28).

The intermediate barrel section 12 has an intermediate support housing 29 and respective necessary parts mounted or supported inside and outside of the intermediate support housing 29 (refer to FIGS. 3 to 5). The intermediate barrel section 12 is disposed inside the main body 3 of the outer housing 2, excluding a part of the manual manipulation knob to be described below.

Figure 8:
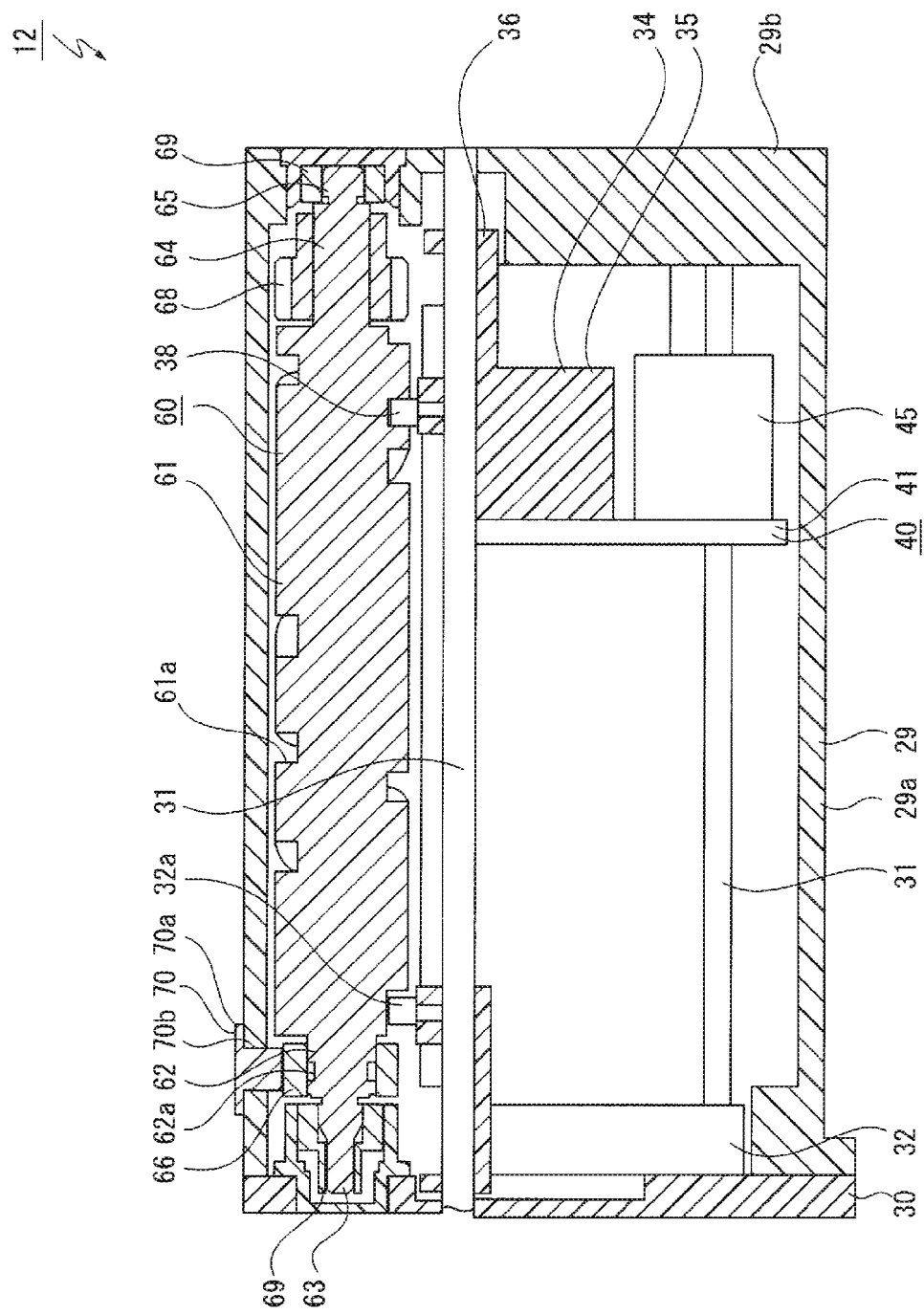
FIG. 8 is a vertical cross-sectional diagram of an intermediate barrel section.

The intermediate support housing 29 has a circumferential face part 29a that is formed in a substantially cylindrical shape stretching forward and rearward, and a rear face part 29b provided to block the opening on the rear side of the circumferential face part 29a as illustrated in FIGS. 5 and 8, and the rear face part 29b has two transmissive holes, which are not illustrated, formed on the left and right sides.

The rear face of a connection member 30 that blocks an opening on the front side of the circumferential face part 29a is mounted on the front end part of the intermediate support housing 29. The connection member 30 has two light-transmissive holes, which are not illustrated, formed on the left and right sides. The connection member 30 is mounted on the second coupling member 17 of the front part support housing 14 at its rear side.

Guiding shafts 31 and 31 that stretch forward and rearward are disposed in the intermediate support housing 29, separately from each other on the upper and lower sides in a fixed state. The front end part and the rear end part of the guiding shafts 31 and 31 are respectively mounted in the connection member 30 and the rear face part 29b of the intermediate support housing 29.

A first zoom lens holding frame 32 is supported by the guiding shafts 31 and 31 to be freely slidable. A cam pin 32a that protrudes upward is provided in the first zoom lens holding frame 32 (refer to FIG. 8). Second lens groups 33 and 33 are arranged on the left and right sides and held by the first zoom lens holding frame 32 (refer to FIGS. 5 and 9).

Figure 9:
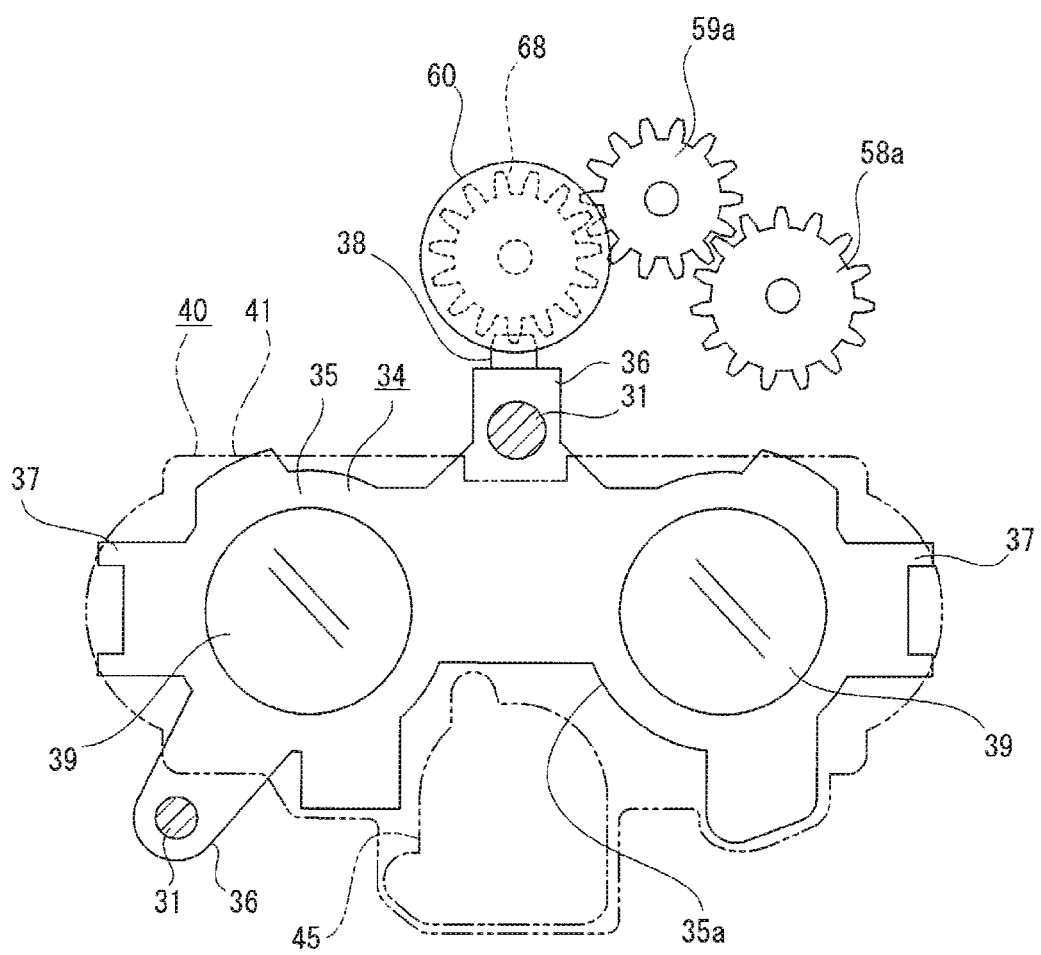

A second zoom lens holding frame 34 is supported by the guiding shafts 31 and 31 to be freely slidable (refer to FIGS. 5, 8 and 9). The second zoom lens holding frame 34 has a lens holding part 35 formed in a shape that extends horizontally, shaft-supported parts 36 and 36 that protrude from the lens holding part 35, mounting protrusion parts 37 and 37 that protrude from the left and right of the lens holding part 35, and a cam pin 38 that protrudes upward from the center of the lens holding part 35 in the left-right direction. A disposition notch 35a that opens downward is formed at the center of the lens holding part 35 in the left-right direction (refer to FIG. 9).

Third lens groups 39 and 39 are held by the lens holding part 35 on the left and right sides.

Figure 10:
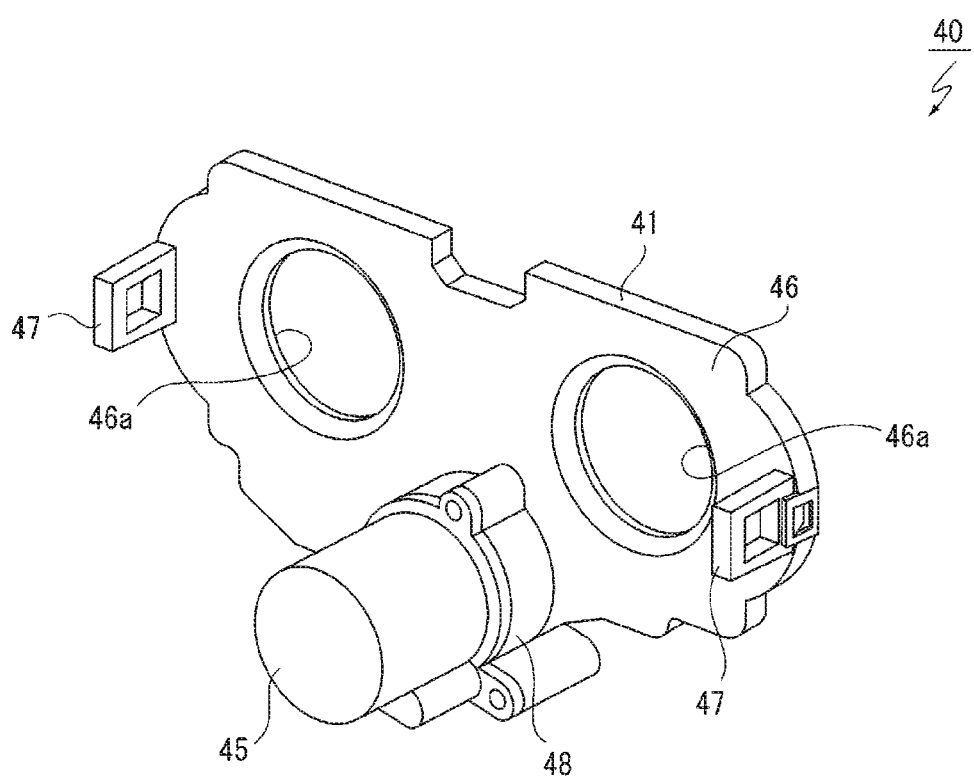
FIG. 10 is an enlarged perspective diagram of the iris unit.
Figure 11:
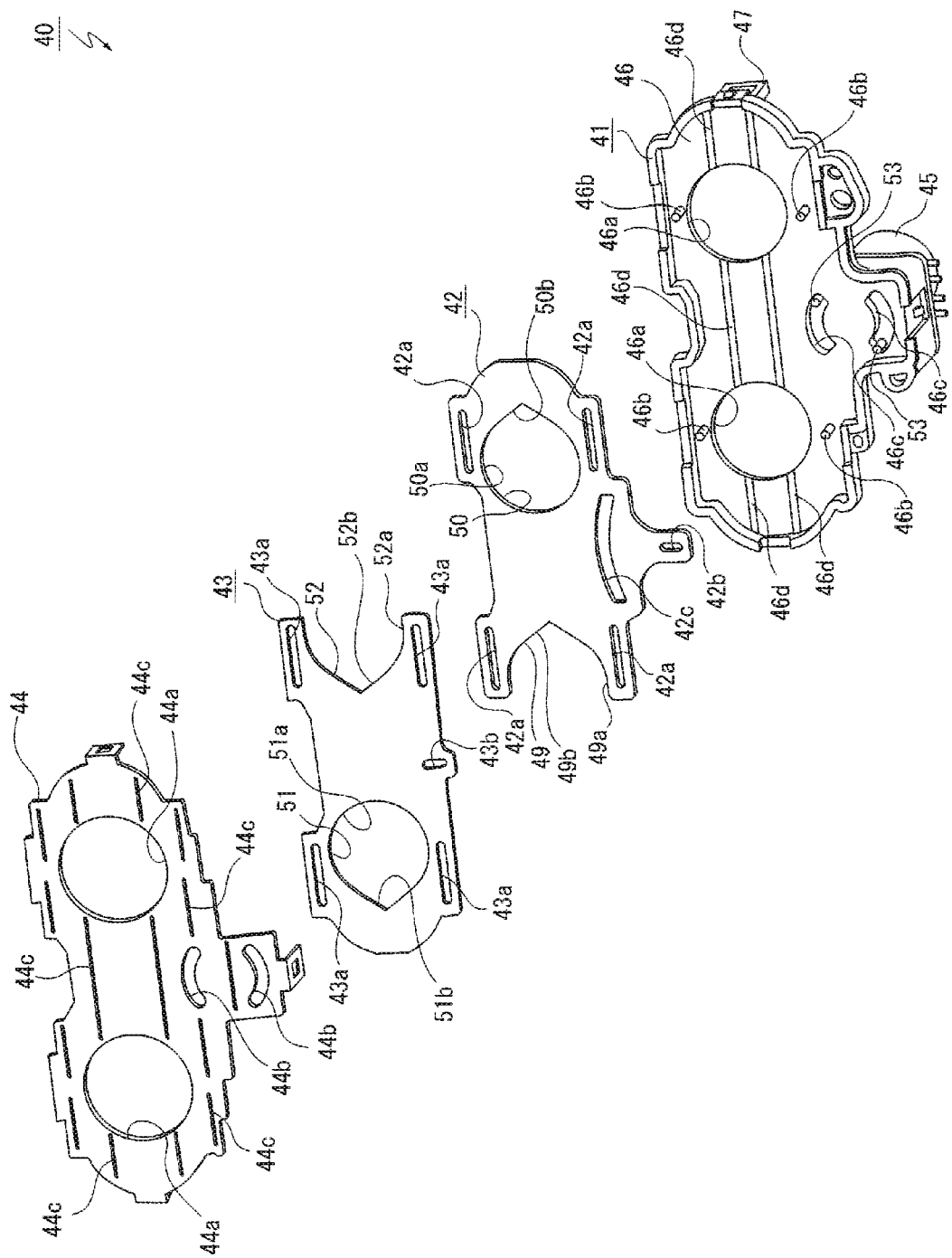
FIG. 11 is an enlarged exploded perspective diagram of the iris unit.

An iris unit 40 is mounted in the second zoom lens holding frame 34 (refer to FIGS. 5 and 9). The iris unit 40 has a base plate 41 formed in a shape that extends horizontally, a first blade 42 supported to be freely slidable with respect to the base plate 41, a second blade 43 supported to be freely slidable with respect to the base plate 41, a pressing plate 44 mounted on the base plate 41, and an iris motor 45 mounted on the base plate 41, as illustrated in FIG. 10 and FIG. 11.

The base plate 41 has a plate-shaped base part 46 that faces the front-rear direction, mounted protrusion parts 47 and 47 that each protrude rearward from the left and right end parts of the base part 46, and a motor attachment part 48 that protrudes rearward from the lower end part of the center of the base part 46 in the left-right direction.

Circular through holes 46a and 46a are formed separately from each other on the left and right sides of the base part 46. Four guiding shafts 46b, 46b, . . . that protrude rearward are provided on the front face of the base part 46 separately from each other on the upper, lower, left, and right sides (refer to FIGS. 11, 13 and 14). Shaft insertion holes 46c and 46c that are penetrated forward and rearward are formed at lower end positions of the base part 46, separately from each other on the upper and lower sides, the upper shaft insertion hole 46c is formed in a circular arc shape projecting upward, and the lower shaft insertion hole 46c is formed in a circular arc shape projecting downward. Slide protrusion threads 46d, 46d, . . . stretching to the left and right and projecting upward are provided on the front face of the base part 46, separately from each other on the upper, lower, left and right sides.

The first blade 42 is formed in a sheet shape of which the thickness direction is the front-rear direction, and thereby is formed in a shape that extends horizontally. A light amount control notch 49 is formed at the left end part of the first blade 42. The portion of the light amount control notch 49 excluding its right end part is formed as a semi-circular part 49a formed in a substantially semi-circular shape, and the right end part is formed as a pointy part 49b formed in substantially an isosceles triangle shape projecting rightward. A light amount control hole 50 is formed in the right half part of the first blade 42. The part of the light amount control hole 50 excluding the right end part is formed as a circular part 50a formed in a substantially circular shape, and the right end part is formed as a pointy part 50b formed in substantially an isosceles triangle shape projecting rightward.

Four guided holes 42a, 42a, . . . that stretch to the left and right are formed in the first blade 42, separately from each other on the upper, lower, left, and right sides. A work hole 42b is formed at a lower end part of the center of the first blade 42 in the left-right direction, and the work hole 42b is formed in a linear shape stretching up and down. A shaft movement hole 42c is formed at a position near the lower end of the center of the first blade 42 in the left-right direction, and the shaft movement hole 42c is formed in a circular arc shape projecting upward.

The guide shafts 46b, 46b, . . . are inserted into the guided holes 42a, 42a, . . . , and thus the first blade 42 is supported by the base part 46 of the base plate 41 to be freely slidable in the left-right direction.

The second blade 43 is formed in a sheet shape of which the thickness direction is the front-rear direction, thereby being formed in a shape that extends horizontally. A light amount control hole 51 is formed in the left half part of the second blade 43. The part of the light amount control hole 51 excluding the left end part is formed as a circular part 51a formed in a substantially circular shape, and the left end part is formed as a pointy part 51b formed in substantially an isosceles triangle shape projecting leftward. A light amount control notch 52 is formed at the right end part of the second blade 43. The part of the light amount control notch 52 excluding the left end part is formed as a semi-circular part 52a formed in a substantially semi-circular shape, and the left end part is formed as a pointy part 52b formed in substantially an isosceles triangle shape projecting leftward.

Four guided holes 43a, 43a, . . . that stretch to the left and right are formed in the second blade 43, separately from each other on the upper, lower, left, and right sides. A work hole 43b is formed at a lower end part of the center of the second blade 43 in the left-right direction, and the work hole 43b is formed in a linear shape stretching up and down.

The second blade 43 overlaps the first blade 42 supported by the base part 46 from its front side, the respective guide shafts 46b, 46b, . . . are inserted into the guided holes 43a, 43a, . . . , and thus the second blade is supported by the base part 46 of the base plate 41 to be freely slidable in the left-right direction.

In the state in which the first blade 42 and the second blade 43 are supported by the base part 46, at least a part of the light amount control notch 49 and at least a part of the light amount control hole 51 are positioned on the front side of one through hole 46a of the base part 46, and at least a part of the light amount control hole 50 and at least a part of the light amount control notch 52 are positioned on the front side of the other through hole 46a of the base part 46.

The pressing plate 44 is formed in a sheet shape of which the thickness direction is the front-rear direction, thereby being formed in a shape that extends horizontally. Circular holes 44a and 44a are formed in the pressing plate 44, separately from each other on the left and right sides. Shaft holes 44b and 44b are formed at lower end positions of the center of the pressing plate 44 in the left-right direction, separately from each other on the upper and lower sides. The upper shaft hole 44b is formed in a circular arc shape projecting upward, and the lower shaft hole 44b is formed in a circular arc shape projecting downward.

Slide protrusion threads 44c, 44c, . . . stretching to the left and right with a rearward convex extrusion shape are provided in the pressing plate 44, separately from each other on the upper, lower, left, and right sides. The slide protrusion threads 44c, 44c, . . . increase strength of the pressing plate 44.

The pressing plate 44 overlaps the second blade 43 from its front side that overlaps the first blade 42 from its front side, and then is mounted on the base part 46 of the base plate 41. Thus, the pressing plate 44 presses the first blade 42 and the second blade 43 from their front sides, and exfoliation of the first blade 42 and the second blade 43 from the base part 46 is prevented.

In addition, in the state in which the pressing plate 44 is mounted on the base part 46, the slide protrusion threads 46d, 46d, . . . of the base part 46 come in contact with the rear surface of the first blade 42, and the slide protrusion threads 44c, 44c, . . . of the pressing plate 44 come in contact with the second blade 43.

Figure 12:
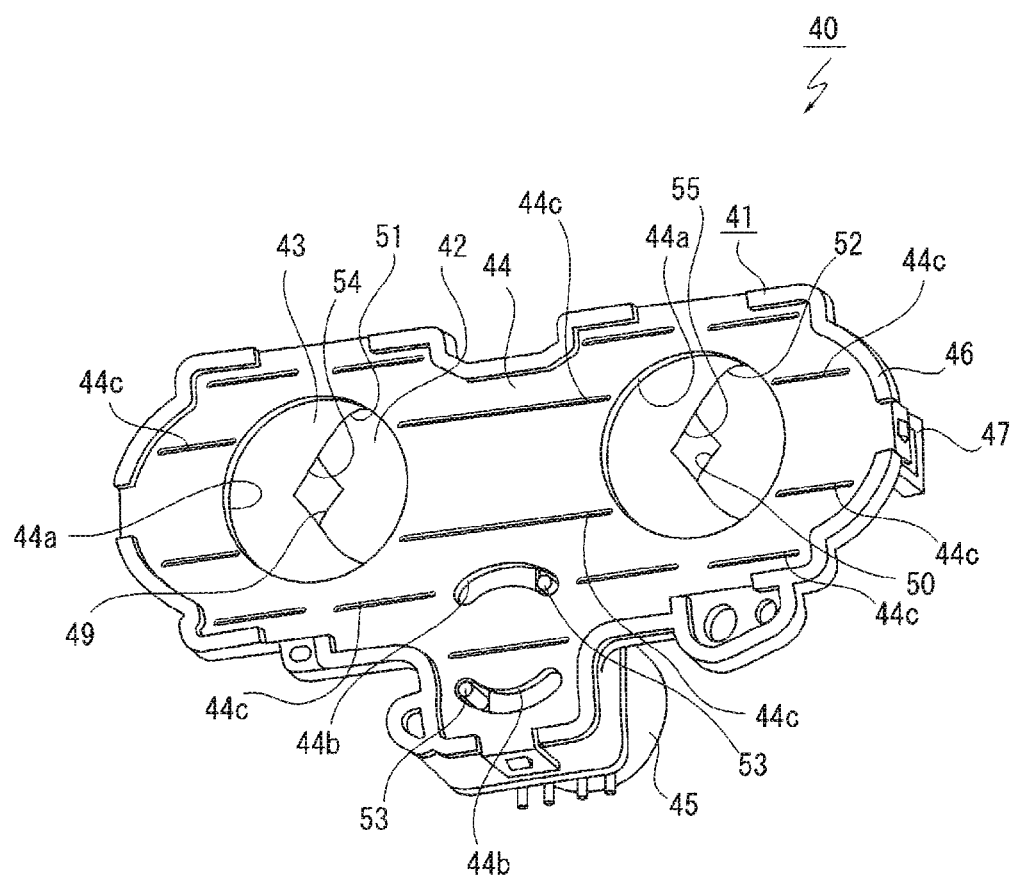
FIG. 12 is an enlarged perspective diagram illustrating the iris unit when viewed from the direction opposite to that of FIG. 10.

In the state in which the pressing plate 44 is mounted on the base part 46, at least a part of the light amount control notch 49 and at least a part of the light amount control hole 51 are positioned on the rear side of one circular hole 44a, and at least a part of the light amount control hole 50 and at least a part of the light amount control notch 52 are positioned on the rear side of the other circular hole 44a (refer to FIG. 12).

The iris motor 45 is mounted on the motor mounting part 48 of the base plate 41 on its rear side (refer to FIGS. 10 and 11). A driving member is connected to the motor shaft of the iris motor 45, which is not illustrated, and work shafts 53 and 53 that protrude forward are provided in the driving member. The work shafts 53 and 53 are positioned the same distance from the motor shaft in the radial direction having the motor shaft as its center. Thus, when the driving member is rotated due to a driving force of the iris motor 45, the work shafts 53 and 53 move around the motor shaft of the iris motor 45 in the circumferential direction.

Figure 13:
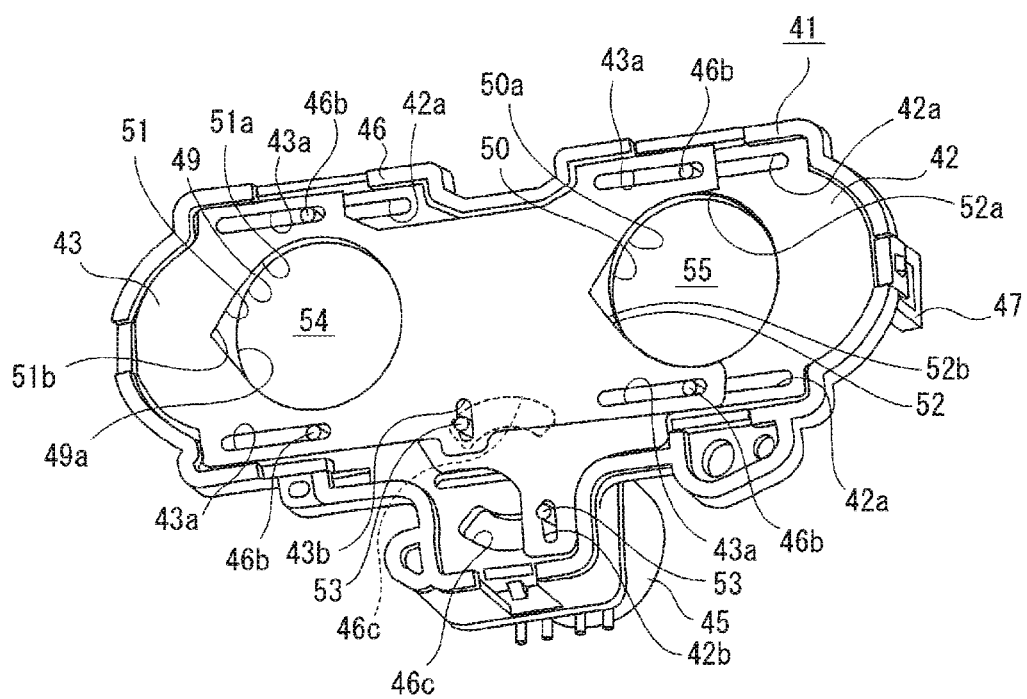
FIG. 13 is an enlarged perspective diagram illustrating a state in which a first blade and a second blade are moved to the outermost side.

The one work shaft 53 is inserted into the shaft insertion hole 46c of the base part 46, the shaft movement hole 42c of the first blade 42, the work hole 43b of the second blade 43, and the upper shaft hole 44b of the pressing plate 44 in order as illustrated in FIG. 13, and engaged with the work hole 43b to be freely slidable. The other work shaft 53 is inserted into the lower shaft insertion hole 46c of the base part 46, the work hole 42b of the first blade 42, and the lower shaft hole 44b of the pressing plate 44 in order, and engaged with the work hole 42b to be freely slidable.

Figure 14:
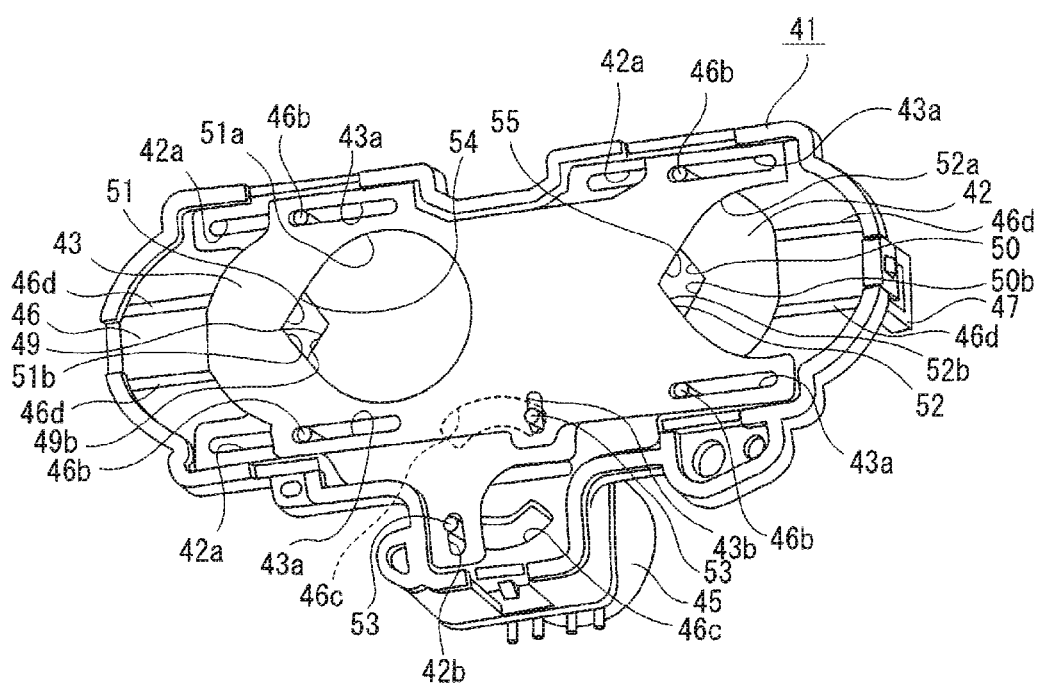
FIG. 14 is an enlarged perspective diagram illustrating a state in which the first blade and the second blade are moved to the innermost side.

In the iris unit 40 configured as described above, when the work shafts 53 and 53 are rotated due to driving of the iris motor 45, the work shafts 53 and 53 respectively slide along the opening edge of the work hole 42b of the first blade 42 and the opening edge of the work hole 43b of the second blade 43, and thus the first blade 42 and the second blade 43 are guided by the guide shafts 46b, 46b, . . . of the base plate 41 and slide with respect to the base part 46 in the left-right direction (refer to FIGS. 13 and 14).

At this time, the first blade 42 slides along the slide protrusion threads 46d, 46d, . . . provided in the base part 46 of the base plate 41, and thus a contact area of the first blade 42 with the base part 46 is small, a load of the sliding operation of the first blade 42 is reduced, and therefore a smooth sliding operation of the first blade 42 can be achieved.

In addition, the second blade 43 slides along the slide protrusion threads 44c, 44c, . . . provided in the pressing plate 44, and thus a contact area of the second blade 43 with the pressing plate 44 is small, a load of the sliding operation of the second blade 43 is reduced, and therefore a smooth sliding operation of the second blade 43 can be achieved.

When the first blade 42 and the second blade 43 respectively slide outward due to rotation of the work shafts 53 and 53 to one side, sizes of an opening 54 formed by the light amount control notch 49 and the light amount control hole 51 and an opening 55 formed by the light amount control hole 50 and the light amount control notch 52 become greater together as illustrated in FIG. 13, and thus an amount of light passing through the openings 54 and 55 increases.

On the other hand, when the first blade 42 and the second blade 43 slide inward due to rotation of the work shafts 53 and 53 to the other side, the sizes of the opening 54 formed by the light amount control notch 49 and the light amount control hole 51 and the opening 55 formed by the light amount control hole 50 and the light amount control notch 52 become smaller together as illustrated in FIG. 14, and thus an amount of light passing through the openings 54 and 55 decreases.

At this time, in a state in which the first blade 42 and the second blade 43 slide to the innermost side, the opening 54 is formed by a pointy part 49b of the light amount control notch 49 and the pointy part 51b of the light amount control hole 51, and the opening 55 is formed by the pointy part 50b of the light amount control hole 50 and the pointy part 52b of the light amount control notch 52 as illustrated in FIG. 14. Thus, there are no cases in which the openings 54 and 55 are not formed in the iris unit 40 even in the state in which the first blade 42 and the second blade 43 slide to the innermost side, and therefore there is an amount of light passing through the openings 54 and 55.

Note that, when the first blade 42 and the second blade 43 slide to the inner side, at least one guide shaft 46b of the base plate 41 comes in contact with the end edge of the guided hole 42a of the first blade 42 or the end edge of the guided hole 43a of the second blade 43, and thus further sliding of the first blade 42 or the second blade 43 to the inner side is regulated. Therefore, at least one guide shaft 46*b* of the base plate 41 functions as a stopper shaft which regulates sliding of the first blade 42 or the second blade 43 to the inner side.

Since the through holes 46*a* and 46*a* are not completely blocked and there is an amount of light passing through the openings 54 and 55 in the iris unit 40 even in the state in which the first blade 42 and the second blade 43 slide to the innermost side as described above, there are no cases in which images or videos are not projected during medical procedures, and thus the medical procedures can be sped up and improvement in safety of the medical procedures can be achieved.

Furthermore, the driving member having the two work shafts 53 and 53 is connected to the motor shaft of the iris motor 45 in the iris unit 40, and both the first blade 42 and the second blade 43 slide in the left-right direction due to driving of the iris motor 45.

Thus, since the first blade 42 and the second blade 43 operate due to the driving of the one iris motor 45, it is not necessary to provide different motors for respective driving of the first blade 42 and the second blade 43, and accordingly a reduction in manufacturing costs, miniaturization, and reliability in operations of the medical observation device 1 can be achieved.

Moreover, in the iris unit 40, the light amount control notch 49 and the light amount control hole 50 are formed to form the left and right openings 54 and 55 in the first blade 42, and the light amount control hole 51 and the light amount control notch 52 are formed to form the left and right openings 54 and 55 in the second blade 43.

Therefore, since a total of four blades, among which two blades form the openings 54 and 55, are not necessary for a binocular optical system, further reduction in manufacturing costs, miniaturization, and reliability in operations of the medical observation device 1 can be achieved.

The iris unit 40 is mounted in the second zoom lens holding frame 34 (refer to FIGS. 5 and 9). As the mounted protrusion parts 47 and 47 of the base plate 41 are engaged with the mounting protrusion parts 37 and 37 and a predetermined part is screwed, the iris unit 40 is mounted in the second zoom lens holding frame 34 from its front side.

In the state in which the iris unit 40 is mounted in the second zoom lens holding frame 34, the iris motor 45 positioned to protrude rearward from the base plate 41 and the driving member mounted on the iris motor 45 are positioned in the disposition notch 35*a* formed in the second zoom lens holding frame 34 (refer to FIG. 9). Thus, the iris motor 45 and the driving member are positioned on the lower side near the second zoom lens holding frame 34.

Since the disposition notch 35*a* is formed in the second zoom lens holding frame 34 and the iris motor 45 and the driving member are positioned in the disposition notch 35*a* in the state in which the iris unit 40 is mounted in the second zoom lens holding frame 34 as described above, the disposition space of the iris motor 45 and the driving member can attain efficiency, and miniaturization of the medical observation device 1 can be achieved accordingly. Particularly, miniaturization of the medical observation device 1 in the diameter direction can be achieved, and thus the medical observation device 1 can be easily gripped when gripped by the operator 700 or the like, and thereby a gripping property can be improved.

A driving motor 56, an encoder 57, and a gear head 58 are disposed at the front and back on the left end side of the upper end part of the intermediate support housing 29 (refer to FIG. 3).

The driving motor 56 is positioned between the encoder 57 and the gear head 58, the encoder 57 is positioned in front of the driving motor 56, and the gear head 58 is positioned behind the driving motor 56.

The encoder 57 has a function of detecting an amount of rotation of the driving motor 56.

The gear head 58 has a gear group disposed inside that is not illustrated and a feeding gear 58*a* disposed in its rear end part (refer to FIGS. 3 and 9), and is rotated by a driving force of the driving motor 56.

A gear body 59 is disposed near the gear head 58 in the intermediate support housing 29, and the gear body 59 has an intermediate gear 59*a*. The intermediate gear 59*a* meshes with the feeding gear 58*a* of the gear head 58.

Figure 15:
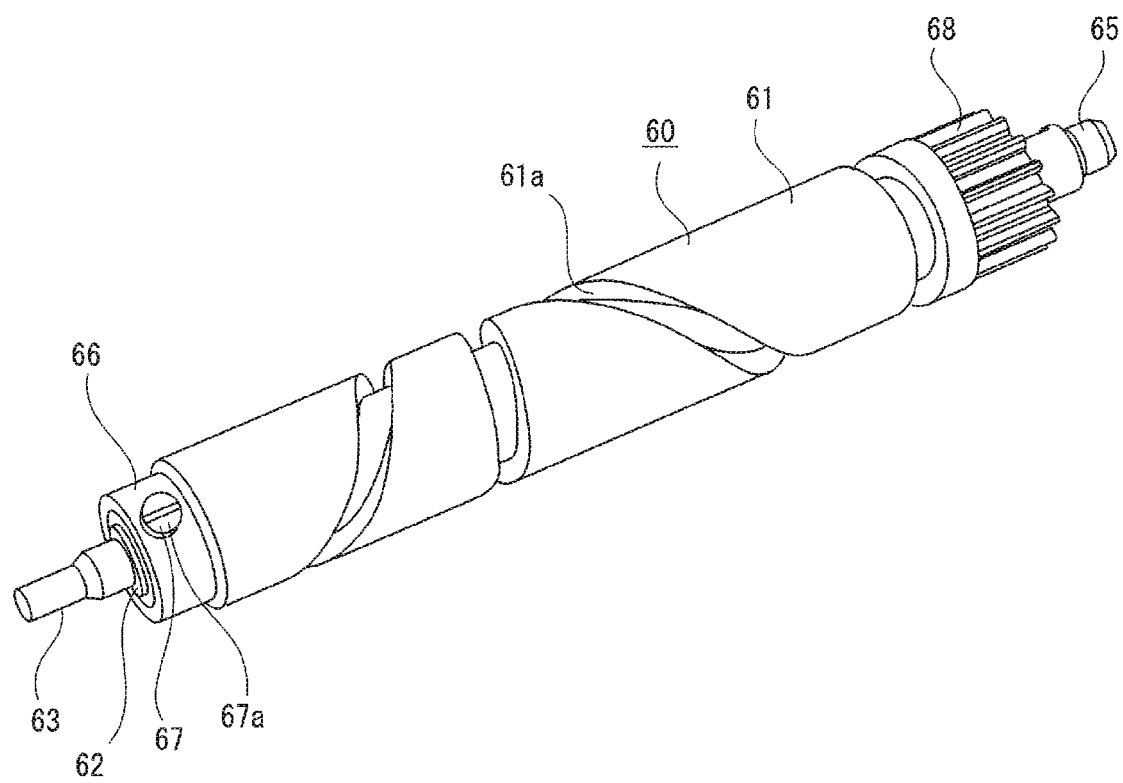
FIG. 15 is an enlarged perspective diagram illustrating a state in which a slide ring and a gear member are assembled with the driving cam.
Figure 16:
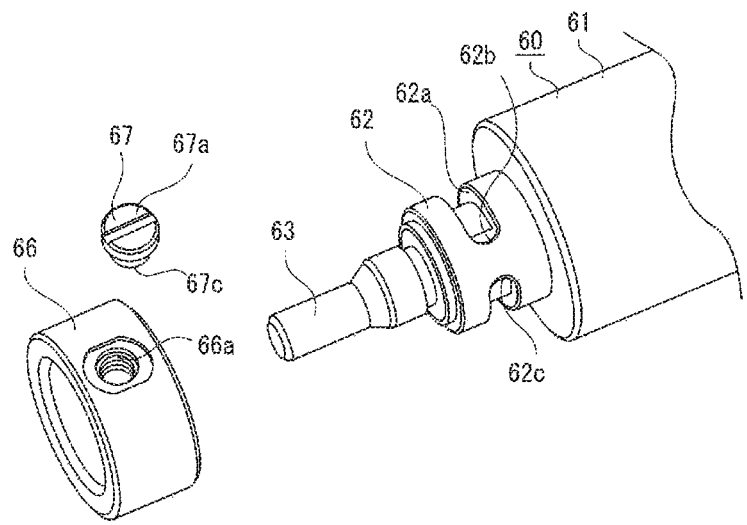
FIG. 16 is an enlarged exploded perspective diagram illustrating a part of the driving cam, the slide ring, and a stopper screw.
Figure 17:
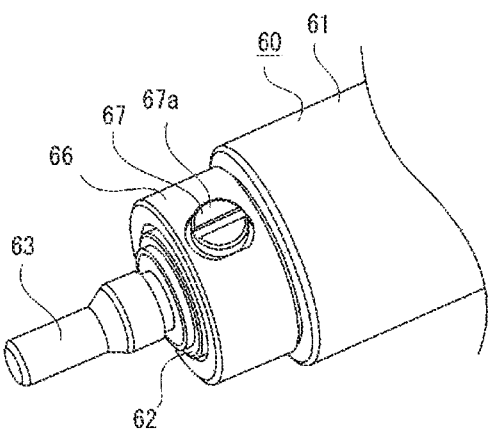
FIG. 17 is an enlarged perspective diagram illustrating a state in which the slide ring and the stopper screw are assembled with the driving cam.
Figure 18:
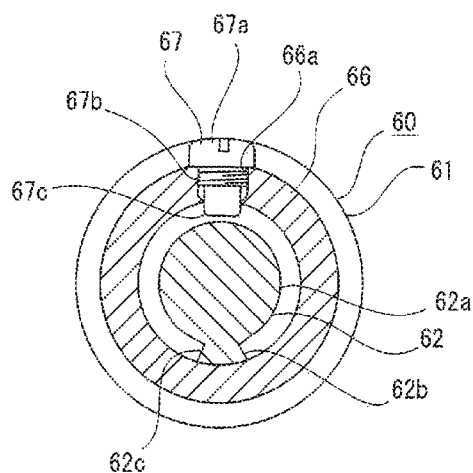
FIG. 18 is an enlarged cross-sectional diagram illustrating a state in which the slide ring and the stopper screw are assembled with the driving cam.

A shaft-shaped driving cam 60 that stretches forward and rearward is supported in the upper end part inside the intermediate support housing 29 to be freely rotatable (refer to FIG. 8). The driving cam 60 is constituted by a cam forming part 61 of which the diameter is largest, a work part 62 that protrudes forward from the cam forming part 61, a front supported shaft part 63 that protrudes forward from the work part 62, a gear mounting part 64 that protrudes rearward from the cam forming part 61, and a rear supported shaft part 65 that protrudes rearward from the cam attachment part 64 as illustrated in FIGS. 15 to 17.

A cam groove 61*a* is formed around the outer circumferential part of the cam forming part 61.

A slide groove 62*a* that stretches in the circumferential direction is formed in the work part 62. The slide groove 62*a* has one end edge formed as a first regulation edge 62*b* and the other end edge formed as a second regulation edge 62*c*. A slide ring 66 is externally fitted to and supported by the work part 62 to be freely rotatable. A screw hole 66*a* is formed to penetrate the slide ring 66 in the radial direction.

A stopper screw 67 is assembled with the slide ring 66. The stopper screw 67 is constituted by a head 67*a*, a screw shaft 67*b*, and a slide shaft 67*c*, and the slide shaft 67*c* protrudes from the screw shaft 67*b* in the direction opposite to the head 67*a*, and thus has a diameter a little bit smaller than the screw shaft 67*b*. The stopper screw 67 is assembled with the slide ring 66 as the screw shaft 67*b* is screwed into the screw hole 66*a*. In the state in which the stopper screw 67 is assembled with the slide ring 66, the head 67*a* is positioned on the outer circumference side of the slide ring 66, and the slide shaft 67*c* is positioned on the inner circumference side of the slide ring 66 (refer to FIG. 18). The stopper screw 67 is engaged to be freely slidable when the slide shaft 67*c* is inserted into the slide groove 62*a* of the work part 62.

A gear member 68 is externally fitted and fixed to the gear mounting part 64 of the driving cam 60 (refer to FIG. 15). The gear member 68 meshes with the intermediate gear 59*a* of the gear body 59. Thus, a driving force of the driving motor 56 is transmitted to the gear member 68 from the feeding gear 58*a* via the intermediate gear 59*a*, and the driving cam 60 integrated with the gear member 68 in a direction according to a rotation direction of the driving motor 56 is rotated in the axial rotation direction.

Bearing members 69 and 69 are mounted inside the intermediate support housing 29, separately from each other on the front and rear sides (refer to FIG. 8). The front supported shaft part 63 and the rear supported shaft part 65 of the driving cam 60 are supported by the bearing members 69 and 69 to be freely rotatable, and disposed inside the intermediate support housing 29.

Figure 19:
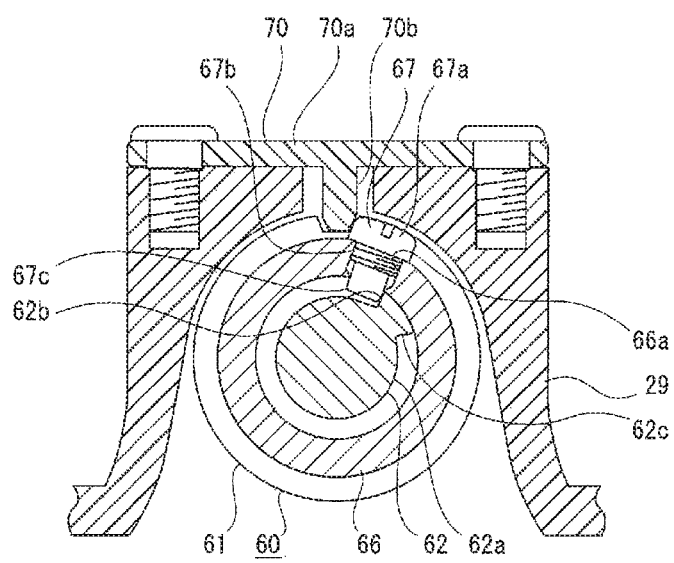
FIG. 19 is an enlarged cross-sectional diagram illustrating an operation when the driving cam rotates along with FIGS. 20 to 22, and illustrating a state in which the stopper screw is in contact with a regulation pin of a stopper base and the regulation pin regulates rotation of the driving cam to one side.

A stopper base 70 is mounted in the intermediate support housing 29 above the driving cam 60 (refer to FIGS. 8 and 19). The stopper base 70 has a cover part 70a that covers the driving cam 60 stretching forward and rearward from above and a regulation pin 70b that protrudes downward from the cover part 70a. The regulation pin 70b is positioned above the slide ring 66 supported by the driving cam 60, and the leading end thereof can come in contact with the head 67a of the stopper screw 67 assembled with the slide ring 66.

The cam pin 32a of the first zoom lens holding frame 32 and the cam pin 38 of the second zoom lens holding frame 34 are engaged with the cam groove 61a of the driving cam 60 to be freely slidable. Thus, when the driving cam 60 is rotated due to a driving force of the driving motor 56, the cam pin 32a and the cam pin 38 are sent in the front-rear direction in the direction according to the rotation direction of the driving cam 60, and the first zoom lens holding frame 32, the second lens groups 33 and 33 held by the first zoom lens holding frame 32, the second zoom lens holding frame 34, and the third lens groups 39 and 39 held by the second zoom lens holding frame 34 are guided by the guiding shafts 31 and 31 and move in the front-rear direction (the optical axis direction), and thereby zooming is performed.

As described above, the first zoom lens holding frame 32, the second lens groups 33 and 33, the second zoom lens holding frame 34, and the third lens groups 39 and 39 function as moving objects moved by the driving motor 56.

The driving cam 60 is set to be rotatable from one rotation end to the other rotation end (refer to FIGS. 19 to 22).

In the state in which the driving cam 60 is positioned at one rotation end, the head 67a of the stopper screw 67 assembled with the slide ring 66 comes in contact with the regulation pin 70b of the stopper base 70 as illustrated in FIG. 19, and thus rotation of the driving cam 60 in one direction is regulated by the regulation pin 70b. At this time, the first regulation edge 62b of the slide groove 62a formed in the work part 62 of the driving cam 60 comes in contact with the slide shaft 67c of the stopper screw 67. Thus, rotation of the driving cam 60 in one direction is regulated by the stopper screw 67.

Figure 20:
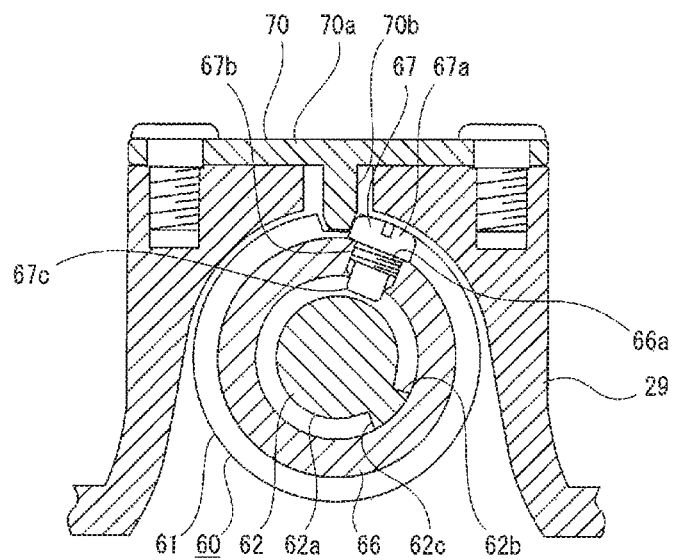
FIG. 20 is an enlarged cross-sectional diagram illustrating a state in which the driving cam rotates around the slide ring, subsequent to FIG. 19.

When a driving force of the driving motor 56 is transmitted to the driving cam 60 in the state in which the driving cam 60 is positioned at one rotation end, the driving cam 60 is rotated with respect to the slide ring 66 (refer to FIG. 20). When the driving cam 60 is rotated, the first regulation edge 62b is separated from the stopper screw 67, and the slide shaft 67c of the stopper screw 67 moves along the slide groove 62a.

Figure 21:
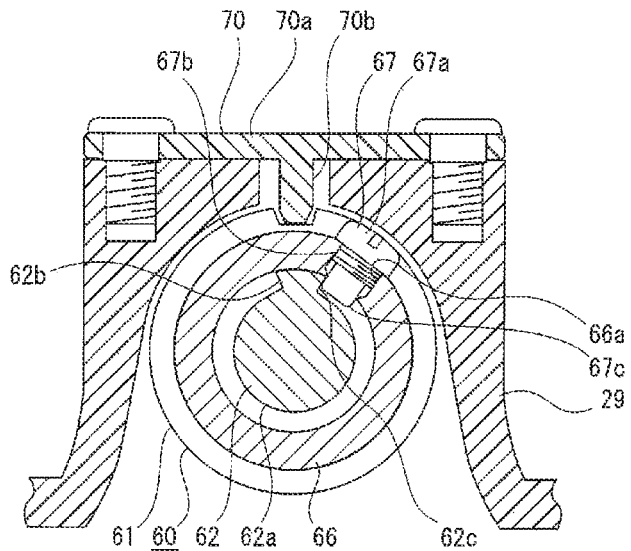
FIG. 21 is an enlarged cross-sectional diagram illustrating a state in which the stopper screw is pressed by a regulation edge and the slide ring and the stopper screw rotate integrally with the driving cam, subsequent to FIG. 20.
Figure 22:
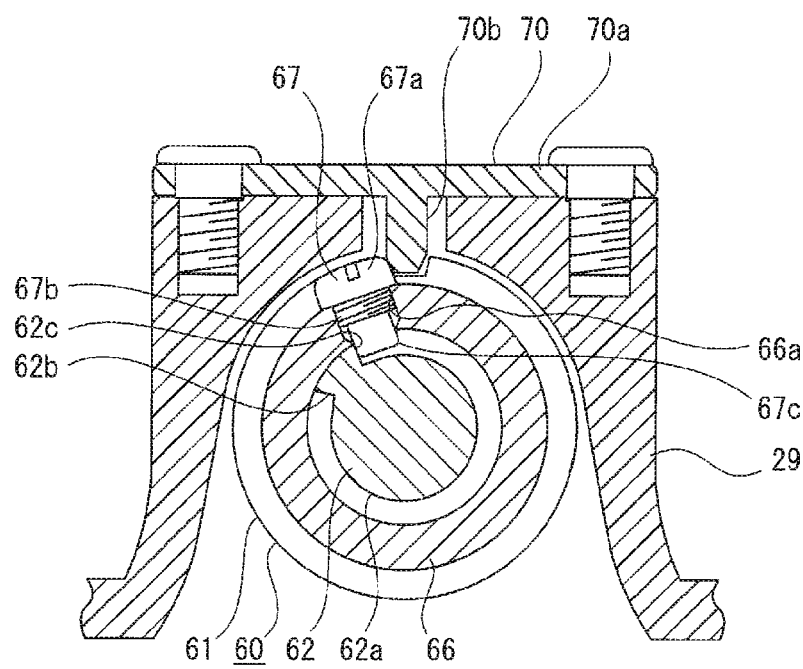
FIG. 22 is an enlarged cross-sectional diagram illustrating a state in which the stopper screw pressed by the regulation edge is in contact with the regulation pin to regulate rotation of the driving cam 60, and thus the driving cam reaches a rotation end on the other side, subsequent to FIG. 21.

When the driving cam 60 is further rotated, the slide shaft 67c of the stopper screw 67 is pressed by the second regulation edge 62c of the slide groove 62a, and thus the slide ring 66 and the stopper screw 67 are integrated with the driving cam 60 and rotated, and the stopper screw 67 is gradually separated from the regulation pin 70b (refer to FIG. 21). At this time, the driving cam 60 is rotated one or more rounds from the one rotation end.

When the driving cam 60 is continuously rotated in integration with the slide ring 66 and the stopper screw 67, the head 67a of the stopper screw 67 that has been pressed by the second regulation edge 62c comes in contact with the regulation pin 70b (refer to FIG. 22), thereby regulating the rotation of the driving cam 60, and reaches the other rotation end. At this time, the driving cam 60 has been rotated about two rounds from the one rotation end.

On the other hand, when the driving cam 60 is rotated in the state in which the driving cam 60 is positioned at the other rotation end, the second regulation edge 62c is separated from the stopper screw 67 and the slide shaft 67c moves with respect to the slide groove 62a. When the driving cam 60 is further rotated, the slide shaft 67c is pressed by the first regulation edge 62b, the slide ring 66 and the stopper screw 67 are integrated with the driving cam 60 and rotated, and thereby the head 67a of the stopper screw 67 pressed by the first regulation edge 62b is brought into contact with the regulation pin 70b, the rotation of the driving cam 60 is regulated, and the driving cam reaches the one rotation end. At this time, the driving cam 60 has been rotated about two rounds from the other rotation end.

Since the slide ring 66 assembled with the stopper screw 67 is supported by the driving cam 60 as described above, the driving cam 60 can be rotated more than one round even in the configuration in which rotation of the driving cam 60 is regulated. Thus, a large amount of rotation of the driving cam 60 is secured after the rotation of the driving cam 60 is regulated, an amount of movement of the second lens groups 33 and 33 and the third lens groups 39 and 39 which are zoom lens groups in the optical axis direction is increased, and thereby the variable magnification function can be improved.

In addition, since the large amount of rotation of the driving cam 60 can be secured, the amount of movement of the second lens groups 33 and 33 and the third lens groups 39 and 39 in the optical axis direction can be increased without lengthening the driving cam 60, and thus miniaturization of the medical observation device 1 in the optical axis direction can be achieved.

Note that the example in which the driving cam 60 is rotated first with respect to the slide ring 66, the stopper screw 67 is then pressed by a part of the driving cam 60, and the slide ring 66 and the stopper screw 67 are integrated with the driving cam 60 and rotated has been described above. However, a configuration in which, when rotation of the driving cam 60 is started in the medical observation device 1, the driving cam 60 and the slide ring 66 are integrated and rotated first, the head 67a of the stopper screw 67 is brought into contact with the regulation pin 70b to stop the rotation of the slide ring 66, and then the driving cam 60 is continuously rotated with respect to the slide ring 66 is also possible.

A gear box 71 is mounted on one side of the rear end part of the intermediate support housing 29 (refer to FIG. 4). The gear box 71 has a gear case 72 that opens sideward and upward and a gear cover 73 that closes the openings of the gear case 72 (refer to FIGS. 4, 23, 24 and 25).

Figure 26:
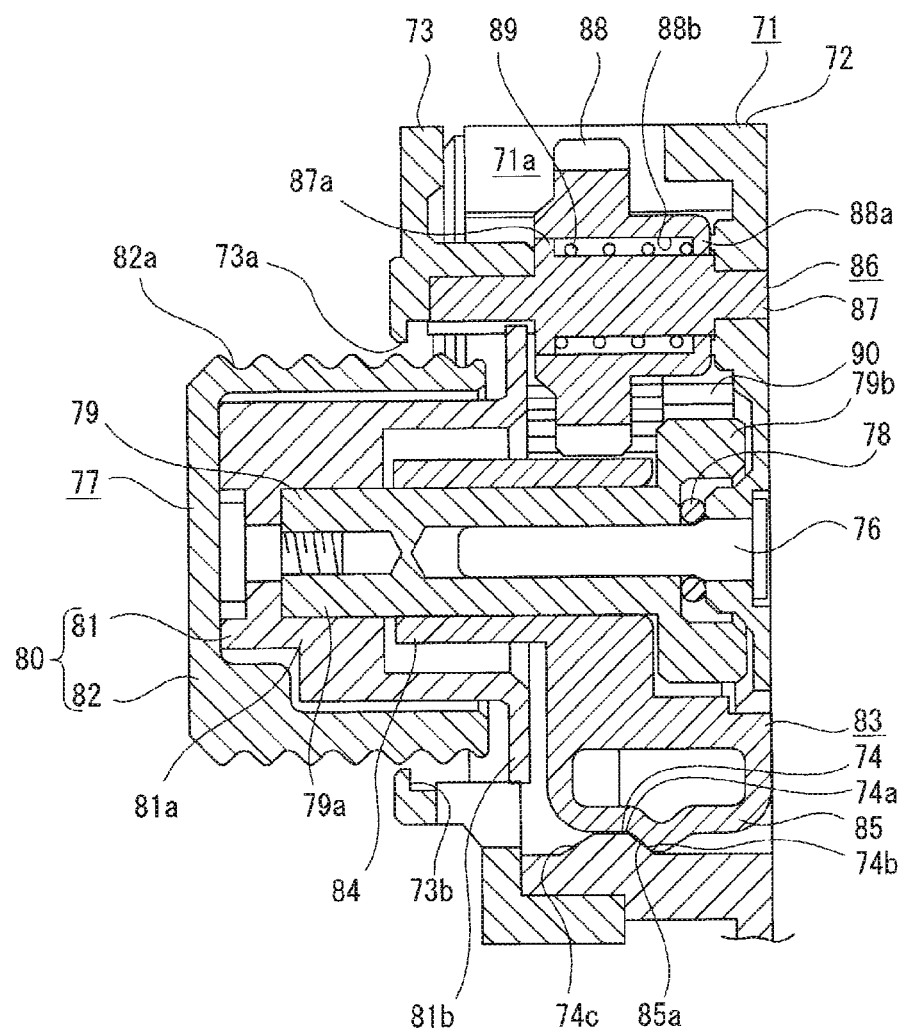
FIG. 26 is an enlarged cross-sectional diagram illustrating the gear box and the respective parts disposed in the gear box, and a state in which a manual manipulation knob is at a first position and a switch gear is at a non-meshing position.

A holding protrusion part 74 that protrudes inward is provided on an inner face of the gear case 72 (refer to FIG. 26). The holding protrusion part 74 is formed with a plane part 74a facing upward, a first holding engagement part 74b that is connected to one end of the plane part 74a in the left-right direction and displaced further downward as it runs deeper into the gear case 72, and a second holding engagement part 74c that is connected to the other end of the plane part 74a in the left-right direction and displaced further downward as it runs further into an opening side of the gear case 72.

Figure 25:
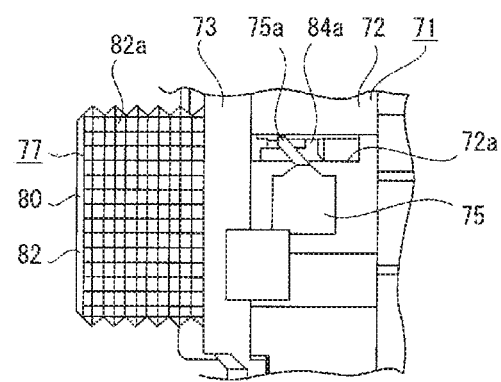

A manipulation hole 72a is formed in a lower end part of the gear case 72 (refer to FIG. 25). A detection switch 75 is mounted in the bottom of the gear case 72, and thus the detection switch 75 is positioned near the manipulation hole 72a. The detection switch 75 has a switch piece 75a, and the switch piece 75a is positioned across the manipulation hole 72a.

A knob insertion hole 73a that is penetrated to the left and right is formed in the gear cover 73 (refer to FIG. 26). The opening edge of the knob insertion hole 73a is provided in the gear cover 73 as a flange-shaped movement regulation part 73*b* jutting out on the inner circumference side.

A fulcrum shaft 76 is mounted on a surface of a deep side of the gear case 72 in the left-right direction. The fulcrum shaft 76 has one end stretching in the left-right direction mounted on the surface of the deep side of the gear case 72.

The fulcrum shaft 76 supports a manipulation object 77. An O-ring 78 is mounted at a position near one end of the fulcrum shaft 76.

The manipulation object 77 has a supported gear 79 and a manual manipulation knob 80 mounted in one end of the supported gear 79.

The supported gear 79 integrates a connection shaft 79*a* that is supported by the fulcrum shaft 76 and stretches in the left-right direction and a switch gear 79*b* jutting outward from an end of the connection shaft 79*a* in the axial direction.

The manipulation object 77 can rotate with respect to the fulcrum shaft 76 in the axial rotation direction of the fulcrum shaft 76, and can move with respect to the fulcrum shaft 76 in the axial direction of the fulcrum shaft 76.

The manual manipulation knob 80 has a knob base 81 mounted on the supported gear 79, and a manipulation cap 82 that is mounted on the knob base 81 and covers the knob base 81 from the outside. At least a part of the manual manipulation knob 80 protrudes sideward from one insertion hole formed in the outer circumference part 8 of the outer housing 2 (refer to FIG. 2).

The knob base 81 has a mounted part 81*a* mounted by being screwed into the supported gear 79 or the like, covering substantially a half of the supported gear 79, and a flange-shaped regulated part 81*b* jutting outward from an end of the mounted part 81*a* in the axial direction (refer to FIG. 26).

The manipulation cap 82 is mounted on the knob base 81, covering the mounted part 81*a*. In the state in which the manipulation cap 82 is mounted on the knob base 81, the outer circumference part of the regulated part 81*b* is positioned on the outer side of the outer circumferential face of the manipulation cap 82. The outer circumferential face of the manipulation cap 82 is formed as a knob surface 82*a* processed in a predetermined shape through knurling processing or the like. The manipulation object 77 is manually rotated as the knob surface 82*a* of the manipulation cap 82 is gripped. Thus, by forming the knob surface 82*a* processed through knurling processing or the like in the manipulation cap 82, a satisfactory manipulation property of the manipulation object 77 can be ensured.

The manual manipulation knob 80 can move between a first position that is a movement end of the direction in which it is accommodated in the gear box 71 and a second position that is a movement end of the direction in which it is drawn out from the gear box 71. In addition, the supported gear 79 is integrated with the knob base 81 and the manipulation cap 82 and moved, and the switch gear 79*b* is moved to a non-meshing position when the manual manipulation knob 80 is moved to the first position, and moved to a meshing position when the manual manipulation knob 80 is moved to the second position.

A holding member 83 is supported by the supported gear 79 of the manipulation object 77 in an externally fitted manner. The holding member 83 can rotate with respect to the supported gear 79 in the direction around the axis but is not able to move in the axial rotation direction of the supported gear 79, and thus does not rotate along with the supported gear 79 according to rotation in the axial rotation direction of the manipulation object 77, but moves integrally with the supported gear 79 according to movement in the axial direction of the manipulation object 77.

The holding member 83 has a tubular part 84 supported by the supported gear 79 in an externally fitted manner and a connection protrusion part 85 that protrudes from the tubular part 84 in the radial direction (outward). A manipulation protrusion part 84*a* that protrudes outward is provided in the tubular part (refer to FIG. 25). The leading end part of the manipulation protrusion part 84*a* inserted into the manipulation hole 72*a* formed in the gear case 72 protrudes outward from the manipulation hole 72*a*. A convex position holding part 85*a* is provided on an outer side of the connection protrusion part 85, and the position holding part 85*a* can be elastically deformed in a direction in which it is separated from or comes in contact with the tubular part 84 (refer to FIG. 26).

The manipulation object 77 configured as described above is configured such that the manual manipulation knob 80 is inserted into the knob insertion hole 73*a* of the gear cover 73 and a part thereof on the manual manipulation knob 80 side is positioned outside the gear box 71. The regulated part 81*b* of the knob base 81 is in a state in which it is positioned inside the gear box 71 and thus can come in contact with the movement regulation part 73*b* provided in the gear cover 73.

The transmission gear 86 is supported inside the gear box 71 to be freely rotatable. The transmission gear 86 has a gear shaft 87 that stretches in the left-right direction and a movement gear 88 that is rotated around the gear shaft 87.

An end of the gear shaft 87 in the axial direction is mounted on the surface on the deep side of the gear case 72 in the left-right direction, and the other end thereof in the axial direction is mounted on a part of the gear cover 73. A flange-shaped reception protrusion part 87*a* jutting outward from an intermediate part of the gear shaft 87 in the axial direction is provided.

A flange-shaped reception part 88*a* jutting inward is provided at one end of the movement gear 88 in the axial direction. The movement gear 88 can rotate with respect to the gear shaft 87 in the axial direction of the gear shaft 87. Thus, a movement space 71*a* that allows movement of the movement gear 88 in the axial direction of the gear shaft 87 is formed inside the gear box 71.

A meshing assisting spring 89 that is a compression coil spring is disposed in a center hole 88*b* of the movement gear 88, and the meshing assisting spring 89 is disposed in a compressed state between the reception protrusion part 87*a* of the gear shaft 87 and the reception part 88*a* of the movement gear 88. Thus, the meshing assisting spring 89 applies an urging force to the movement gear 88 in the direction opposite to the gear cover 73.

Figure 23:
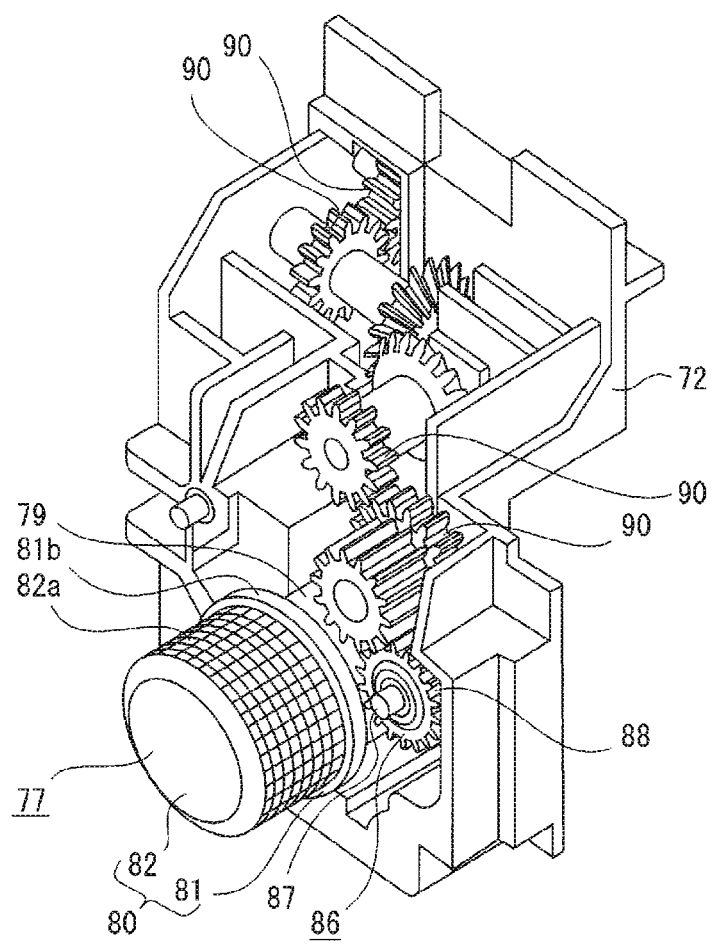
FIG. 23 is an enlarged perspective diagram illustrating a gear box and respective parts disposed in the gear box.
Figure 24:
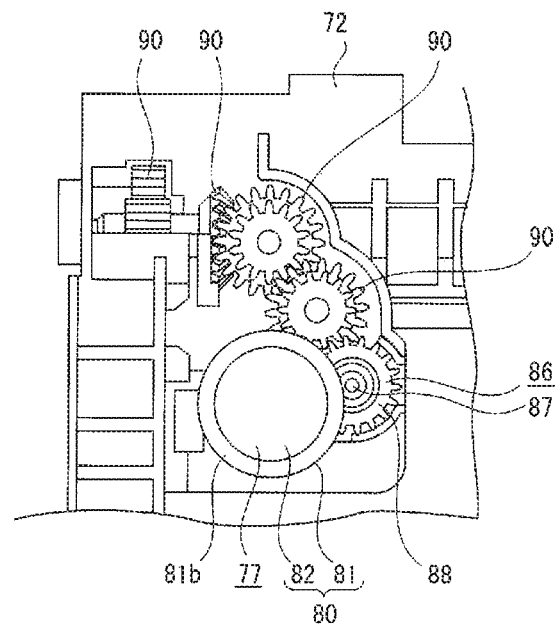
FIG. 24 is an enlarged side diagram illustrating the gear box and respective parts disposed in the gear box.

A plurality of interlocked gears 90, 90, . . . are supported to be freely rotatable inside the gear box 71 (refer to FIGS. 23 and 24). The interlocked gears 90, 90, . . . have a function of transmitting a driving force manually produced when the manipulation cap 82 is manipulated along with the transmission gear 86 to the driving cam 60, and at least some of them function also as deceleration gears. The interlocked gear 90 positioned closest to the transmission gear 86 meshes with the movement gear 88, and the interlocked gear 90 positioned closest to the driving cam 60 meshes with the gear member 68 mounted in the driving cam 60.

In the state in which the manual manipulation knob 80 is at the first position and the switch gear 79*b* of the supported gear 79 is at the non-meshing position, the switch gear 79*b* does not mesh with the movement gear 88 as illustrated in FIG. 26. At this moment, the position holding part 85*a* of the holding member 83 meshes with a first holding engagement part 74*b* provided in the gear case 72 to cause the manipulation object 77 to be positioned with respect to the gear box 71, and thus the manual manipulation knob 80 is held at the first position, and the switch gear 79*b* is held at the non-meshing position.

The driving cam 60 is rotated by a driving force of the driving motor 56 when the switch gear 79*b* is at the non-meshing position, the second lens groups 33 and 33 and the third lens groups 39 and 39 are moved by electromotive driving, and thus zooming is performed. At this moment, the switch gear 79*b* does not mesh with the movement gear 88, and thus a driving force of the driving motor 56 is not transmitted to the switch gear 79*b*, and therefore the manipulation object 77 is not rotated.

On the other hand, when it is not possible to perform electromotive driving because the driving motor 56 has a problem or the like, the operator 700 or the like grips the manipulation cap 82 to move the manipulation object 77 in the direction in which it is drawn out from the gear box 71, and thus manual zooming can be performed as follows.

Figure 27:
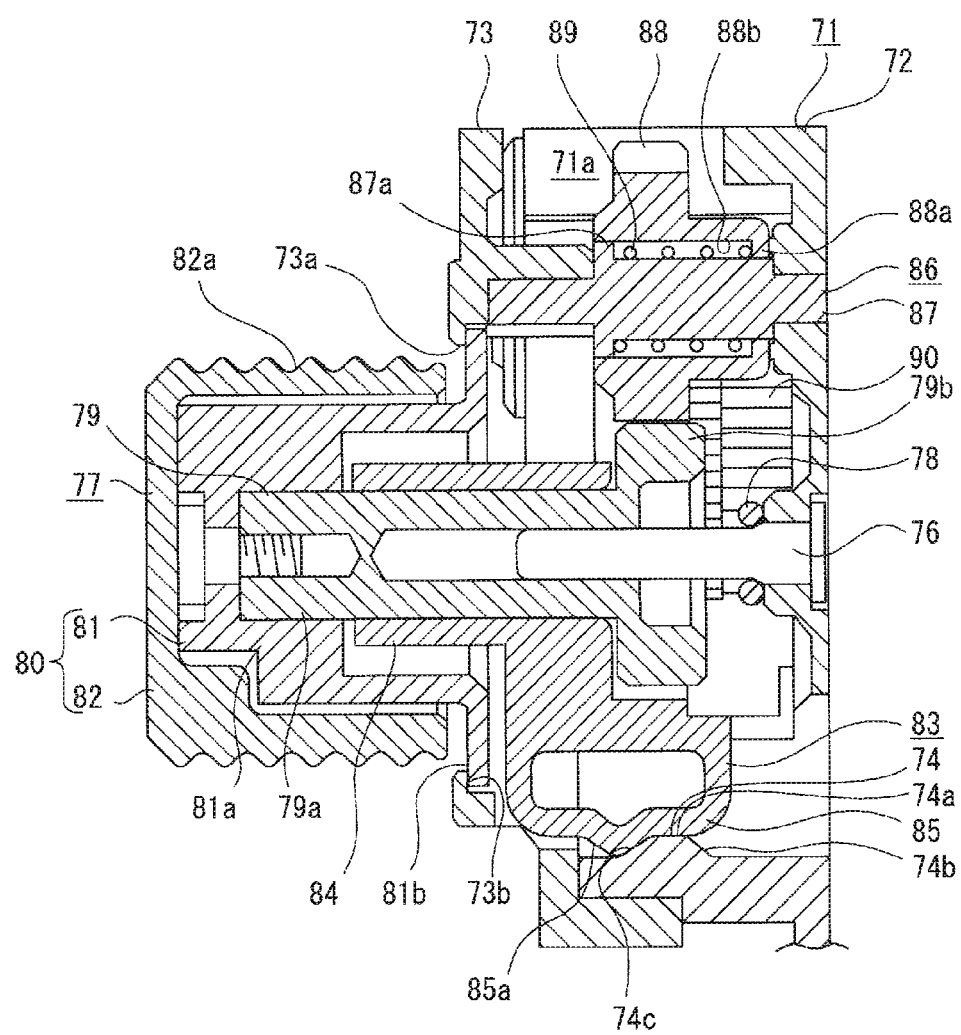
FIG. 27 is an enlarged cross-sectional diagram illustrating the gear box and the respective parts disposed in the gear box, and a state in which the manual manipulation knob is at a second position and the switch gear is at a meshing position.
Figure 28:
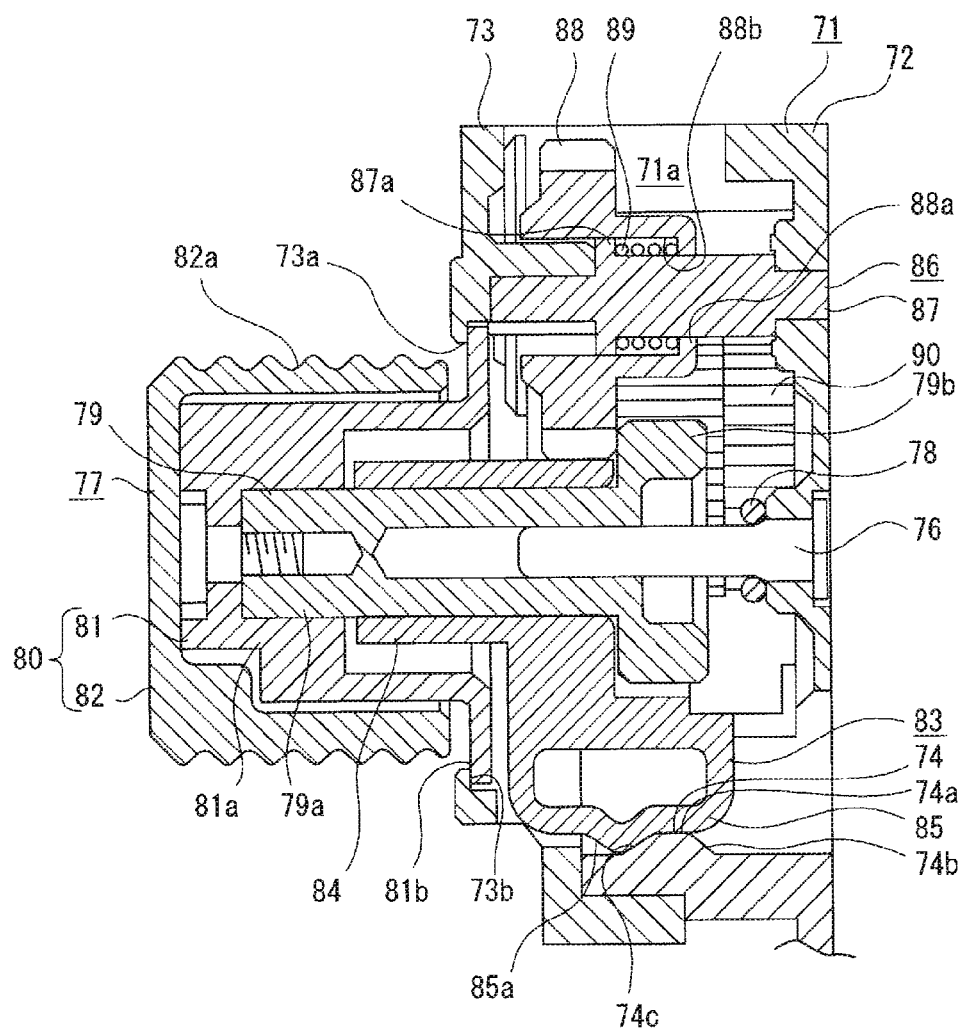
FIG. 28 is an enlarged cross-sectional diagram illustrating the gear box and the respective parts disposed in the gear box, and a state in which the manual manipulation knob is moved to the second position and the switch gear does not mesh with a transmission gear.

When the manipulation cap 82 is gripped to move the manipulation object 77 in the direction in which it is drawn out from the gear box 71, the switch gear 79*b* reaches the meshing position and thus meshes with the movement gear 88 (refer to FIG. 27). At this moment, the position holding part 85*a* of the holding member 83 is elastically deformed during its movement, and then elastically restored after it moves onto the plane part 74*a* from the first holding engagement part 74*b*, and meshes with the second holding engagement part 74*c*. Thus, the manipulation object 77 is positioned with respect to the gear box 71 such that the manual manipulation knob 80 is held at the second position, and the switch gear 79*b* is held at the meshing position.

When the manual manipulation knob 80 is moved from the first position to the second position, the holding member 83 is moved according to the movement of the manipulation object 77, and the switch piece 75*a* of the detection switch 75 is manipulated by the manipulation protrusion part 84*a*. When the switch piece 75*a* is manipulated, the driving motor 56 is in a non-driving state in which driving is not performed.

In addition, when the manual manipulation knob 80 is moved toward the second position from the first position, the regulated part 81*b* can be brought into contact with the movement regulation part 73*b*, and thus movement of the manual manipulation knob 80 with respect to the gear box 71 is regulated when the regulated part 81*b* is brought into contact with the movement regulation part 73*b*.

When the position holding part 85*a* of the holding member 83 is engaged with the second holding engagement part 74*c* from the plane part 74*a*, a feeling of a change in an engagement position is transmitted to the hand in which the manipulation cap 82 is gripped, and thus the operator 700 or the like experiences a so-called click feeling.

Thus, the engagement state of the position holding part 85*a* with the second holding engagement part 74*c* is recognized due to the size of a load transmitted to the manipulation cap 82 via the holding member 83 during the movement of the manual manipulation knob 80, the operator 700 or the like can easily recognize that a draw-out manipulation of the manipulation object 77 has been completed, and thus the draw-out manipulation of the manipulation object 77 can be easily and reliably performed and the switch gear 79*b* can be reliably moved to the meshing position.

When the manual manipulation knob 80 is rotated in the state in which the knob surface 82*a* of the manipulation cap 82 is gripped after the draw-out manipulation of the manipulation object 77 is completed, a driving force generated through manual manipulation is transmitted from the switch gear 79*b* to the driving cam 60 via the transmission gear 86, the interlocked gears 90, 90, . . . , and the gear member 68, the second lens groups 33 and 33 and the third lens groups 39 and 39 are moved due to the manual operation, and thus zooming is performed. Thus, the transmission gear 86, the interlocked gears 90, 90, . . . , the gear member 68, and the driving cam 60 function as a driving force transmission mechanism that transmits driving forces to the first zoom lens holding frame 32, the second lens groups 33 and 33, the second zoom lens holding frame 34, and the third lens groups 39 and 39 that function as a moving object.

At this movement, the driving motor 56 is rotated according to the rotation of the driving cam 60, and thus a load caused by the rotation of the driving motor 56 is exerted on the operator 700 or the like. Thus, it is desirable to use a component that has a torque that causes an optimum load exerted on the operator 700 during manipulation of the manual manipulation knob 80 as the driving motor 56.

Note that, when the draw-out manipulation of the manipulation object 77 is performed, there is a possibility of an end face of the switch gear 79*b* coming in contact with an end face of the movement gear 88 when the manipulation object 77 is moved, resulting in the switch gear 79*b* not meshing with the movement gear 88, according to a phase of the gear teeth of the switch gear 79*b* and a phase of the gear teeth of the movement gear 88. In this case, the movement gear 88 is pressed by the switch gear 79*b* according to movement of the supported gear 79, the movement gear 88 is moved in the movement space 71*a* according to the movement of the supported gear 79 (refer to FIG. 28).

When the movement gear 88 is moved in the movement space 71*a*, the meshing assisting spring 89 disposed in the center hole 88*b* of the movement gear 88 is compressed, and thus an urging force of the meshing assisting spring 89 exerted on the movement gear 88 in the direction opposite to the gear cover 73 increases.

When the manual manipulation knob 80 is rotated in the state in which the movement gear 88 is moved according to the movement of the supported gear 79, the supported gear 79 is rotated with respect to the movement gear 88 along with the manual manipulation knob 80, the phase of the gear teeth of the switch gear 79*b* and the phase of the gear teeth of the movement gear 88 are thus in a different state from the previous phases, the movement gear 88 is moved in the direction opposite to the gear cover 73 due to the urging force of the meshing assisting spring 89, and thereby the switch gear 79*b* meshes with the movement gear 88. Then, zooming is performed by manually manipulating the manual manipulation knob 80 to continuously rotate and thus the second lens groups 33 and 33 and the third lens groups 39 and 39 to move.

As described above, since the medical observation device 1 has the meshing assisting spring 89 which urges the transmission gear 86 in a direction to bring it close to the switch gear 79*b* in the axial direction, even when the manual manipulation knob 80 is moved from the first position to the second position and thus the transmission gear 86 is pressed and moved by the switch gear 79*b*, the meshing assisting spring 89 causes the transmission gear 86 to move in the direction to get close to the switch gear 79*b* through the rotation manipulation of the manual manipulation knob 80, and then the gears mesh with each other.

Therefore, even when the switch gear 79*b* and the transmission gear 86 do not mesh with each other when the manual manipulation knob 80 moves from the first position to the second position, it is possible to cause the components to reliably mesh with each other, and thereby enhance reliability in operations.

Meanwhile, when the manipulation cap 82 is pressed into the gear box 71 side in the state in which the manual manipulation knob 80 is drawn out from the gear box 71 and thus is at the second position, the manipulation object 77 is moved in the direction in which it is accommodated in the gear box 71.

When the manipulation object 77 is moved in the direction in which it is accommodated in the gear box 71, the position holding part 85a of the holding member 83 is elastically deformed during the movement, elastically restored after it moves onto the plane part 74a from the second holding engagement part 74c, and meshes with the first holding engagement part 74b. Thus, the manipulation object 77 is positioned with respect to the gear box 71 such that the manual manipulation knob 80 is held at the second position, and the switch gear 79b is held at the non-meshing position.

When the manual manipulation knob 80 is moved from the second position to the first position, the holding member 83 is moved according to the movement of the manipulation object 77, and the switch piece 75a of the detection switch 75 is manipulated by the manipulation protrusion part 84a. When the switch piece 75a is manipulated, the driving motor 56 is in a driving state in which driving is possible.

When the position holding part 85a of the holding member 83 is engaged with the first holding engagement part 74b from the plane part 74a, a feeling of a change in an engagement position is transmitted to the hand in which the manipulation cap 82 is gripped, and thus the operator 700 or the like experiences a so-called click feeling.

Thus, the engagement state of the position holding part 85a with the first holding engagement part 74b is recognized due to the size of a load transmitted to the manipulation cap 82 via the holding member 83 during the movement of the manual manipulation knob 80, the operator 700 or the like can easily recognize that the pressing manipulation of the manipulation object 77 has been completed, and thus the pressing manipulation of the manipulation object 77 can be easily and reliably performed and the switch gear 79b can be reliably moved to the non-meshing position.

In addition, in the medical observation device 1, the manual manipulation knob 80 which can be manipulated to rotate in the axial rotation direction of the fulcrum shaft 76 and can be moved between the first position and the second position is provided, meshing of the switch gear 79b and the transmission gear 86 is released at the non-meshing position, and the switch gear 79b and the transmission gear 86 mesh with each other at the meshing position.

Therefore, even in a state in which the manual manipulation knob 80 is not rotated during electromotive driving using the driving motor 56 and electromotive driving of the second lens groups 33 and 33 and the third lens groups 39 and 39 serving as moving objects is not possible, the moving objects can be moved through manual manipulation and it is possible to prevent inconvenience from occurring during medical procedures, without causing them to be entwined with the protection sheet 300 known as a drape during the electromotive driving.

Furthermore, when the switch gear 79b is moved to the meshing position, the driving motor 56 is set to be in a non-driving state, it is possible to prevent obstruction of manual manipulation to rotate the manual manipulation knob 80 when the manual manipulation knob 80 is manipulated to rotate, without causing the transmission gear 86 to rotate due to driving of the driving motor 56.

Furthermore, the direction from the first position to the second position is set as the direction in which the manual manipulation knob 80 is drawn out from the gear box 71.

Thus, the manual manipulation knob 80 is manually manipulated in the state in which the manual manipulation knob 80 has been drawn out from the gear box 71, the area of a portion of the manual manipulation knob 80 gripped by fingers becomes large, and thus it is possible to ensure a satisfactory manipulation property of the manual manipulation knob 80.

In addition, in the medical observation device 1, when the manual manipulation knob 80 is moved to the first position, the position holding part 85a of the holding member 83 is engaged with the first holding engagement part 74b of the gear box 71 and thus the switch gear 79b is held at the non-meshing position, and when the manual manipulation knob 80 is moved to the second position, the position holding part 85a is engaged with the second holding engagement part 74c and thus the switch gear 79b is held at the meshing position.

Thus, since the first holding engagement part 74b and the second holding engagement part 74c are provided in the gear box 71, the gear box 71 has the function of disposing each gear such as the switch gear 79b or the transmission gear 86 and the function of holding the switch gear 79b at the meshing position and the non-meshing position, and therefore the switch gear 79b can be reliably held at the meshing position and the non-meshing position without causing an increase in the number of components.

In addition, the movement regulation part 73b is provided in the gear box 71, and the regulated part 81b that can be brought into contact with the movement regulation part 73b is provided in the manual manipulation knob 80.

Thus, movement of the manual manipulation knob 80 with respect to the gear box 71 is regulated if the regulated part 81b is brought into contact with the movement regulation part 73b when the manual manipulation knob 80 is moved from the first position to the second position, which leads to regulation of more movement of the manual manipulation knob 80 than necessary, and thus exfoliation of the manual manipulation knob 80 from the gear box 71 can be prevented.

Note that, since the medical observation device 1 is covered by the protection sheet 300 when used during medical procedures, the manual manipulation knob 80 may be manually manipulated to rotate from the outside of the protection sheet 300 in the state in which the protection sheet 300 overlaps the manual manipulation knob 80 and thus they are gripped together.

Therefore, in order to ensure a satisfactory manipulation property, a configuration in which, for example, a manipulation mechanism having a manipulation unit with which manual manipulation can be performed at a different position from the manual manipulation knob 80 is connected to the manual manipulation knob 80, and the manual manipulation knob 80 is rotated by manually manipulating the manipulation unit is possible.

<Configuration of Rear Barrel Section>

Next, a configuration of the rear barrel section 13 will be described (with reference to FIGS. 3, 4, and 5, and FIGS. 29 to 55).

The rear barrel section 13 has a rear support housing 91 and respective necessary parts mounted or supported inside and outside of the rear support housing 91 (refer to FIGS. 3 to 5). The rear barrel section 13 is disposed inside the main body 3 of the outer housing 2 excluding at least a part of a manipulation lever to be described below.

Figure 29:
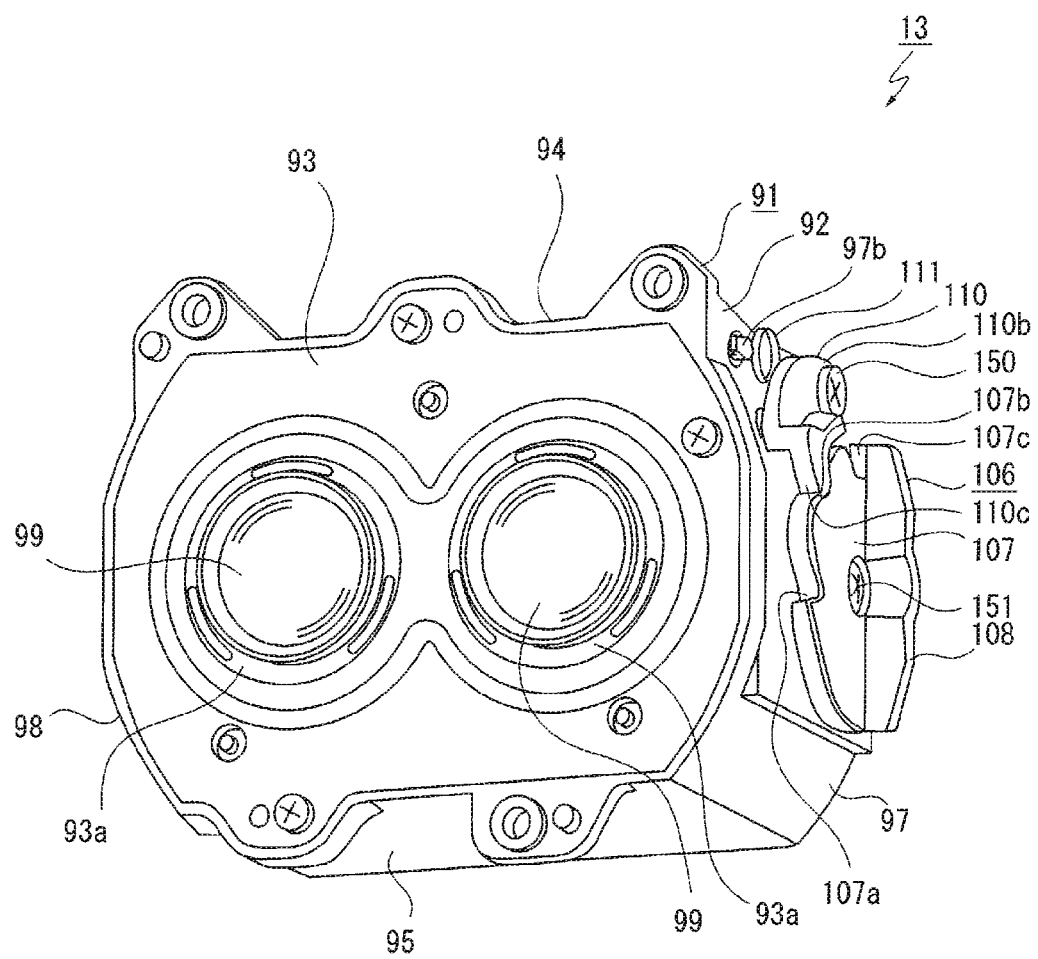
FIG. 29 is an enlarged perspective diagram of a rear barrel section.
Figure 30:
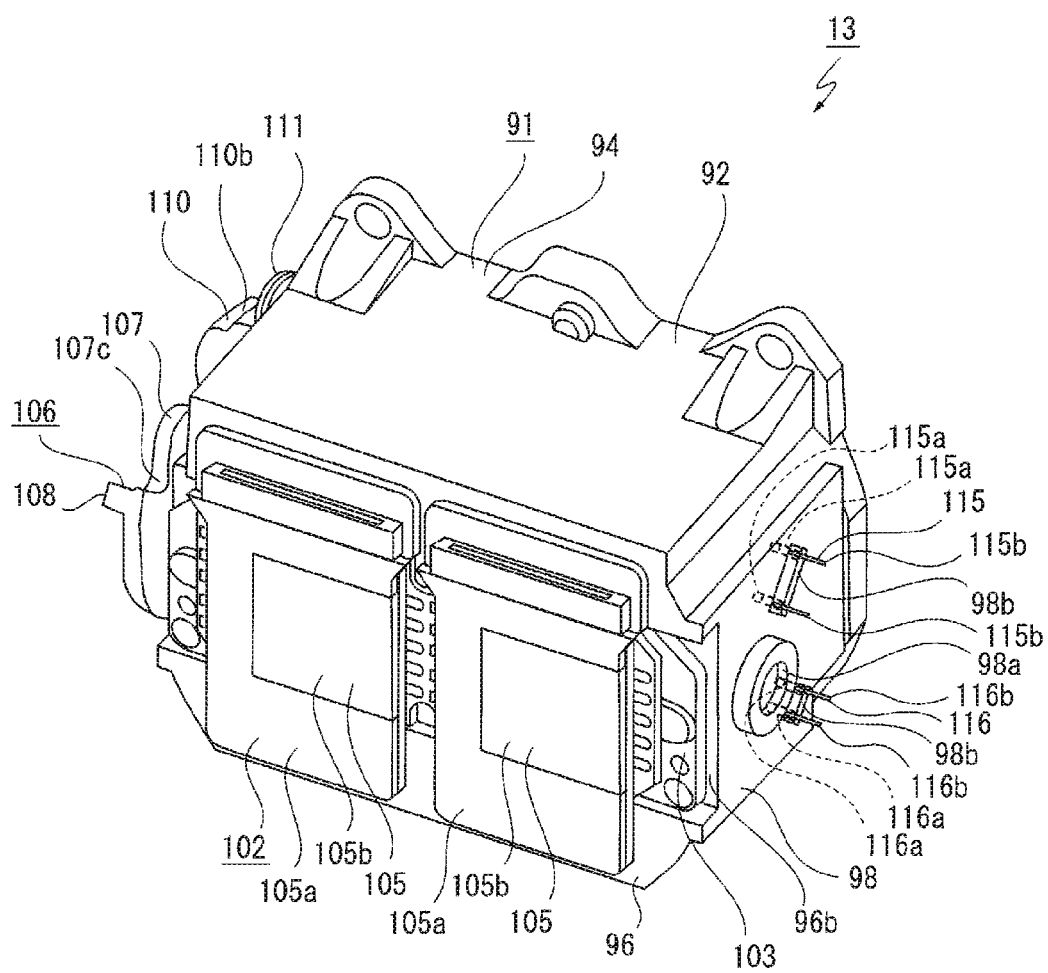
FIG. 30 is an enlarged perspective diagram of the rear barrel section viewed in a different direction from FIG. 29.
Figure 31:
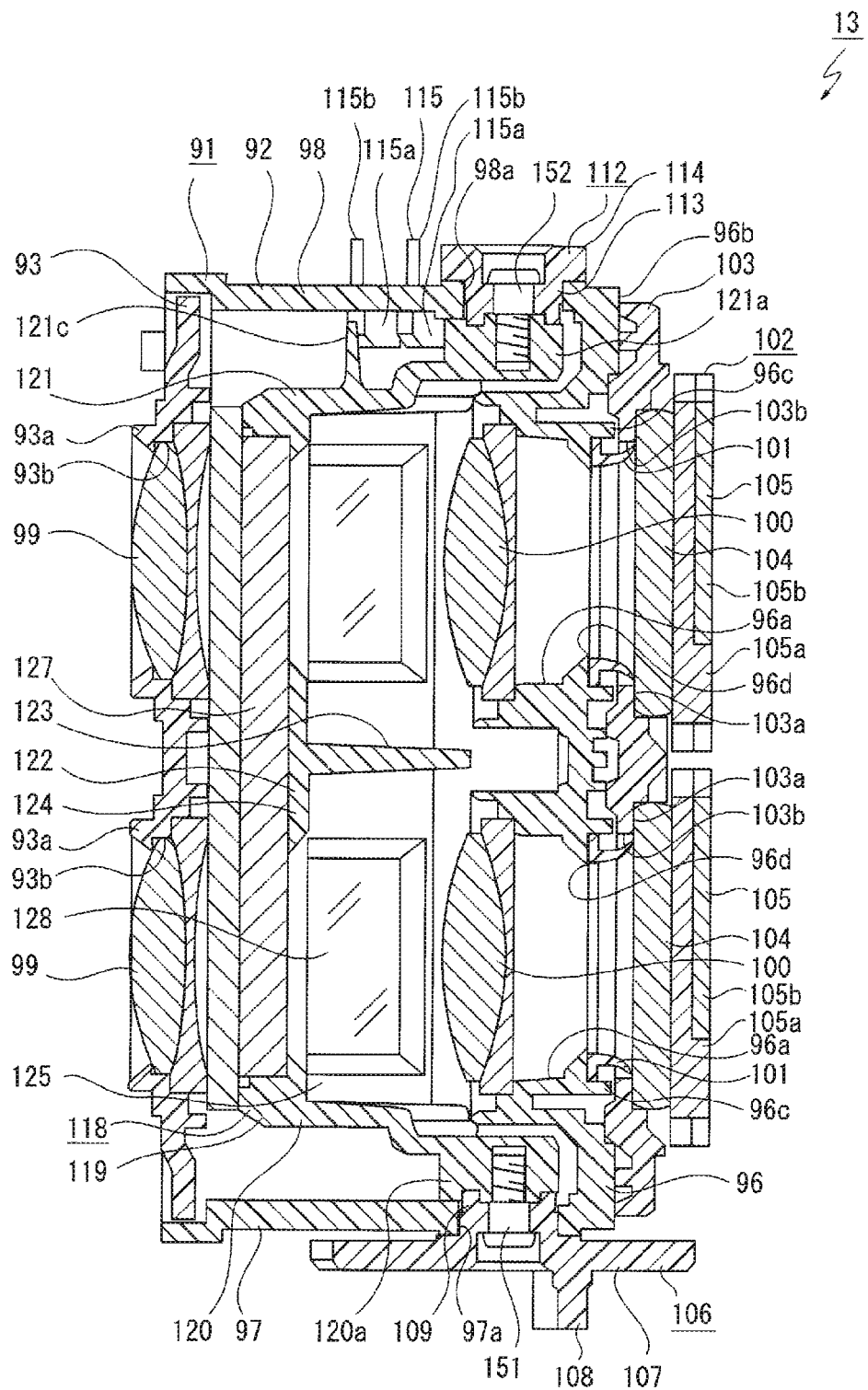
FIG. 31 is an enlarged cross-sectional diagram of the rear barrel section.

The rear support housing 91 has a box-shaped case body 92 that opens forward and a cover body 93 that closes the opening of the case body 92 (refer to FIG. 29 to FIG. 31). The rear support housing 91 is mounted in the rear face part 29b of the intermediate support housing 29 from behind using a fastening screw, or the like.

Figure 32:
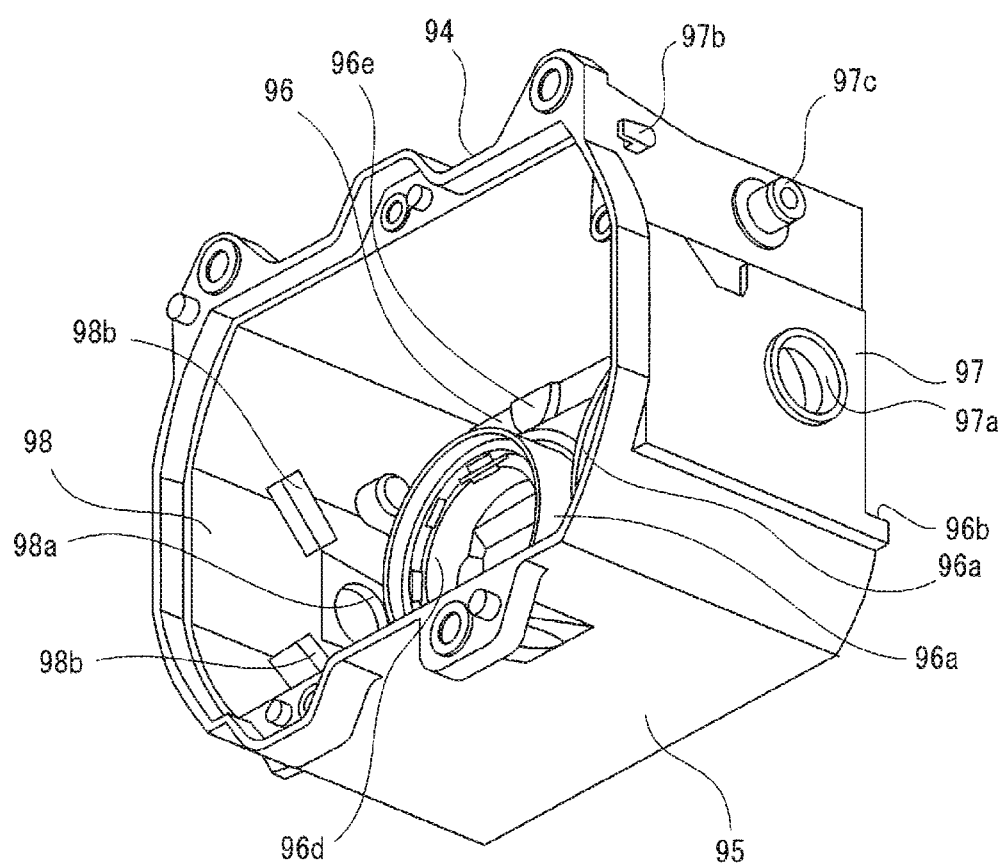
FIG. 32 is an enlarged perspective diagram illustrating the case body of a rear support housing.
Figure 33:
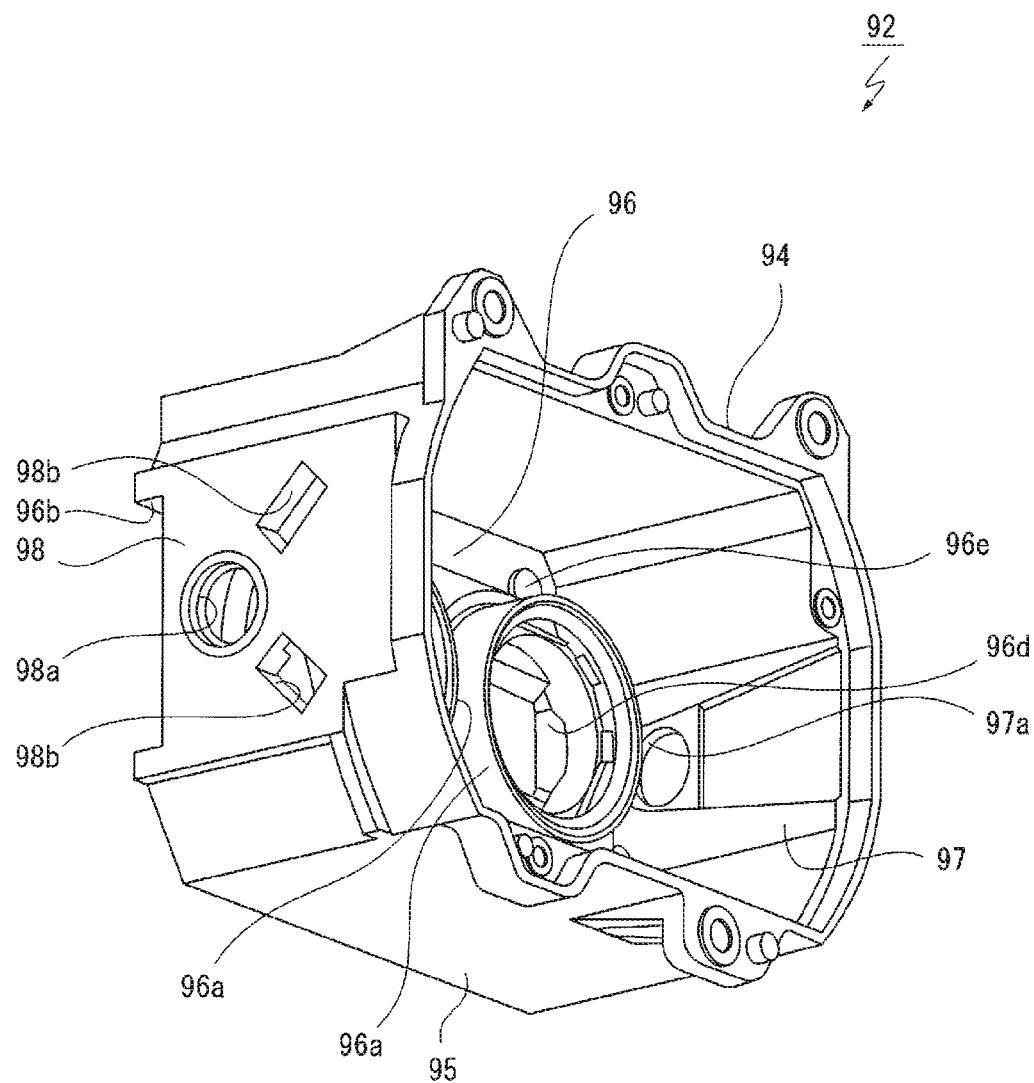
FIG. 33 is an enlarged perspective diagram illustrating the case body of the rear support housing viewed in a different direction from FIG. 32.
Figure 34:
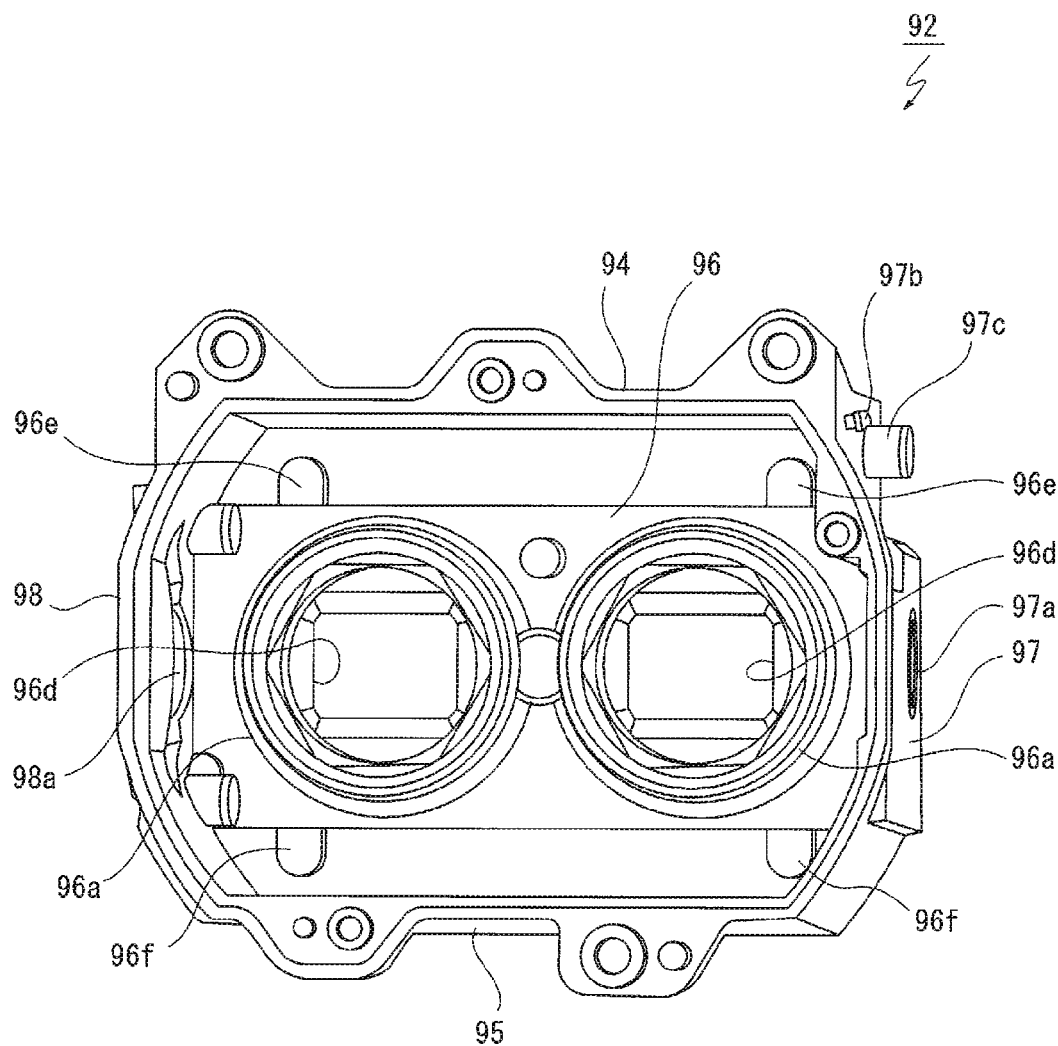
FIG. 34 is an enlarged perspective diagram illustrating the case body of the rear support housing viewed in a different direction from FIGS. 32 and 33.
Figure 35:
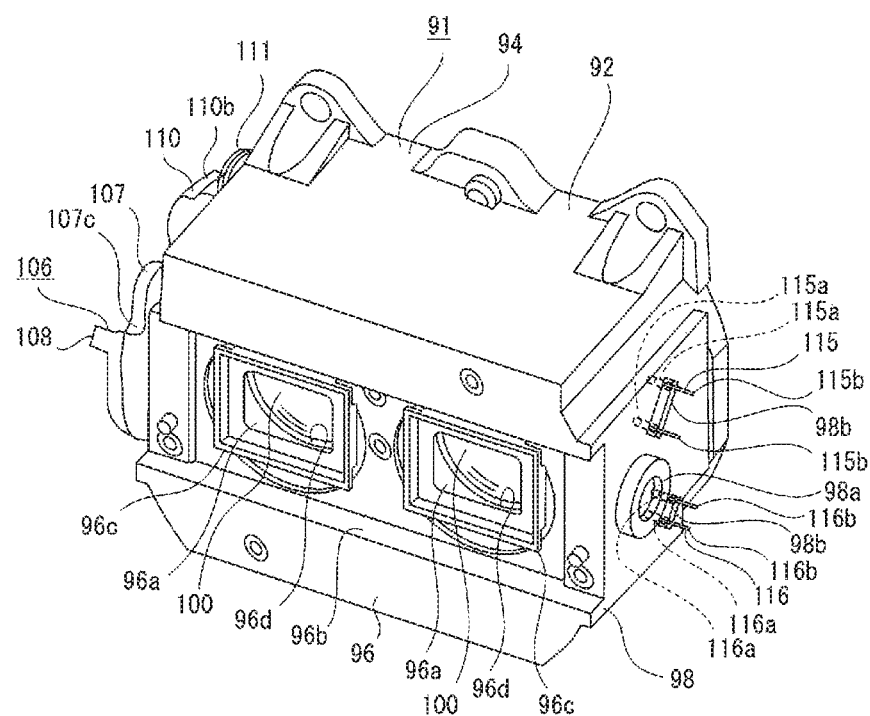
FIG. 35 is an enlarged perspective diagram illustrating the rear barrel section from which a seal member and an element unit are removed.

The case body 92 has an upper face part 94, a lower face part 95, a rear face part 96, a left side face part 97, and a right side face part 98, and is formed in a shape that extends horizontally with the width in the left-right direction slightly longer than the width in the upper-lower direction (refer to FIGS. 32 to 34).

Lens frame parts 96a and 96a formed in a circular frame shape are provided on the left and right in the front face of the rear face part 96. The rear face part 96 has upper and lower end parts positioned further backward than parts other than the upper and lower end parts, and a shallow concave part 96b that opens rearward is formed in the parts other than the upper and lower end parts (refer to FIG. 35). Disposition frame parts 96c and 96c formed in a rectangular shape that extends horizontally are provided on the left and right on the rear face side of the rear face part 96. Rectangular incidence windows 96d and 96d are formed on the inner side of the disposition frame parts 96c and 96c in the rear face part 96.

First stopper parts 96e and 96e are provided at positions near the upper end of the front face (inner face) of the rear face part 96, and second stopper parts 96f and 96f are provided at positions near the lower end thereof (refer to FIG. 34). The first stopper parts 96e and 96e and the second stopper parts 96f and 96f are positioned separately from each other on the left and right sides and protrude slightly forward.

A lever support hole 97a is formed in the left side face part 97 (refer to FIG. 32). A spring hook protrusion 97b and a support shaft 97c that protrude outward (sideward) are provided above the spring support hole 97a in the left side face part 97.

A cap support hole 98a is formed in the right side face part 98 (refer to FIG. 33). Terminal protrusion holes 98b and 98b are formed separately from each other on the upper and lower sides on the front side of the cap support hole 98a in the right side face part 98.

Circular lens holding parts 93a and 93a are provided in the cover body 93, separately from each other on the left and right sides (refer to FIGS. 29 and 31). Light transmissive holes 93b and 93b are formed on the inner side of the lens holding parts 93a and 93a in the cover body 93 (refer to FIG. 31). Fourth lens groups 99 and 99 are mounted in the lens holding parts 93a and 93a, and the fourth lens groups 99 and 99 are set as fixed lens groups.

Fifth lens groups 100 and 100 are mounted in the lens frame parts 96a and 96a of the rear face part 96, and the fifth lens groups 100 and 100 are set as fixed lens groups. Note that the fourth lens groups 99 and 99 and the fifth lens groups 100 and 100 are all set as fixed lens groups, and the fifth lens groups 100 and 100 may constitute a part of the fourth lens groups. In this case, both the fourth lens groups 99 and 99 and the fifth lens groups 100 and 100 function as one fourth lens group.

An element unit 102 is mounted in the rear face part 96 via seal members 101 and 101 (refer to FIGS. 30 and 31).

The seal members 101 and 101 are disposed to be inserted into the disposition frame parts 96c and 96c of the rear face part 96 (refer to FIG. 31). Each seal member 101 is formed of a material that can be elastically deformed, such as a rubber material, in a rectangular frame shape that extends horizontally.

The element unit 102 has an adaptor 103 formed in substantially a plate shape facing the front-rear direction, seal glass 104 and 104 disposed on the adaptor 103, and element modules 105 and 105 mounted on the seal glass 104 and 104 (refer to FIGS. 30 and 31).

The adaptor 103 is formed in a rectangular shape that extends substantially horizontally, disposed to be inserted into the concave part 96b of the rear face part 96, and mounted on the rear face part 96 using a fastening screw or the like. Disposition concave parts 103a and 103a that open rearward are formed on the left and right sides of the adaptor 103. Transmissive insertion holes 103b and 103b are formed on the inner side of the disposition concave parts 103a and 103a on the adaptor 103.

The rear end parts of the seal members 101 and 101 are inserted into the transmissive insertion holes 103b and 103b of the adaptor 103.

The seal glass 104 and 104 is disposed to be inserted into the disposition concave parts 103a and 103a of the adaptor 103, and their outer circumference parts are mounted on the adaptor 103 through adhesion, or the like. In the state in which the seal glass 104 and 104 is mounted on the adaptor 103, the outer circumference part of the seal glass 104 and 104 is pressed by the rear end part of the seal members 101 and 101, the rear end part of the seal members 101 and 101 is thus elastically deformed to bend outward, and thereby the rear end part of the seal members 101 and 101 tightly adheres to the front face of the seal glass 104 and 104.

Thus, it is difficult for foreign substances such as dust to infiltrate the rear support housing 91 and foreign substances such as dust to adhere to the front face of the seal glass 104 and 104, and therefore quality of images or videos captured by the medical observation device 1 can be improved.

The element module 105 is constituted of a base plate 105a and an image sensor 105b, and is configured such that the image sensor 105b is attached to the base plate 105a. The image sensor 105b has a function of photoelectrically converting a subject image captured by an imaging optical system. The front faces of the element modules 105 and 105 are mounted on the rear faces of the seal glass 104 and 104 in a tight contact state, and have a greater area than the seal glass 104 and 104.

Since the concave part 96b that opens rearward is formed in the rear face part 96 of the rear support housing 91 and the seal glass 104 and 104 of the element unit 102 is disposed in the concave part 96b as described above, the rear barrel section 13 can be thin in the optical axis direction, and therefore the medical observation device 1 can be minimized.

Figure 36:
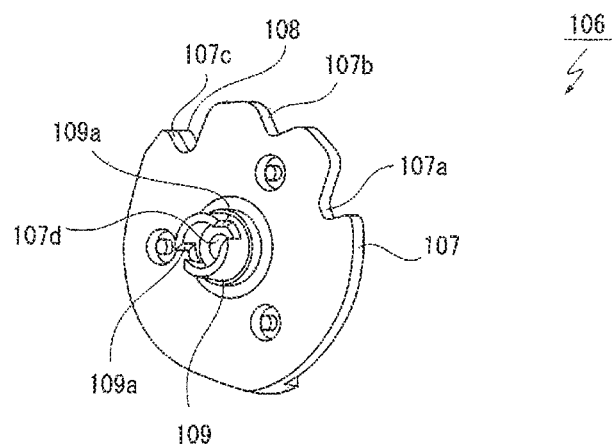
FIG. 36 is an enlarged perspective diagram of an operating lever.

A manipulation lever 106 is supported on the left side face part 97 to be freely rotatable (refer to FIGS. 3, 29 and 31). The manipulation lever 106 integrates a plate-shaped rotation plate part 107 facing in the left-right direction, a manipulation protrusion part 108 that protrudes outward (sideward) from the outer face of the rotation plate part 107, and a cylindrical part 109 that protrudes inward (sideward) from the inner face of the rotation plate part 107 as illustrated in FIGS. 29 and 36.

A first engagement concave part 107a, a second engagement concave part 107b, and a third engagement concave part 107c are formed from the front side in order in the outer circumference part of the rotation plate part 107, separately from each other in the circumferential direction. A screw insertion hole 107d is formed at substantially the center of the rotation plate part 107.

The manipulation protrusion part 108 is linearly formed, and its center in the longitudinal direction is positioned near the screw insertion hole 107d.

The cylindrical part 109 is provided around the screw insertion hole 107d in a substantially cylindrical shape. Positioning notches 109a and 109a that open to the front end side are formed in the cylindrical part 109, and the positioning notches 109a and 109a are positioned opposite to each other by 180°.

The cylindrical part 109 is inserted into the lever support hole 97a, and thus the manipulation lever 106 is supported on the left side face part 97 to be freely rotatable. At least a part of the manipulation lever 106 protrudes from the other insertion hole formed in the outer circumference part 8 of the outer housing 2 to a side.

Since at least a part of the manipulation lever 106 protrudes from the insertion hole of the outer housing 2 to the side as described above, it is possible to perform manual rotation manipulation of the manipulation lever 106 from the outside of the protection sheet 300. Manipulation of the manipulation lever 106 from the outside of the protection sheet 300 can be performed in the state in which the protection sheet 300 overlaps the manipulation lever 106 and thus they are gripped together.

In addition, in order to secure a satisfactory manipulation property of the manipulation lever 106 like the manual manipulation knob 80 described above, a configuration in which the manipulation lever 106 is rotated by, for example, connecting a manipulation mechanism having a manipulation unit with which manual manipulation can be performed at a different position from the manipulation lever 106 to the manipulation lever 106, and manually manipulating the manipulation unit is possible.

Figure 37:
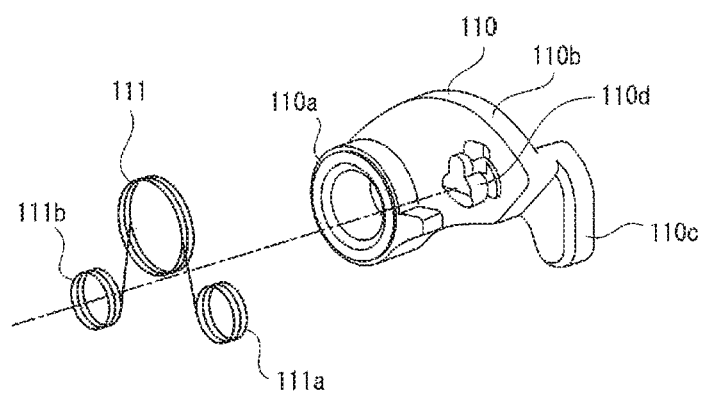
FIG. 37 is an enlarged exploded perspective diagram illustrating a click lever and a urging spring.

A click lever 110 is supported by the support shaft 97c on the left side face part 97 to be freely rotatable (refer to FIGS. 3, 29, and 31). The click lever 110 has a cylindrical shaft-shaped part 110a of which the axial direction is set to the left-right direction, a plate-shaped connection plate part 110b of which one end continues from the shaft-shaped part 110a, facing the left-right direction, and a plate-like engagement protrusion part 110c that is positioned on the outer side (left side) of the connection plate part 110b, facing the left-right direction, as illustrated in FIGS. 29 and 37. A spring support protrusion part 110d that protrudes inward (to the right side) from the connection plate part 110b is provided in the click lever 110.

The click lever 110 is supported on the left side face part 97 to be freely rotatable around the support shaft 97c because the support shaft 97c is inserted into the shaft-shaped part 110a. The click lever 110 is supported on the left side face part 97 by inserting a shoulder screw 150 into the shaft-shaped part 110a to be screwed into the support shaft 97c.

In the state in which the click lever 110 is supported on the left side face part 97, an urging spring 111 is supported between the left side face part 97 and the click lever 110. The urging spring 111 is, for example, a toggle spring, one end 111a of which is supported by the spring hook protrusion 97b of the left side face part 97, and the other end 111b of which is supported by the spring support protrusion part 110d of the click lever 110.

The click lever 110 is positioned on an upper side of the manipulation lever 106, and the engagement protrusion part 110c presses the outer circumferential face of the manipulation lever 106 from above using an urging force of the urging spring 111.

Figure 38:
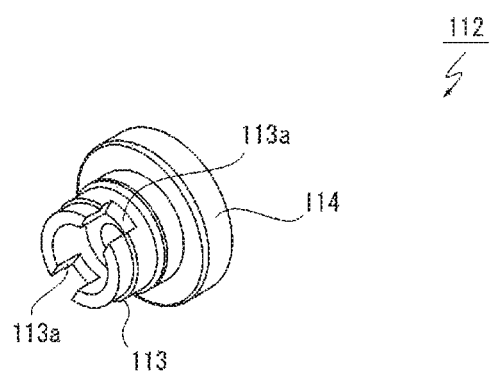
FIG. 38 is an enlarged perspective diagram of a cylindrical cap.

A cylindrical cap 112 is supported on the right side face part 98 to be freely rotatable (refer to FIG. 31). The cylindrical cap 112 integrates an insertion cylinder part 113 formed in a substantially cylindrical shape and a flange-like exfoliation regulation part 114 jutting outward from one end of the insertion cylinder part 113 in the axial direction, as illustrated in FIGS. 31 and 38. Positioning notches 113a and 113a that open to the opposite side to the exfoliation regulation part 114 are formed in the insertion cylinder part 113, and the positioning notches 113a and 113a are positioned opposite to each other by 180°.

The cylindrical cap 112 is supported on the right side face part 98 to be freely rotatable as the insertion cylinder part 113 is inserted into the cap support hole 98a.

A first position detection sensor 115 and a second position detection sensor 116 are mounted on the right side face part 98 (refer to FIG. 30). As the first position detection sensor 115 and the second position detection sensor 116, for example, a photointerrupter which performs optical detection is used.

The first position detection sensor 115 has a pair of detectors 115a and 115a and terminals 115b and 115b, the detectors 115a and 115a are positioned on an inner face side of the right side face part 98, and the terminals 115b and 115b protrude on an outer face side of the right side face part 98 from one terminal protrusion hole 98b. The first position detection sensor 115 is connected to a detection circuit that is not illustrated via the terminals 115b and 115b.

The second position detection sensor 116 has a pair of detectors 116a and 116a and terminals 116b and 116b, the detectors 116a and 116a are positioned on the inner face side of the right side face part 98, and the terminals 116b and 116b protrude on the outer face side of the right side face part 98 from the other terminal protrusion hole 98b. The second position detection sensor 116 is connected to a detection circuit that is not illustrated via the terminals 116b and 116b.

The first position detection sensor 115 and the second position detection sensor 116 are positioned separately from each other in the circumferential direction in which the cap support hole 98a serves as a fulcrum.

In the state in which the cylindrical cap 112 is supported and the first position detection sensor 115 and the second position detection sensor 116 are mounted on the right side face part 98, a side face cover 117 is mounted on an outer face of the right side face part 98 (refer to FIG. 4). Thus, the cylindrical cap 112, the terminals 115b and 115b of the first position detection sensor 115, and the terminals 116b and 116b of the second position detection sensor 116 are covered and protected by the side face cover 117.

The element holding frame 118 is supported inside the rear support housing 91 to be freely rotatable (refer to FIG. 31). The element holding frame 118 has an element holding part 119, a left wall 120, a right wall 121, a divider 122, and a light shielding wall 123 (refer to FIGS. 39 to 41).

The element holding part 119 has an intermediate frame part 124, a one-end frame part 125, and an other-end frame part 126, all of which are formed in rectangular shapes that extend horizontally. The intermediate frame part 124, the one-end frame part 125, and the other-end frame part 126 are consecutively provided, the one-end frame part 125 is positioned on a lower side of the other-end frame part 126, and the intermediate frame part 124 is positioned between the one-end frame part 125 and the other-end frame part 126.

The lower end part of the intermediate frame part 124 overlaps the upper end part of the one-end frame part 125, and the upper end part of the intermediate frame part 124 overlaps the lower end part of the other-end frame part 126.

Figure 40:
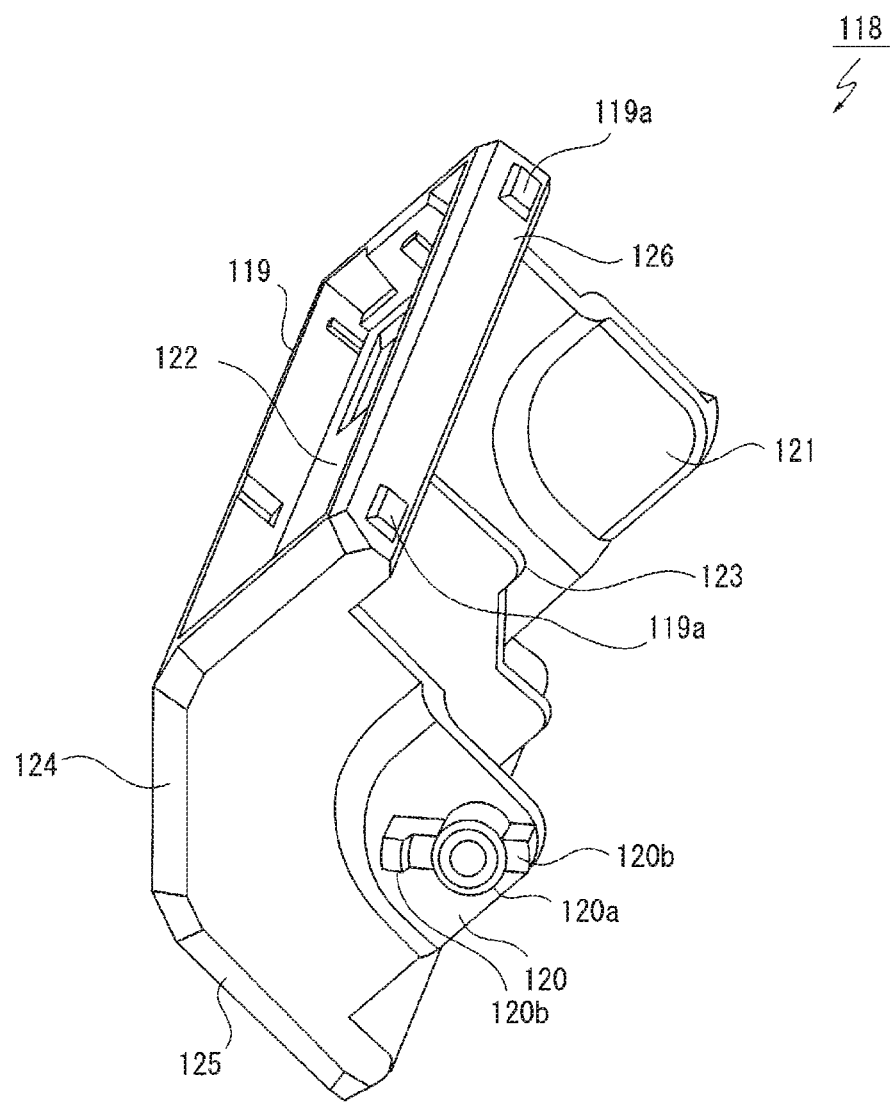
FIG. 40 is an enlarged perspective diagram illustrating the element holding frame viewed in a different direction from FIG. 39.

Protruding first stopper-receiving parts 119a and 119a are provided on the left and right end parts on the end face of the other-end frame part 126 on the opposite side to the intermediate frame part 124 in the element holding part 119 (refer to FIG. 40). Protruding second stopper-receiving parts 119b and 119b are provided on the left and right end parts on the end face of the one-end frame part 125 on the opposite side to the intermediate frame part 124 in the element holding part 119 (refer to FIG. 41).

Figure 42:
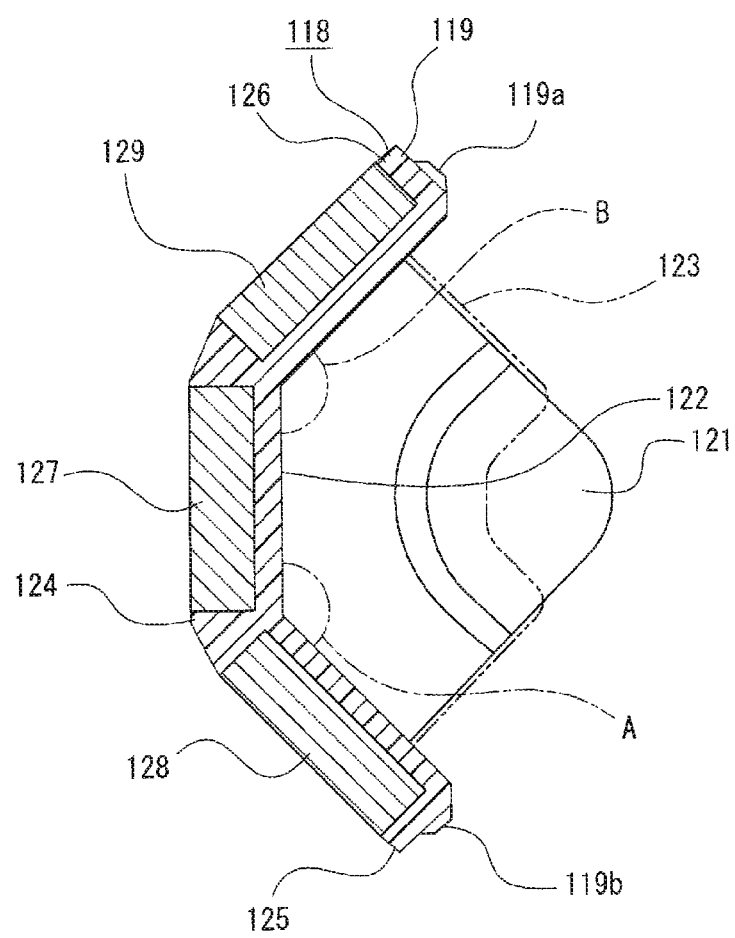
FIG. 42 is an enlarged cross-sectional diagram illustrating the element holding frame and an optical element mounted in the element holding frame.

An angle A between the intermediate frame part 124 and the one-end frame part 125 is set to 135 degrees and an angle B between the intermediate frame part 124 and the other-end frame part 126 is set to 135 degrees within a vertical surface including the optical axis in the element holding frame 118 as illustrated in FIG. 42. Thus, the angle between the one-end frame part 125 and the other-end frame part 126 within the vertical surface including the optical axis is set to 90 degrees, and thus the one-end frame part 125 and the other-end frame part 126 are in a vertical state.

Figure 39:
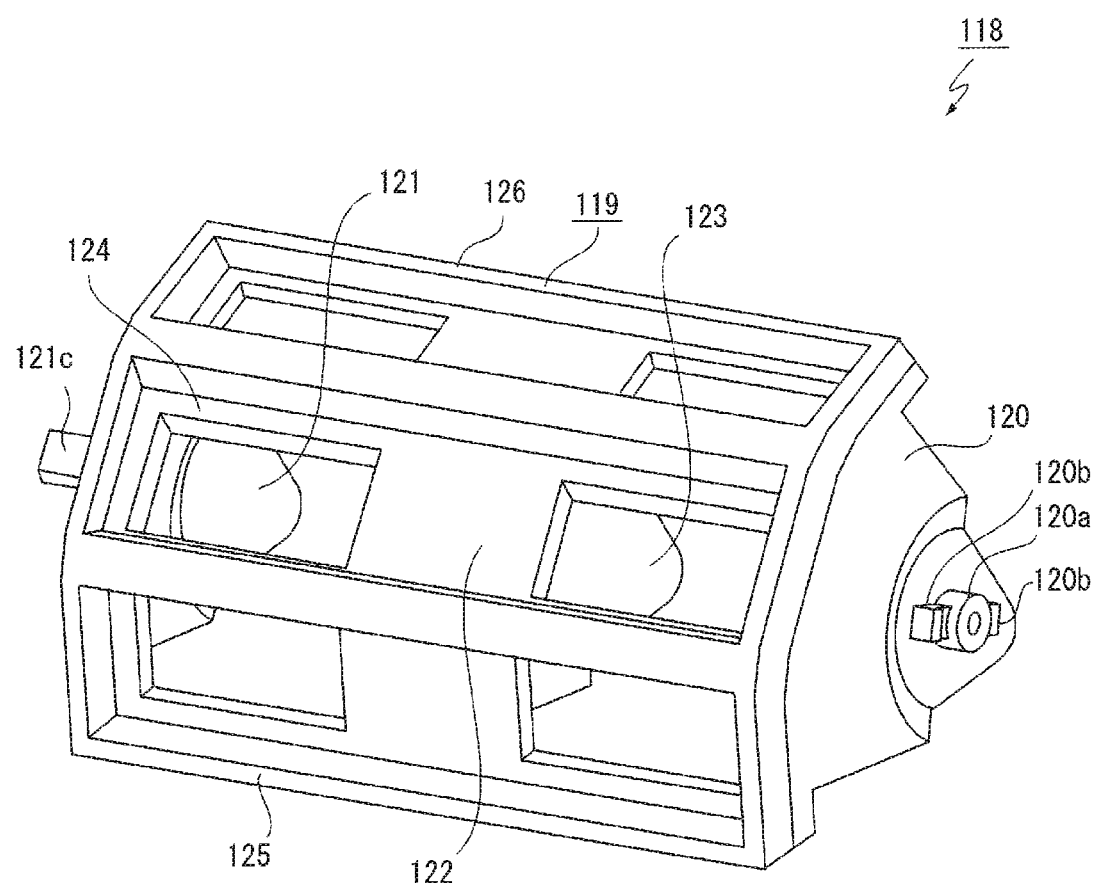
FIG. 39 is an enlarged perspective diagram of an element holding frame.
Figure 41:
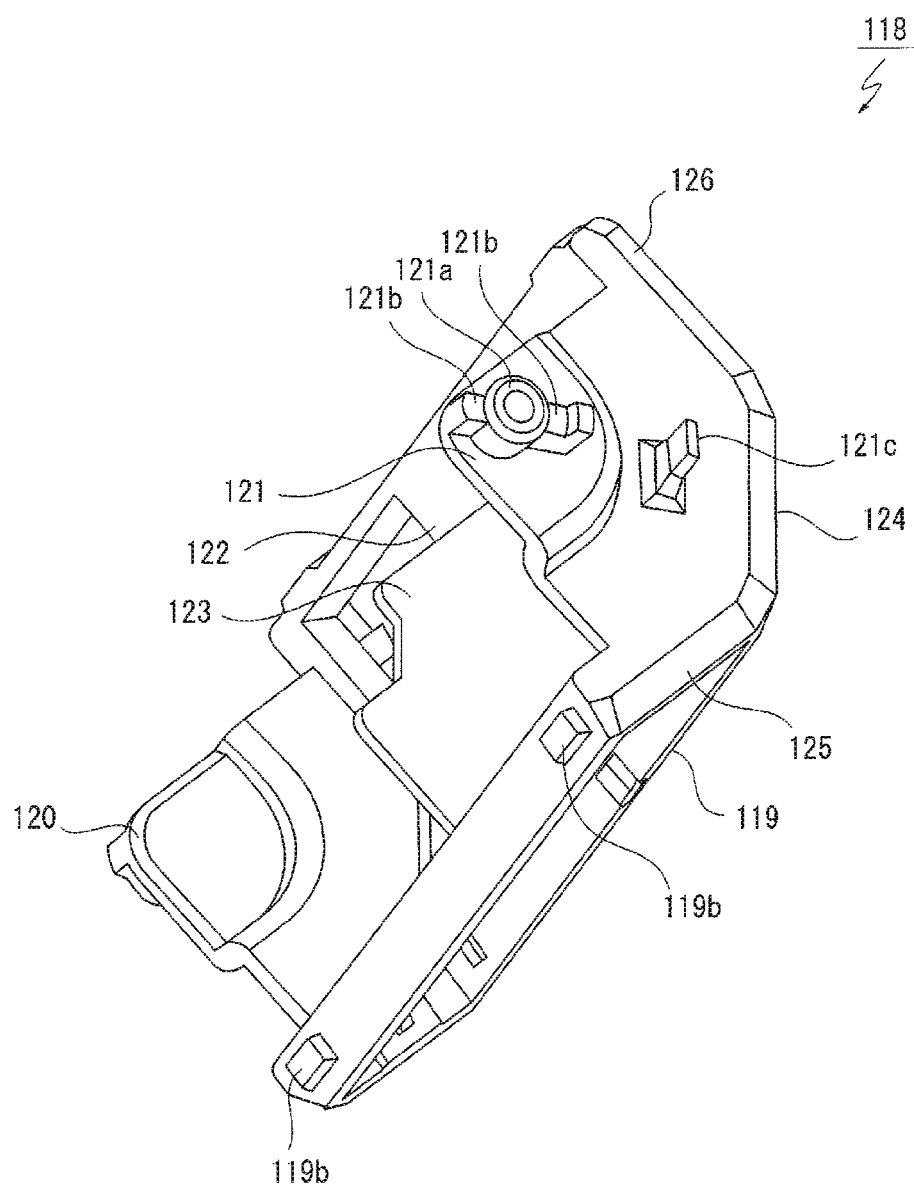
FIG. 41 is an enlarged perspective diagram illustrating the element holding frame viewed from a different direction from FIGS. 39 and 40.

The left wall 120 protrudes from the left end part of the element holding part 119 in the direction orthogonal to the element holding part 119 (refer to FIGS. 39 to 41). A fulcrum shaft 120a whose axial direction is set to the left-right direction is provided on the outer face in the leading end part of the left wall 120 (refer to FIGS. 39 and 40). The fulcrum shaft 120a is formed in a cylindrical shape that opens outward. Positioning protrusion parts 120b and 120b that are consecutive on the outer circumference of the fulcrum shaft 120a are provided on the left wall 120. The positioning protrusion parts 120b and 120b are provided opposite to each other with the fulcrum shaft 120a therebetween.

The right wall 121 protrudes from the right end part of the element holding part 119 in the direction orthogonal to the element holding part 119 (refer to FIGS. 39 to 41). A fulcrum shaft 121a whose axial direction is set to the left-right direction is provided on the outer face in the leading end part of the right wall 121 (refer to FIG. 41). The fulcrum shaft 121a is formed in a cylindrical shape that opens outward. Positioning protrusion parts 121b and 121b that are consecutive on the outer circumference of the fulcrum shaft 121a are provided on the right wall 121. The positioning protrusion parts 121b and 121b are provided opposite to each other with the fulcrum shaft 121a therebetween.

A detection piece 121c that protrudes outward is provided on the right wall 121.

The divider 122 is positioned at the center of the element holding part 119 in the left-right direction, and provided from the lower end part of the one-end frame part 125 to the upper end part of the other-end frame part 126 (refer to FIGS. 39 to 41). Thus, the respective inner spaces of the intermediate frame part 124, the one-end frame part 125, and the other-end frame part 126 of the element holding part 119 are divided into the left and right by the divider 122.

The light shielding wall 123 protrudes from the divider 122, and is positioned parallel with the left wall 120 and the right wall 121.

The light shielding wall 123 has a function of, when light enters the fifth lens groups 100 and 100 held in the rear face part 96 of the case body 92 from the fourth lens groups 99 and 99 held in the cover body 93, shielding some of the light and preventing it from entering the right fifth lens group 100 from the left fourth lens group 99 or the left fifth lens group 100 from the right fourth lens group 99.

Thus, the light shielding wall 123 can prevent unnecessary incidence of light on the respective optical paths in the binocular optical system, and therefore quality of images and videos captured by the medical observation device 1 can be improved.

In addition, the light shielding wall 123 reinforces the element holding frame 118, and thus strength of the element holding frame 118 is increased.

A first optical element 127 is mounted and held in the intermediate frame part 124 of the element holding frame 118 from the front side of the divider 122 through adhesion or the like. The first optical element 127 is an optical filter, and as the first optical element 127, for example, an infrared cut-off filter is used.

A second optical element 128 is mounted and held in the one-end frame part 125 of the element holding frame 118 from the front side of the divider 122 through adhesion or the like. The second optical element 128 is an optical filter, and as the second optical element 128, for example, a special light observation filter that allows only excitation wavelengths of fluorochrome to pass therethrough is used.

The second optical element 128 is used in, for example, photo dynamic diagnosis (PDD) in the medical field. Photo dynamic diagnosis is a diagnosis method of observing a state of a tumor using a special light observation filter that allows only fluorescence that is excited when light having a specific wavelength is radiated thereto to pass therethrough when a photosensitive substance or fluorescent substance has been administered into a body and specifically accumulates in excess in the tumor.

A third optical element 129 is mounted and held in the other-end frame part 126 of the element holding frame 118 from the front side of the divider 122 through adhesion or the like. The third optical element 129 is an optical filter, and as the third optical element 129, for example, a special light observation filter that allows only excitation wavelengths of fluorochrome to pass therethrough is used.

The third optical element 129 is used in, for example, indocyanine green (ICG) fluorescence imaging in the medical field. The ICG fluorescence imaging is a method of observing a state of a blood vessel or the like using a special light observation filter that allows only fluorescence that is excited when near infrared light of a specific wavelength area is radiated thereto to pass therethrough when ICG that is a fluorescent substance has been administered into a body and bonded with a specific substance included in the blood.

The imaging optical system is provided in the medical observation device 1 as a binocular optical system, and the first optical element 127, the second optical element 128, and the third optical element 129 are positioned across the two optical axes of the binocular optical system.

As described above, the first optical element 127, the second optical element 128, and the third optical element 129 each having different selectivity of wavelengths that pass therethrough are used in the medical observation device 1.

Thus, types of captured images differ according to subjects (lesions), imaging can be performed according to applications, and therefore functionality of the medical observation device 1 can be improved.

In addition, the imaging optical system is provided in the medical observation device 1 as a binocular optical system, and the first optical element 127, the second optical element 128, and the third optical element 129 are positioned across the two optical axes of the binocular optical system.

Thus, since each of the first optical element 127, the second optical element 128, and the third optical element 129 is positioned to be compatible with a binocular optical system, the number of optical elements may decrease accordingly, the number of components can thus be reduced, and therefore high functionality of the medical observation device 1 can be secured.

Note that, although the example in which the second optical element 128 is used for PDD and the third optical element 129 is used for ICG has been described above, conversely, the second optical element 128 may be used for ICG and the third optical element 129 may be used for PDD.

However, the first optical element 127 that is an infrared cut-off filter is an optical element with the highest use frequency. Thus, in both cases in which it is desired to use the first optical element 127 after use of the second optical element 128 and to use the first optical element 127 after use of the third optical element 129, it is desirable to position the first optical element 127 between the second optical element 128 and the third optical element 129 so that the first optical element 127 can be quickly used when the element holding frame 118 is rotated.

The element holding frame 118 is connected to the manipulation lever 106 as a stepped screw 151 is inserted into the cylindrical part 109 of the manipulation lever 106 to be screwed into the fulcrum shaft 120a of the left wall 120 in the state in which the element holding frame 118 is inserted into the rear support housing 91 (refer to FIG. 31). At this moment, the positioning protrusion parts 120b and 120b provided on the left wall 120 of the element holding frame 118 are inserted into the positioning notches 109a and 109a formed in the cylindrical part 109 of the manipulation lever 106, and thus the manipulation lever 106 and the element holding frame 118 are positioned, and rotation of the element holding frame 118 with respect to the manipulation lever 106 is regulated. Thus, the manipulation lever 106 and the element holding frame 118 are integrated and can rotate together.

In addition, the element holding frame 118 is connected to the cylindrical cap 112 as a stepped screw 152 is inserted into the insertion cylinder part 113 of the cylindrical cap 112 to be screwed into the fulcrum shaft 121a of the right wall 121 in the state in which the element holding frame 118 is inserted into the rear support housing 91. At this moment, the positioning protrusion parts 121b and 121b provided on the right wall 121 of the element holding frame 118 are inserted into the positioning notches 113a and 113a formed in the insertion cylinder part 113 of the cylindrical cap 112, and thus the cylindrical cap 112 and the element holding frame 118 are positioned, and rotation of the element holding frame 118 with respect to the cylindrical cap 112 is regulated. Thus, the cylindrical cap 112 and the element holding frame 118 are integrated with the manipulation lever 106 and can rotate together.

With the configuration described above, the element holding frame 118 holding the first optical element 127, the second optical element 128, and the third optical element 129 is integrated with the manipulation lever 106 and the cylindrical cap 112 and can be rotated with respect to the rear support housing 91, and the axial direction of the rotation shaft of the element holding frame 118, i.e., the direction in which the fulcrum shaft 120a of the left wall 120 is connected with the fulcrum shaft 121a of the right wall 121, is set as the direction orthogonal to the optical axis direction (the left-right direction).

In the state in which the element holding frame 118 is rotatable inside the rear support housing 91, the element holding frame 118 is positioned between the fourth lens groups 99 and 99 and the fifth lens groups 100 and 100, both of which are fixed lens groups, and the element holding frame 118, the first optical element 127, the second optical element 128, and the third optical element 129 are positioned between the portions in which the respective fixed lens groups are mounted in the rear support housing 91.

Thus, respective portions of the element holding frame 118, the first optical element 127, the second optical element 128, and the third optical element 129 are shielded by each part in which the fixed lens groups are mounted in the optical axis direction, adhesion of foreign substances like dust to the first optical element 127, the second optical element 128, and the third optical element 129 can thus be suppressed, and therefore quality of images and videos captured by the medical observation device 1 can be improved.

Furthermore, since the rear support housing 91 is formed in a box shape having a space inside and the element holding frame 118 is positioned inside the rear support housing 91, the element holding frame 118, the first optical element 127, the second optical element 128, and the third optical element 129 are tightly sealed by the rear support housing 91.

Therefore, adhesion of foreign substances like dust to the first optical element 127, the second optical element 128, and the third optical element 129 can be further suppressed, and quality of images and videos captured by the medical observation device 1 can be further improved.

A rotation operation of the element holding frame 118 will be described below (with reference to FIGS. 43 to 51).

The element holding frame 118 is rotated between a first rotation position and a second rotation position, the center position of the rotation range from the first rotation position to the second rotation position is set as an intermediate position, and the element holding frame 118 stops and is held at any position of the first rotation position, the intermediate position, and the second rotation position.

Figure 43:
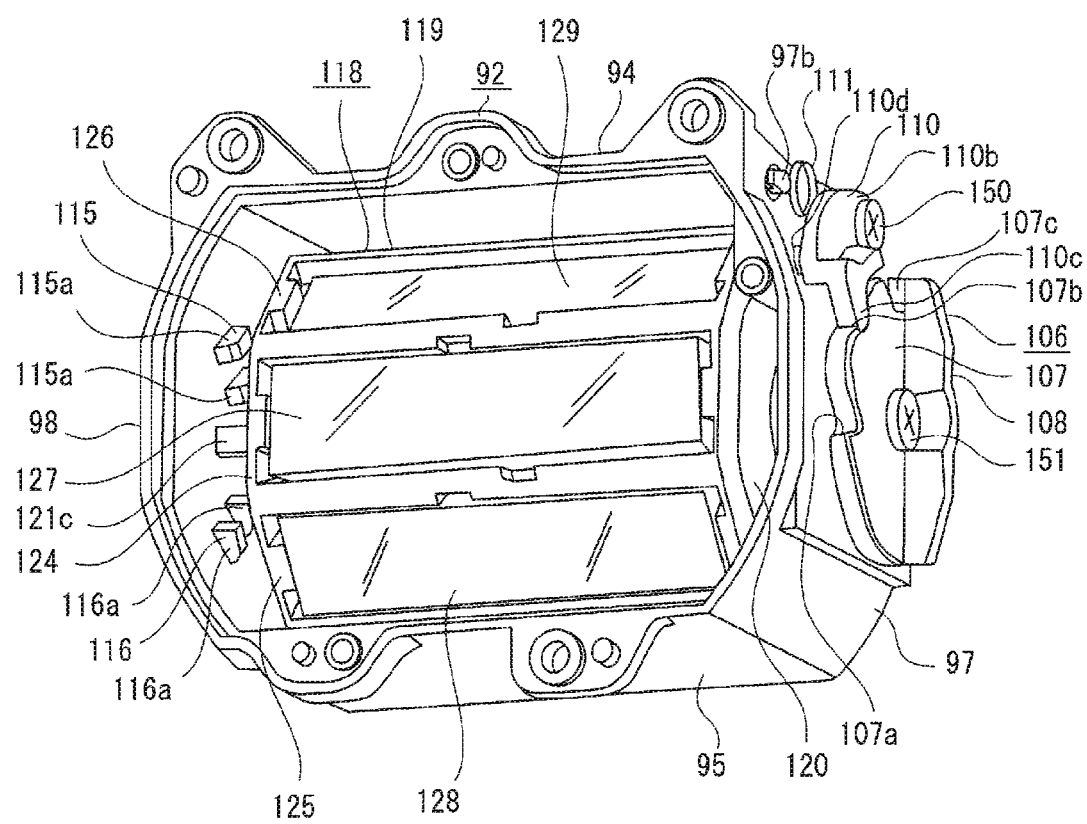
FIG. 43 is an enlarged perspective diagram illustrating a rotation operation of the element holding frame along with FIGS. 44 to 51, illustrating a state in which the element holding frame is held at an intermediate position.
Figure 44:
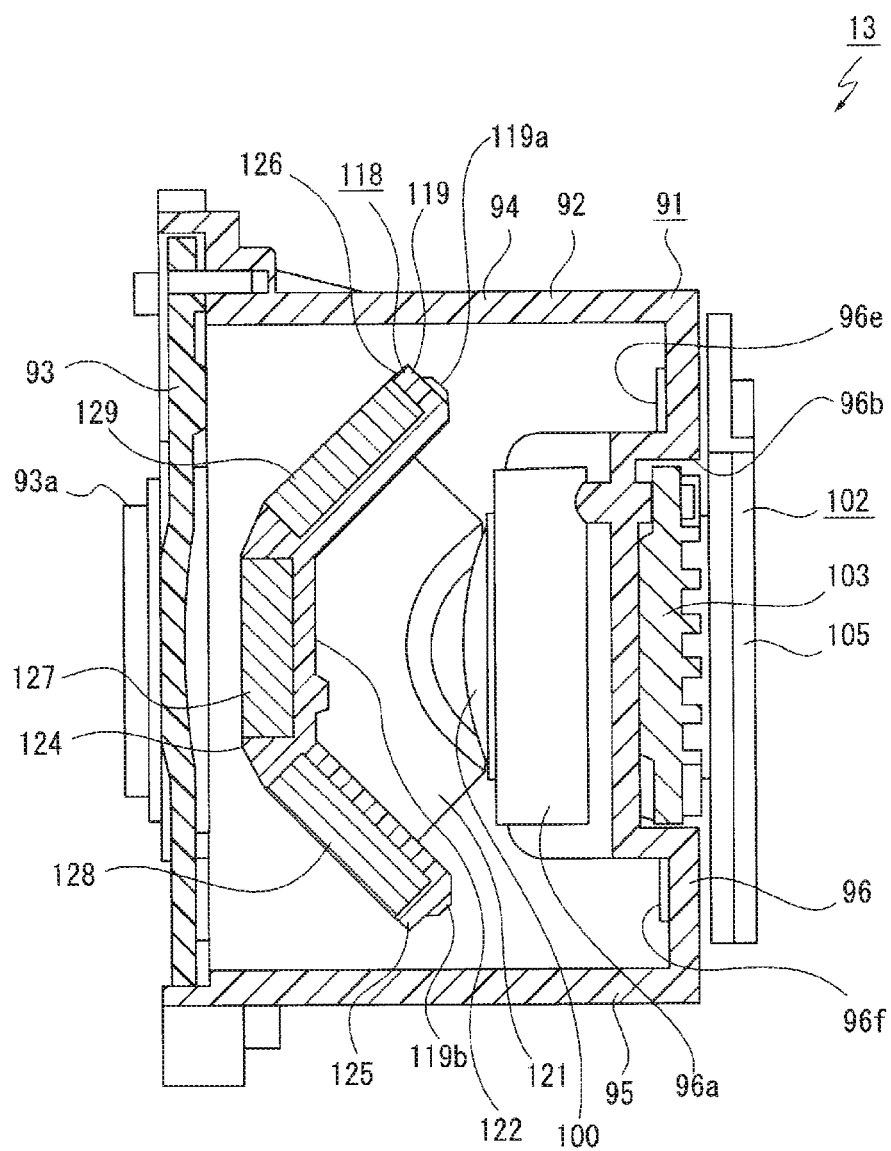
FIG. 44 is an enlarged cross-sectional diagram illustrating the element holding frame held at the intermediate position.

In a state in which the element holding frame 118 is at the intermediate position, the first optical element 127 held in the intermediate frame part 124 of the element holding frame 118 is positioned on the optical axis to be orthogonal to the optical axis, facing the front-rear direction, as illustrated in FIGS. 43 and 44. Thus, light that has passed through the fourth lens groups 99 and 99 passes through the first optical element 127 and then is incident on the fifth lens groups 100 and 100.

At this moment, the engagement protrusion part 110c of the click lever 110 is engaged with the second engagement concave part 107b of the manipulation lever 106 (refer to FIG. 43), and the engagement protrusion part 110c is pressed by an urging force of the urging spring 111 from above the rotation plate part 107. Thus, since the manipulation lever 106 is pressed by the engagement protrusion part 110c, the element holding frame 118 is held at the intermediate position.

Figure 45:
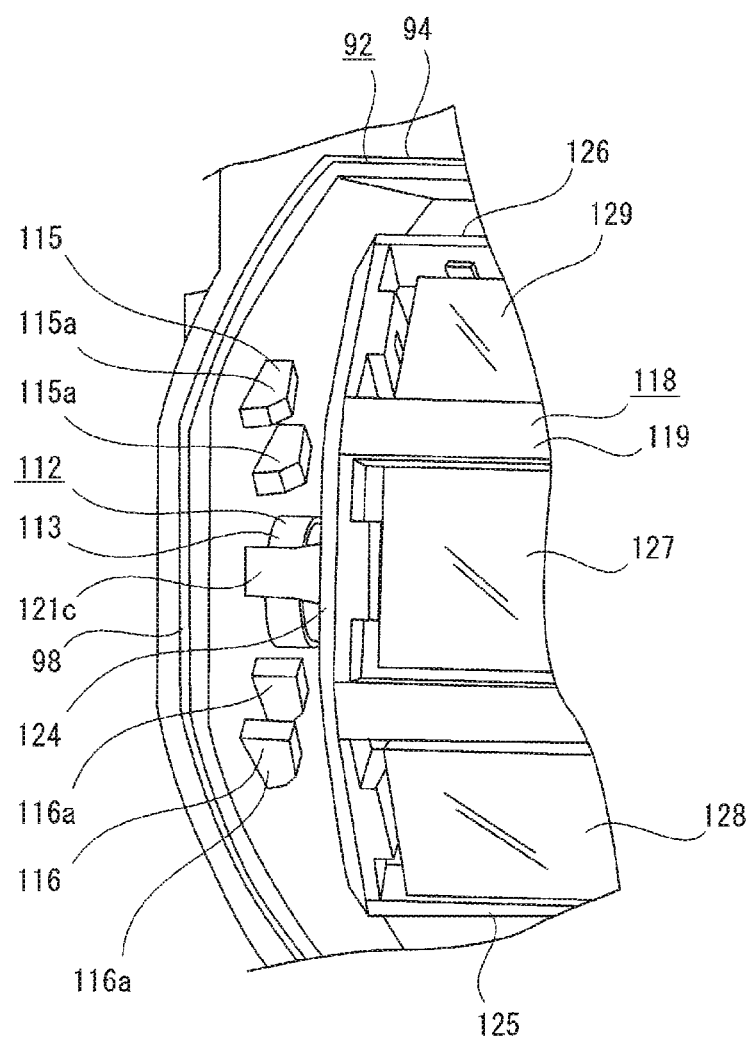
FIG. 45 is an enlarged perspective diagram illustrating a state in which the element holding frame is held at the intermediate position and a detection piece of the element holding frame is positioned between two position detection sensors.

At the intermediate position, the detection piece 121c provided on the right wall 121 of the element holding frame 118 is positioned between first position detection sensor 115 and the second position detection sensor 116 mounted on the right side face part 98 of the rear support housing 91 (refer to FIG. 45). Since the detection piece 121c is positioned between the first position detection sensor 115 and the second position detection sensor 116 and is present neither between the pair of detectors 115a and 115a nor between the pair of detectors 116a and 116a, the element holding frame 118 is detected to be at the intermediate position.

Figure 46:
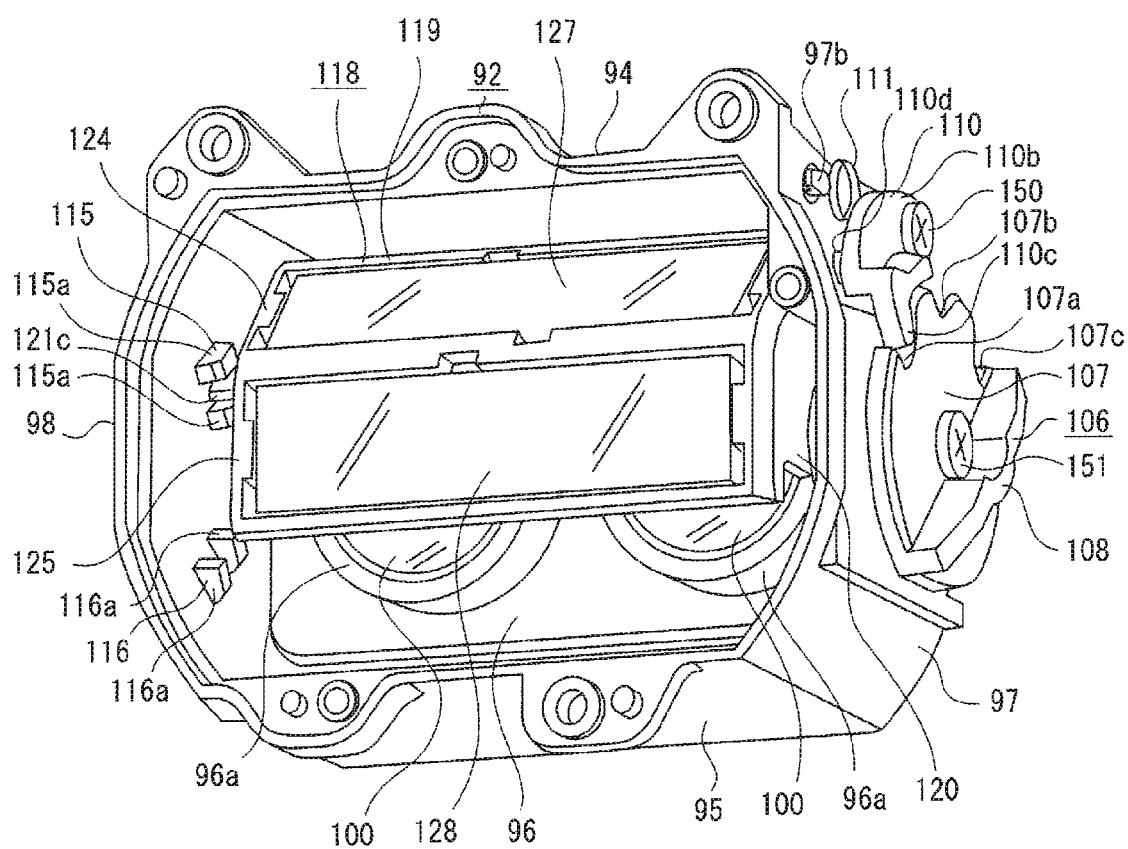
FIG. 46 is an enlarged perspective diagram illustrating a state in which the element holding frame is held at a first rotation position.
Figure 47:
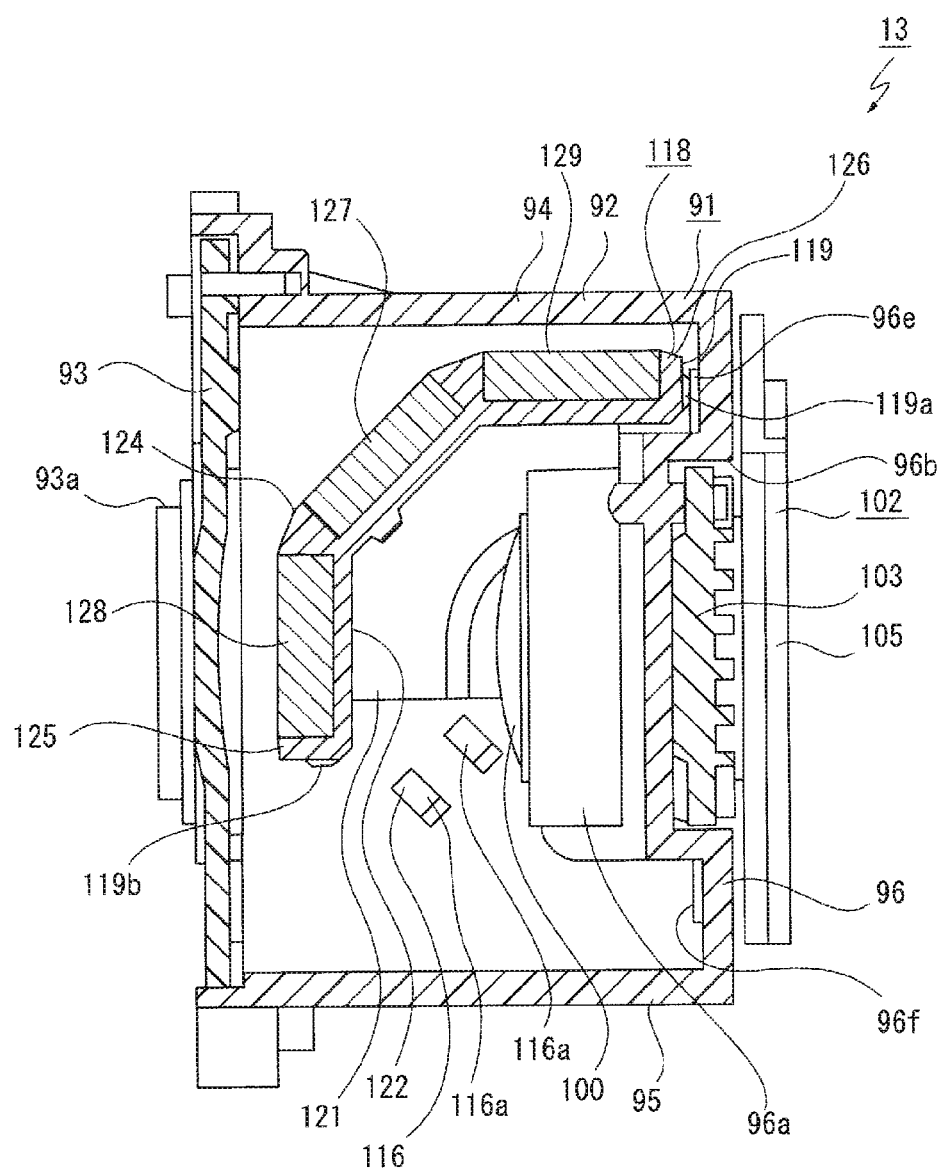
FIG. 47 is an enlarged cross-sectional diagram illustrating a state in which the element holding frame is held at the first rotation position.

If the manipulation lever 106 is manipulated to rotate to one side in the state in which the element holding frame 118 is at the intermediate position, the manipulation lever 106 rotates while the engagement protrusion part 110c of the click lever 110 is pressed to the outer circumferential face of the rotation plate part 107 by an urging force of the urging spring 111, and the engagement protrusion part 110*c* is engaged with the first engagement concave part 107*a* (refer to FIGS. 46 and 47). When the manipulation lever 106 is manually manipulated to rotate, the operator 700 or the like can grip the manipulation protrusion part 108 of the manipulation lever 106 to manipulate it, and thus the provision of the manipulation protrusion part 108 in the manipulation lever 106 can enable rotation manipulation of the manipulation lever 106 to be easily and reliably performed.

At this moment, rotation of the element holding frame 118 is regulated when the first stopper-receiving parts 119*a* and 119*a* run into the first stopper parts 96*e* and 96*e* provided in the rear face part 96 of the rear support housing 91, and thus rotation to the first rotation position is performed (refer to FIG. 47). In the state in which the element holding frame 118 is rotated to the first rotation position, the engagement protrusion part 110*c* is pressed to the first engagement concave part 107*a* by an urging force of the urging spring 111 applied in the direction in which the manipulation lever 106 is rotated clockwise when viewed from the outside. Thus, the urging force of the urging spring 111 is transmitted to the element holding frame 118 via the manipulation lever 106, the first stopper-receiving parts 119*a* and 119*a* of the element holding frame 118 are pressed to the first stopper parts 96*e* and 96*e*, and then the element holding frame 118 is held at the first rotation position since the first stopper-receiving parts 119*a* and 119*a* are pressed to the first stopper parts 96*e* and 96*e*.

In the medical observation device 1 described above, the first stopper-receiving parts 119*a* and 119*a* are provided in the element holding frame 118, and the first stopper parts 96*e* and 96*e* for holding the element holding frame 118 at the first rotation position when the first stopper-receiving parts 119*a* and 119*a* are brought into contact with the rear support housing 91 are provided.

Thus, no mechanism for holding the element holding frame 118 at the first rotation position is necessary, and the element holding frame 118 can be easily and reliably held at the first rotation position without causing an increase in manufacturing costs of the medical observation device 1.

In addition, the urging spring 111 that presses the first stopper-receiving parts 119*a* and 119*a* to the first stopper parts 96*e* and 96*e* is provided in the medical observation device 1.

Thus, since the first stopper-receiving parts 119*a* and 119*a* are pressed to the first stopper parts 96*e* and 96*e* by the urging force of the urging spring 111, the element holding frame 118 can be held at the first rotation position in a stable state.

In the state in which the element holding frame 118 is rotated to the first rotation position, the second optical element 128 held in the one-end frame part 125 of the element holding frame 118 is positioned on the optical axis to be orthogonal to the optical axis, facing the front-rear direction as illustrated in FIGS. 46 and 47. Thus, light that has passed through the fourth lens groups 99 and 99 passes through the second optical element 128 and then is incident on the fifth lens groups 100 and 100.

Figure 48:
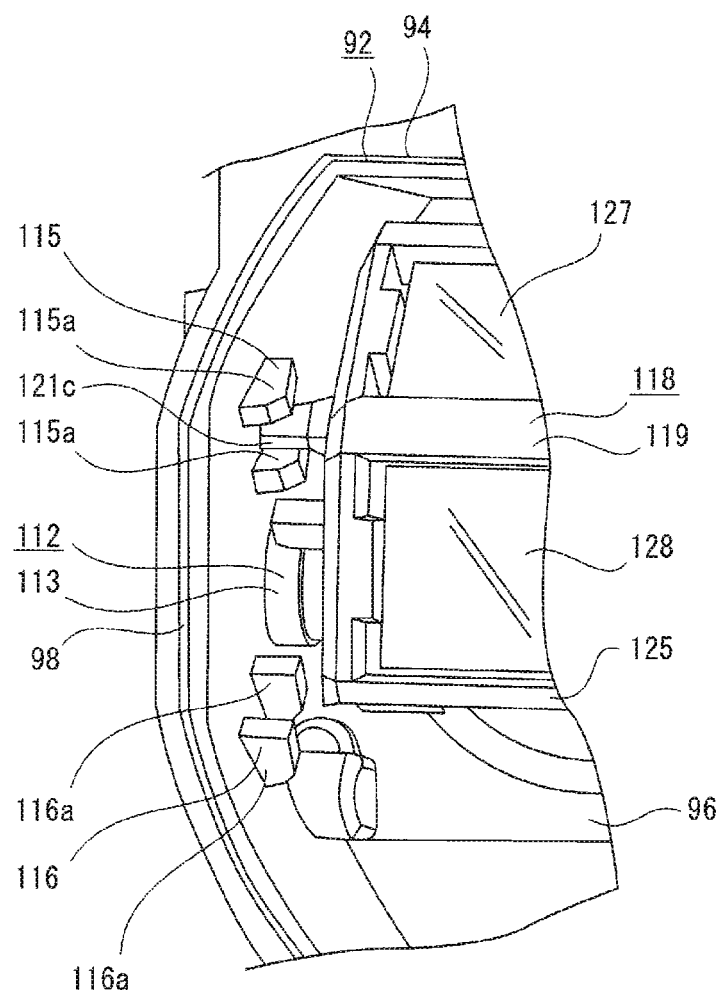
FIG. 48 is an enlarged perspective diagram illustrating a state in which the element holding frame is held at the first rotation position and the detection piece of the element holding frame is positioned between detectors of one position detection sensor.

At the first rotation position, the detection piece 121*c* provided on the right wall 121 of the element holding frame 118 is positioned between the pair of detectors 115*a* and 115*a* of the first position detection sensor 115 mounted on the right side face part 98 of the rear support housing 91 (refer to FIG. 48). Since the detection piece 121*c* is positioned between the pair of detectors 115*a* and 115*a*, it is detected that the element holding frame 118 is at the first rotation position.

As described above, since the angle formed by the intermediate frame part 124 and the one-end frame part 125 and the angle formed by the intermediate frame part 124 and the other-end frame part 126 within the vertical plane including the optical axis are all set to 135 degrees and the angle formed by the one-end frame part 125 and the other-end frame part 126 within the vertical plane including the optical axis is set to 90 degrees, the other-end frame part 126 and the third optical element 129 held in the other-end frame part 126 are parallel with the optical axis in the state in which the element holding frame 118 is held at the first rotation position (refer to FIG. 47).

Thus, the other-end frame part 126 and the third optical element 129 do not protrude in the direction orthogonal to the optical axis, and thus miniaturization of the medical observation device 1 in the direction orthogonal to the optical axis can be achieved.

Figure 49:
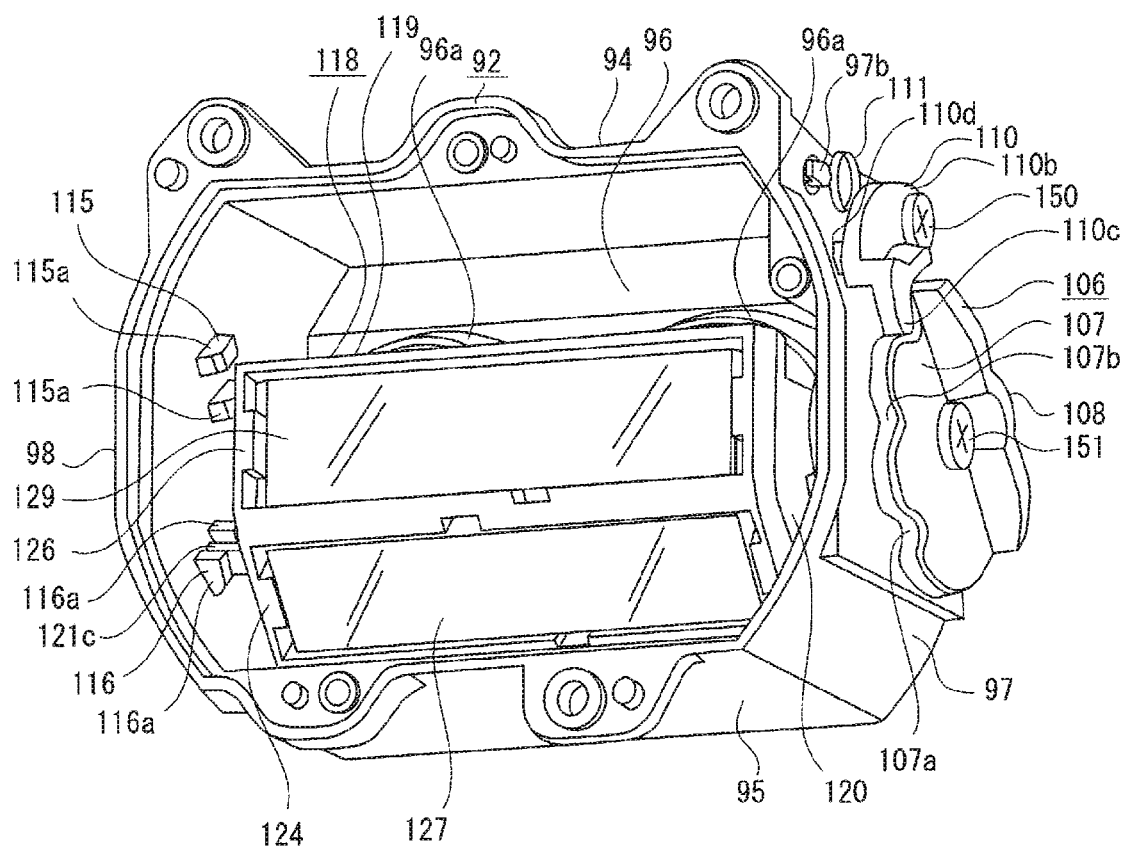
FIG. 49 is an enlarged perspective diagram illustrating a state in which the element holding frame is held at a second rotation position.
Figure 50:
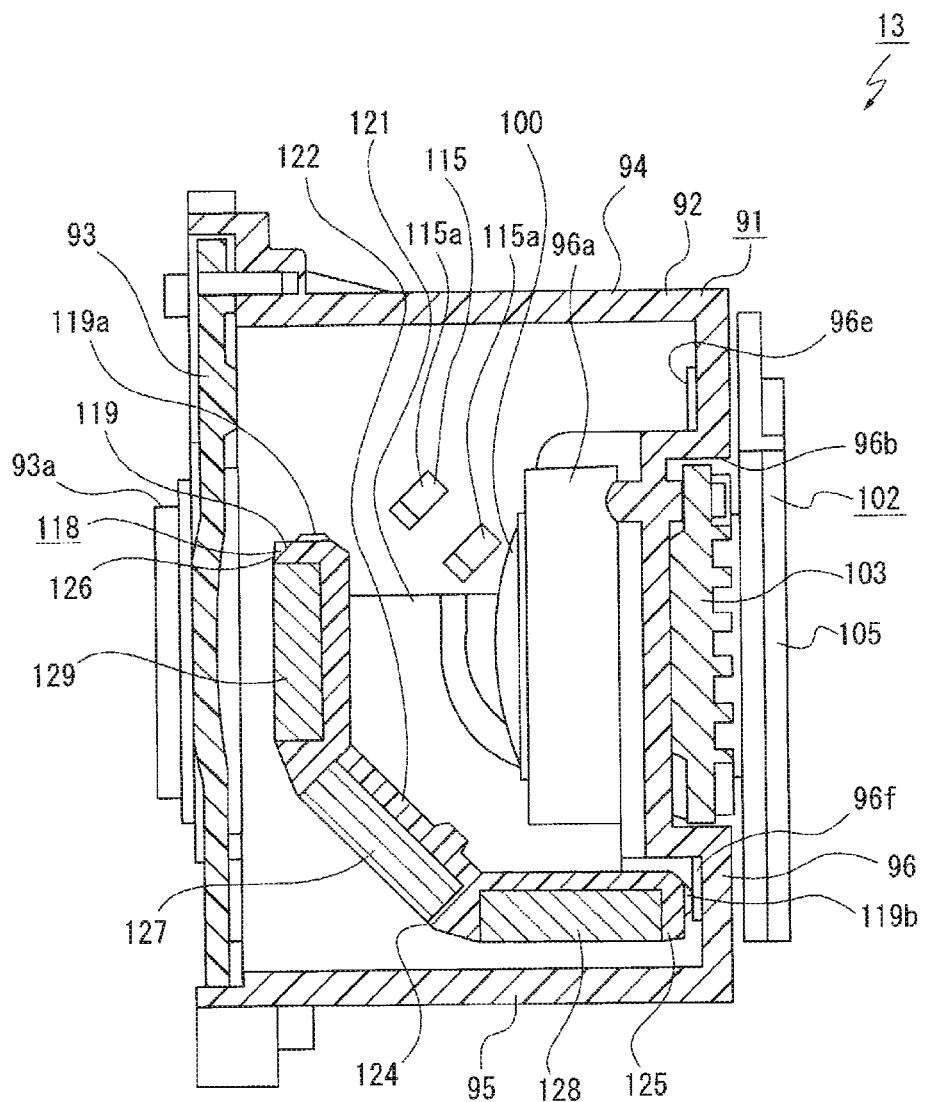
FIG. 50 is an enlarged cross-sectional diagram illustrating a state in which the element holding frame is held at the second rotation position.

On the other hand, if the manipulation lever 106 is manipulated to rotate to the other side in the state in which the element holding frame 118 is at the intermediate position, the manipulation lever 106 is rotated while the engagement protrusion part 110*c* of the click lever 110 is pressed to the outer circumferential face of the rotation plate part 107 by an urging force of the urging spring 111, and the engagement protrusion part 110*c* is engaged with the third engagement concave part 107*c* (refer to FIGS. 49 and 50).

At this moment, rotation of the element holding frame 118 is regulated when the second stopper-receiving parts 119*b* and 119*b* run into the second stopper parts 96*f* and 96*f* provided in the rear face part 96 of the rear support housing 91, and thus rotation to the second rotation position is performed (refer to FIG. 50). In the state in which the element holding frame 118 is rotated to the second rotation position, the engagement protrusion part 110*c* is pressed to the third engagement concave part 107*c* by an urging force of the urging spring 111 applied in the direction in which the manipulation lever 106 is rotated anticlockwise when viewed from the outside. Thus, the urging force of the urging spring 111 is transmitted to the element holding frame 118 via the manipulation lever 106, the second stopper-receiving parts 119*b* and 119*b* of the element holding frame 118 are pressed to the second stopper parts 96*f* and 96*f*, and then the element holding frame 118 is held at the second rotation position since the second stopper-receiving parts 119*b* and 119*b* are pressed to the second stopper parts 96*f* and 96*f*.

In the medical observation device 1 described above, the second stopper-receiving parts 119*b* and 119*b* are provided in the element holding frame 118, and the second stopper parts 96*f* and 96*f* for holding the element holding frame 118 at the second rotation position when the second stopper-receiving parts 119*b* and 119*b* are brought into contact with the rear support housing 91 are provided.

Thus, no mechanism for holding the element holding frame 118 at the second rotation position is necessary, and the element holding frame 118 can be easily and reliably held at the second rotation position without causing an increase in manufacturing costs of the medical observation device 1.

In addition, the urging spring 111 that presses the second stopper-receiving parts 119*b* and 119*b* to the second stopper parts 96*f* and 96*f* is provided.

Thus, since the second stopper-receiving parts 119*b* and 119*b* are pressed to the second stopper parts 96*f* and 96*f* by the urging force of the urging spring 111, the element holding frame 118 can be held at the second rotation position in a stable state.

Furthermore, the urging spring 111 presses the first stopper-receiving parts 119a and 119a to the first stopper parts 96e and 96e at a first rotation end and presses the second stopper-receiving parts 119b and 119b to the second stopper parts 96f and 96f at a second rotation end.

Thus, since the first stopper-receiving parts 119a and 119a and the second stopper-receiving parts 119b and 119b are pressed respectively to the first stopper parts 96e and 96e and the second stopper parts 96f and 96f by the urging force of the one urging spring 111, a reduction in the number of components of the medical observation device 1 and simplification of the mechanism can be achieved, and further the element holding frame 118 can be held at the first rotation position and the second rotation position in stable states.

Note that the medical observation device 1 may also be configured without providing the first stopper-receiving parts 119a and 119a, the second stopper-receiving parts 119b and 119b, the first stopper parts 96e and 96e, and the second stopper parts 96f and 96f, and with the engagement protrusion part 110c of the click lever 110 engaged with the first engagement concave part 107a of the manipulation lever 106 to cause the element holding frame 118 to be held at the first rotation position, and the engagement protrusion part 110c of the click lever 110 engaged with the third engagement concave part 107c of the manipulation lever 106 to cause the element holding frame 118 to be held at the second rotation position.

Furthermore, the medical observation device 1 is configured such that the urging force of the urging spring 111 is applied to the element holding frame 118 via the manipulation lever 106 as described above.

Thus, the manipulation lever 106 functions as a power transmission means that applies a rotation force to the element holding frame 118 and as an urging force transmission means that applies an urging force to the element holding frame 118, and thus power and an urging force can be reliably applied to the element holding frame 118, in addition to achievement of a reduction in the number of components of the medical observation device 1 and simplification of the mechanism.

In addition, when the manipulation lever 106 is manually manipulated to rotate, the engagement protrusion part 110c of the click lever 110 is inserted into and pressed to the first engagement concave part 107a, the second engagement concave part 107b, or the third engagement concave part 107c while sliding with respect to the outer circumferential face of the rotation plate part 107.

Thus, a feeling of a change in an engagement position is transmitted to the hand gripping the manipulation lever 106, and thus the operator 700 or the like who is performing a rotation manipulation experiences a so-called click feeling and recognizes an engagement state of the engagement protrusion part 110c according to the size of a transmitted load, and the operator 700 or the like can easily recognize that necessary rotation manipulation has been completed, and can easily and surely perform the rotation manipulation of the manipulation lever 106 and surely cause the element holding frame 118 to be rotated to another rotation position.

In the state in which the element holding frame 118 is rotated to the second rotation position, the third optical element 129 held in the other-end frame part 126 of the element holding frame 118 is positioned on the optical axis to be orthogonal to the optical axis, facing the front-rear direction as illustrated in FIGS. 49 and 50. Thus, light that has passed through the fourth lens groups 99 and 99 passes through the third optical element 129 and then is incident on the fifth lens groups 100 and 100.

Figure 51:
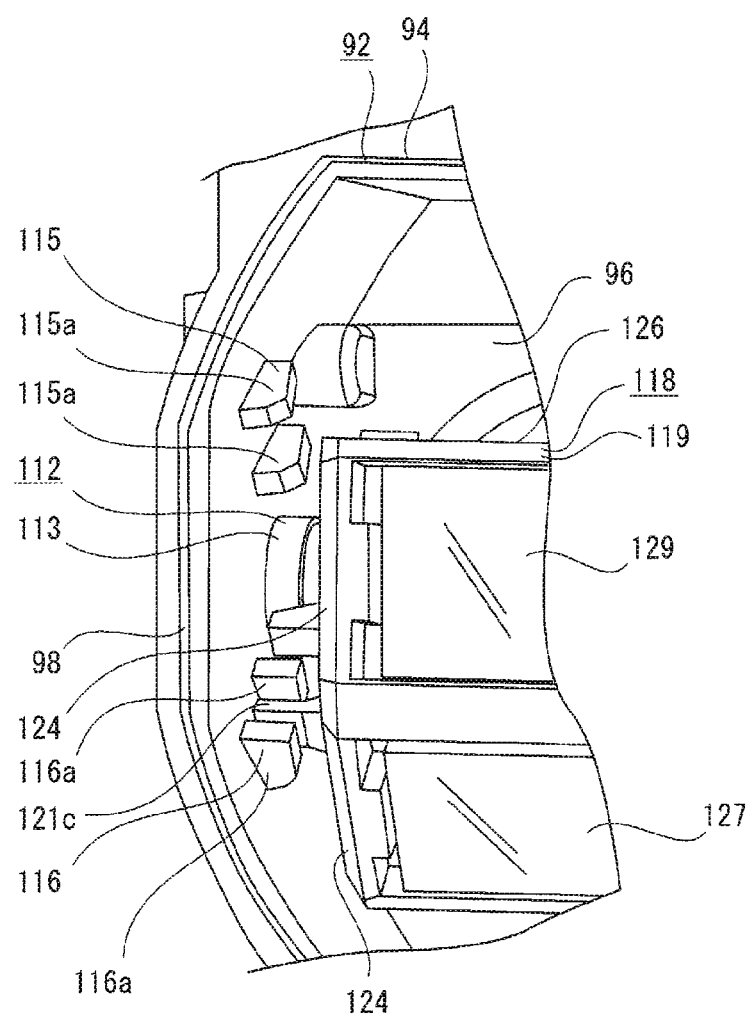
FIG. 51 is an enlarged perspective diagram illustrating a state in which the element holding frame held at a third rotation position and the detection piece of the element holding frame positioned between detectors of one position detection sensor.

At the second rotation position, the detection piece 121c provided on the right wall 121 of the element holding frame 118 is positioned between the pair of detectors 116a and 116a of the second position detection sensor 116 mounted on the right side face part 98 of the rear support housing 91 (refer to FIG. 51). Since the detection piece 121c is positioned between the pair of detectors 116a and 116a, it is detected that the element holding frame 118 is at the second rotation position.

As described above, since the angle formed by the intermediate frame part 124 and the one-end frame part 125 and the angle formed by the intermediate frame part 124 and the other-end frame part 126 within the vertical plane including the optical axis are all set to 135 degrees and the angle formed by the one-end frame part 125 and the other-end frame part 126 within the vertical plane including the optical axis is set to 90 degrees, the one-end frame part 125 and the second optical element 128 held in the one-end frame part 125 are parallel with the optical axis in the state in which the element holding frame 118 is held at the second rotation position (refer to FIG. 47).

Thus, the one-end frame part 125 and the second optical element 128 do not protrude in the direction orthogonal to the optical axis, and thus miniaturization of the medical observation device 1 in the direction orthogonal to the optical axis can be achieved.

Note that, although the example in which the manipulation lever 106 is manually manipulated to rotate has been described above, the manipulation lever 106 may be configured to be driven with a driving force of a motor, or the like.

The above-described first position detection sensor 115 and the second position detection sensor 116 detect rotation positions of the element holding frame 118 at the intermediate position, the first rotation position, and the second rotation position, and processing of respective images is performed according to each of the first optical element 127, the second optical element 128, and the third optical element 129 positioned on the optical axis based on the detection results of the first position detection sensor 115 and the second position detection sensor 116.

Thus, since processing of respective images is performed based on the detection results of the first position detection sensor 115 and the second position detection sensor 116, the images can be properly processed according to the first optical element 127, the second optical element 128, and the third optical element 129 positioned on the optical axis, and functionality of the medical observation device 1 can be improved.

In the medical observation device 1, the axial direction of the rotation shaft of the element holding frame 118 is set to the direction orthogonal to the optical axis direction, and the element holding frame 118 is rotated and thus any of the first optical element 127, the second optical element 128, and the third optical element 129 is positioned on the optical axis as described above.

Thus, since the element holding frame 118 is rotated around the rotation shaft whose axial direction is set to the direction orthogonal to the optical axis direction and thus any of the first optical element 127, the second optical element 128, and the third optical element 129 is positioned on the optical axis, a rotation space of the element holding frame 118 in the direction orthogonal to the optical axis can be small, the functionality of the medical observation device 1 attained by switching the first optical element 127, the second optical element 128, and the third optical element 129 can be improved, and further miniaturization thereof in the direction orthogonal to the optical axis can be achieved.

In addition, in the medical observation device 1, the first optical element 127, the second optical element 128, and the third optical element 129 are provided, and the first optical element 127 and the third optical element 129 are disposed to be perpendicular to each other.

Thus, the distance between the first optical element 127 and the third optical element 129 in the direction orthogonal to the optical axis becomes shorter, and further miniaturization of the medical observation device 1 in the direction orthogonal to the optical axis can be achieved.

[Others]

Although the example in which the first position detection sensor 115 and the second position detection sensor 116 optically detect a rotation position of the element holding frame 118 has been described above, detecting a rotation position of the element holding frame 118 is not limited to optical detection, and other detection methods may be used.

Figure 52:
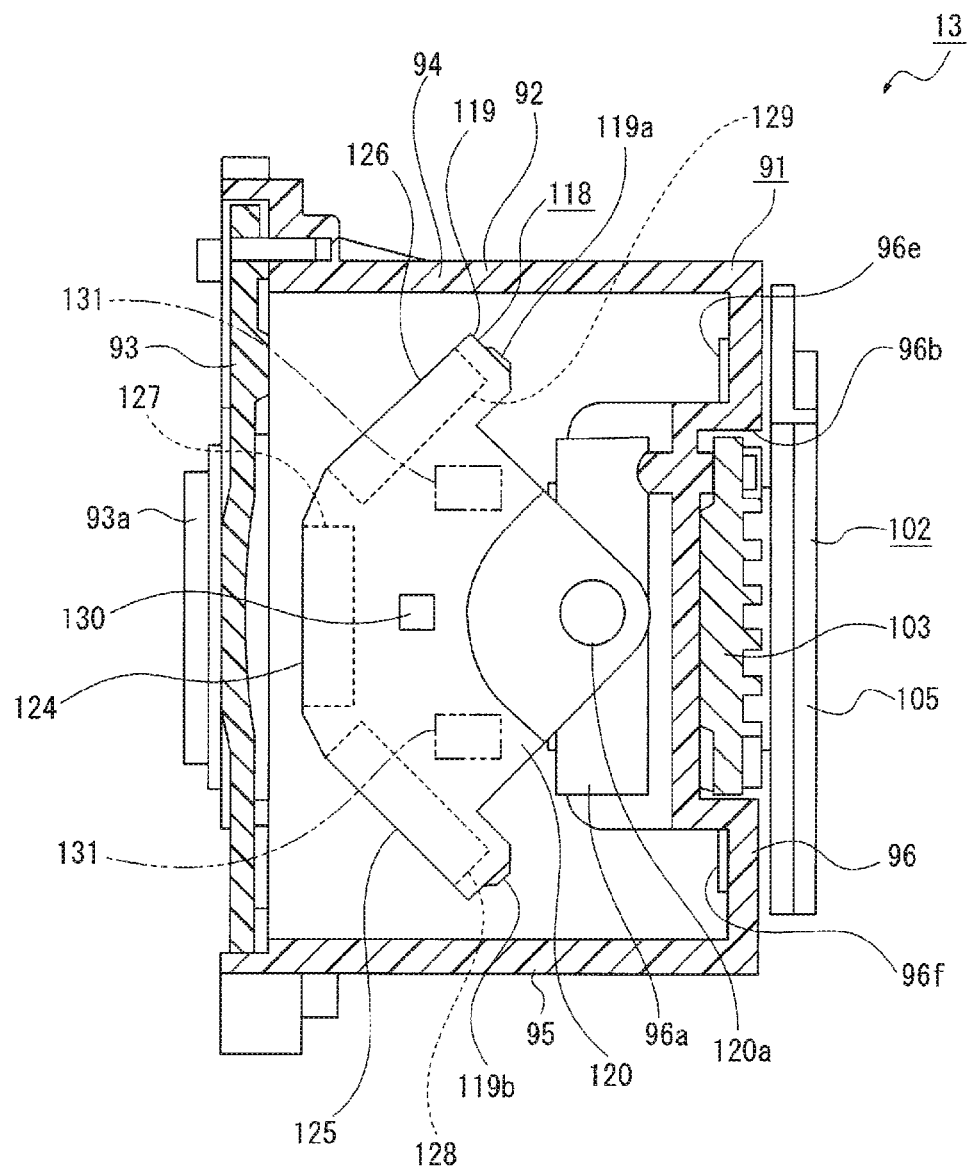
FIG. 52 is a schematic enlarged cross-sectional diagram illustrating an example in which a rotation position of the element holding frame is magnetically detected, along with FIGS. 53 and 54, and a state in which the intermediate position has been detected.
Figure 53:
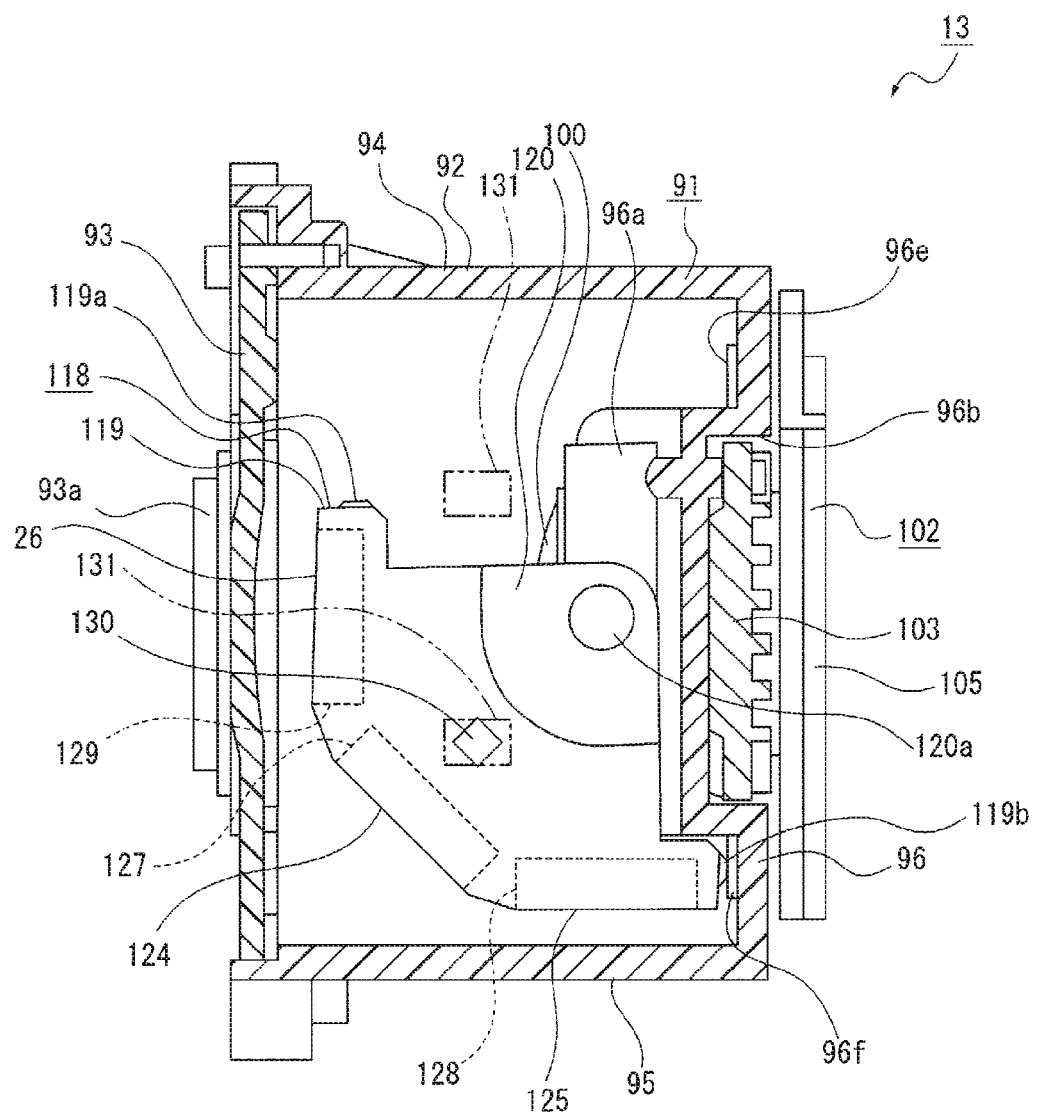
FIG. 53 is a schematic enlarged cross-sectional diagram illustrating a state in which a first rotation position has been detected.
Figure 54:
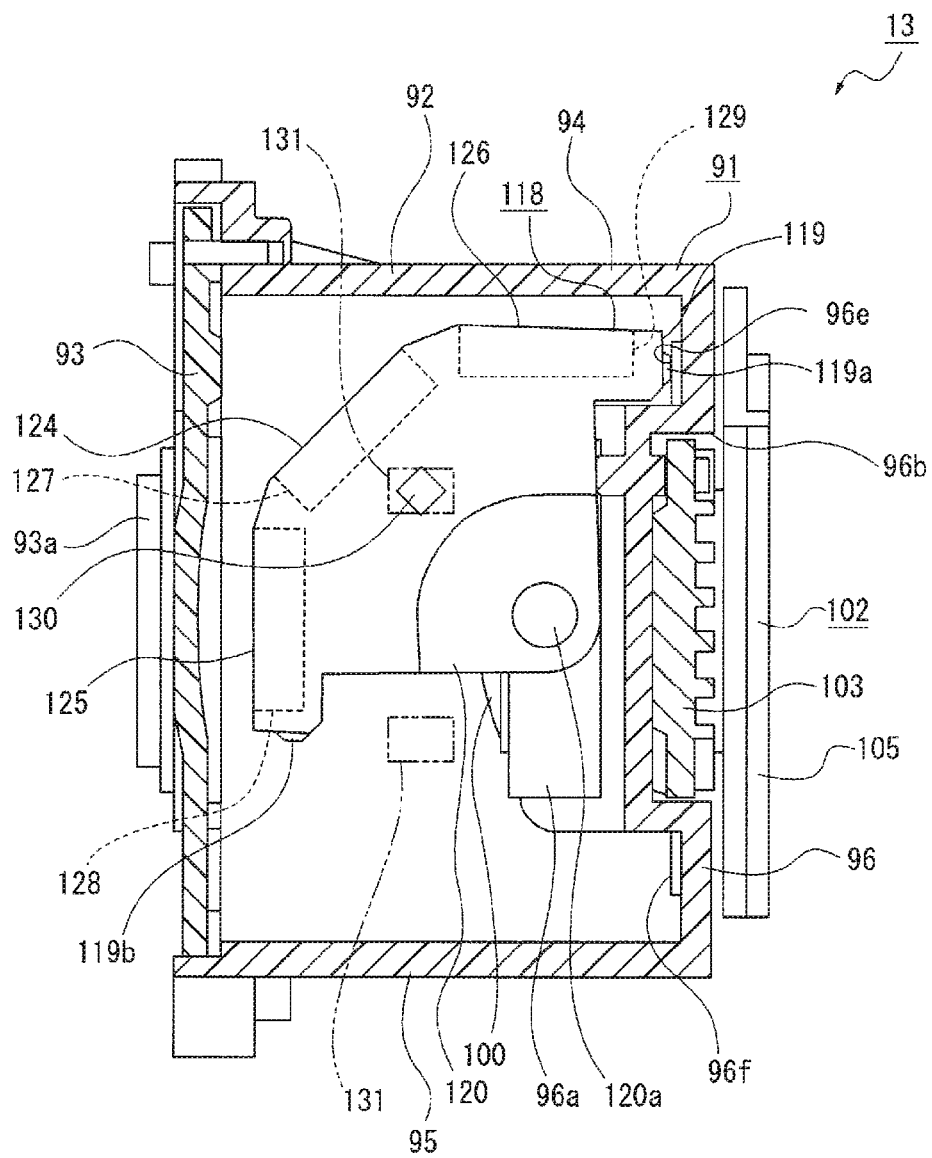
FIG. 54 is a schematic enlarged cross-sectional diagram illustrating a state in which a second rotation position has been detected.

Detecting a rotation position of the element holding frame 118 can be performed using, for example, a detection method using magnetism. As an example of detection using magnetism, for example, there is an example in which a magnet 130 is mounted in the element holding frame 118 and Hall elements 131 and 131 are mounted on, for example, the right side face part 98 of the rear support housing 91, as illustrated in FIGS. 52 to 54. The Hall elements 131 and 131 are mounted at a position at which they face a movement trace of the magnet 130 according to rotation of the element holding frame 118.

Magnetic flux of the magnet 130 does not penetrate the Hall elements 131 and 131 when the magnet 130 is positioned between the Hall elements 131 and 131, and thus it is detected that the element holding frame 118 is at the intermediate position (refer to FIG. 52). Magnetic flux of the magnet 130 penetrates one Hall element 131 when the magnet 130 is positioned to face the one Hall element 131, and thus it is detected that the element holding frame 118 is at the first rotation position (refer to FIG. 53). Magnetic flux of the magnet 130 penetrates the other Hall element 131 when the magnet 130 is positioned to face the other Hall element 131, and thus it is detected that the element holding frame 118 is at the second rotation position (refer to FIG. 54).

By magnetically detecting a rotation position of the element holding frame 118, the rotation position of the element holding frame 118 can be detected without using detection light, there is no need for detection light to be incident on the imaging optical system or the image sensors 105b and 105b, and thus deterioration in quality of captured images or videos can be prevented.

In addition, although the example in which the three optical elements including the first optical element 127, the second optical element 128, and the third optical element 129 are provided has been described above, the number of optical elements is arbitrary as long as it is plural, and the number of optical elements may be two, or four or more.

However, even when four or more optical elements are provided, it is desirable that, when any one of the optical elements is positioned on the optical axis, at least one of the other optical elements be parallel with the optical axis and at least any two of the optical elements be positioned to be orthogonal to each other.

Figure 55:
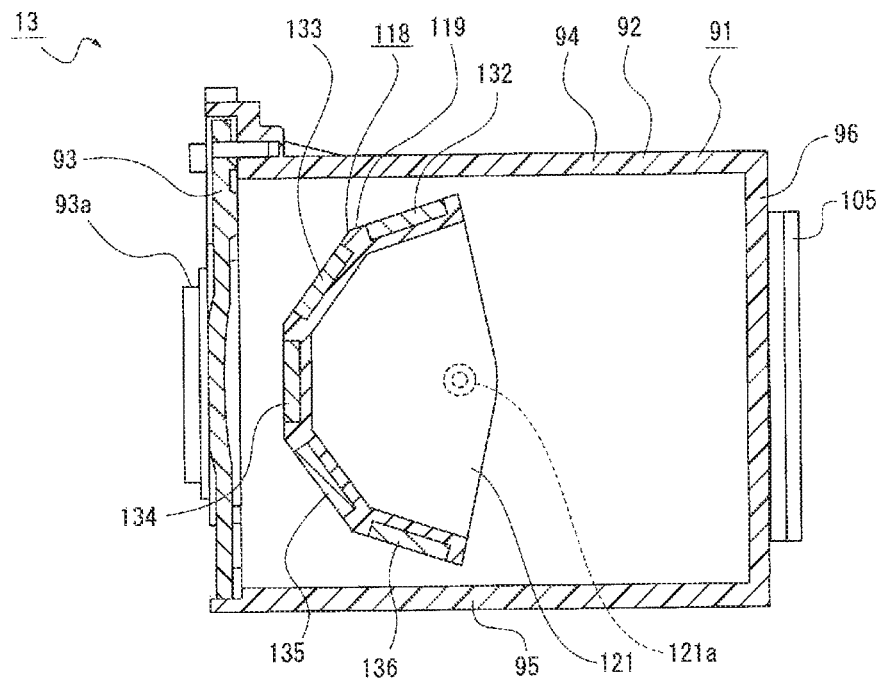
FIG. 55 is a schematic cross-sectional diagram illustrating an example in which five optical elements are held in the element holding frame.

An example in which five optical elements are retained in the element holding frame 118 will be described below (refer to FIGS. 55 and 56).

The five optical elements 132, 133, 134, 135, and 136 are held in the element holding frame 118 to be arranged in order in a rotation direction of the element holding frame 118. The optical elements 132, 133, 134, 135, and 136 are held in the element holding frame 118 in the rotation direction at, for example, equal angles. Each of the optical elements 132, 133, 134, 135, and 136 stops at any of five rotation positions located on the optical axis and held in the element holding frame 118.

Figure 56:
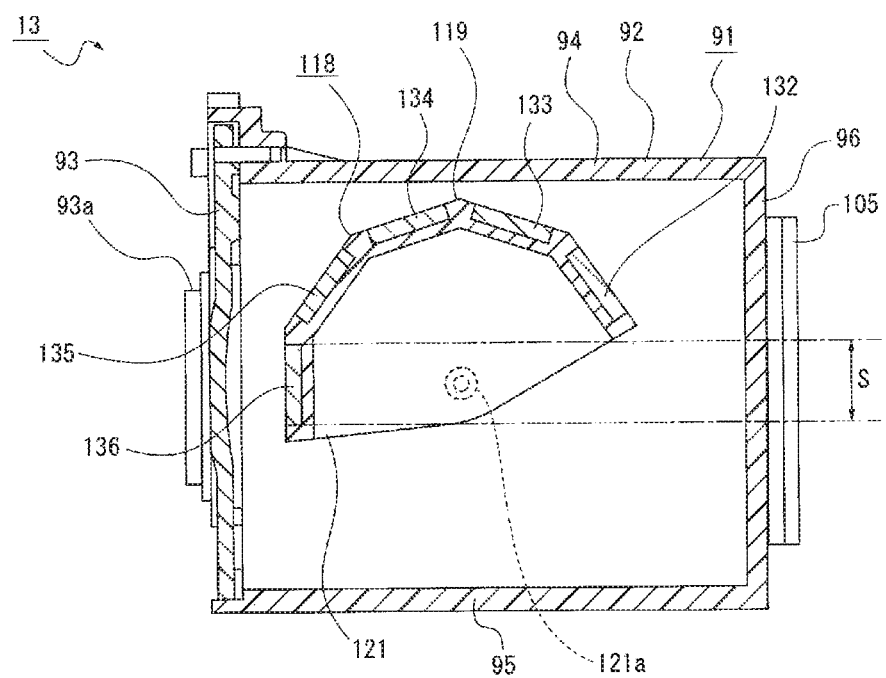
FIG. 56 is a schematic cross-sectional diagram illustrating, in the example in which the five optical elements are held in the element holding frame, a state in which an optical element held at one end of the element holding frame is positioned at an optical axis.

When the optical element 136 held on one end of the element holding frame 118 is positioned on the optical axis in this structure, it is configured such that a path S of light penetrating the optical element 136 is not blocked by the portion of the element holding frame 118 holding the optical element 132 that is held on the other end of the element holding frame 118 (refer to FIG. 56). In addition, when the optical element 132 held on the other end of the element holding frame 118 is positioned on the optical axis, it is also configured such that the path of light penetrating the optical element 132 is not blocked by the portion of the element holding frame 118 holding the optical element 136 held on the one end of the element holding frame 118.

Thus, in the state in which each of the optical elements 132, 133, 134, 135, and 136 is positioned on the optical axis, light passing through each of the optical elements 132, 133, 134, 135, and 136 is not blocked by the element holding frame 118, and thus a satisfactory function of the imaging optical system of the medical observation device 1 can be ensured.

In addition, since the number of optical elements held in the element holding frame 118 is large and functions increase according to the number of held optical elements, functionality of the medical observation device 1 can be improved.

Furthermore, although the example in which the first optical element 127, the second optical element 128, and the third optical element 129 with different functions and types are provided as optical elements has been described above, the technology is not limited to using optical elements with different functions and types, and optical elements with different thicknesses, sizes, and shapes may be used. Particularly, a plurality of neutral density (ND) filters having different light transmittance may be used as optical elements.

Furthermore, although the example in which optical filters are used as optical elements has been described above, the optical elements are not limited to the optical filters, and other optical elements such as a lens, a polarizing element, and a shutter may be used as the optical elements.

In addition, although the example in which the first optical element 127, the second optical element 128, and the third optical element 129 are switched has been descried above, a configuration in which, in the medical observation device 1, optical elements having different functions and types can be switched in left-eye and right-eye imaging optical systems is also possible. For example, the left-eye imaging optical system has an optical element that is an infrared cut-off filter, the right-eye imaging optical system has an optical element that is a special light observation filter that allows only excitation wavelengths of fluorochrome to pass therethrough, and thus different images are captured in the left-eye and right-eye imaging optical systems.

Furthermore, a configuration in which a seal member such as a gasket is disposed between the front part support housing 14 and the intermediate support housing 29 or between the intermediate support housing 29 and the rear support housing 91 to suppress invasion of foreign substances into the inside of the lens barrel 10 is also possible.

Moreover, although the example in which moving objects that are moved through manipulation of the driving motor 56 and the manipulation object 77 are zoom lens groups such as the second zoom lens groups 33 and 33 has been described above, a moving object moved through manipulation of a driving motor or a manipulation object is not limited to a zoom lens group. A moving object moved through manipulation of a driving motor and a manipulation object may have another structure, for example, a focus lens group, an iris mechanism, or the like.

Note that the medical observation device of the present technology can be applied not only to an imaging device that captures images of lesions as described above but also, for example, to a video microscope, or the like.

[Present Technology]

Additionally, the present technology may also be configured as below.

(1)

A medical observation device including:

an imaging optical system configured to capture an image of a subject;

an image sensor configured to photoelectrically convert the image of the subject captured by the imaging optical system; and an element holding frame configured to hold a plurality of optical elements and to be capable of being rotated around a rotation shaft, wherein an axial direction of the rotation shaft is set to a direction orthogonal to an optical axis direction that is a direction of a line from the imaging optical system to the image sensor, and the element holding frame is rotated and thus at least one of the optical elements among the plurality of optical elements is positioned on an optical axis.

(2)

The medical observation device according to (1), wherein, when one of the optical elements is positioned on the optical axis, at least one of the other optical elements is in parallel with the optical axis.

(3)

The medical observation device according to (1) or (2), wherein three or more of the optical elements are provided, and one of the optical elements and at least one of the other optical elements are disposed to be perpendicular to each other.

(4)

The medical observation device according to any of (1) to (3), wherein, the optical elements are optical filters each having different selectivity of wavelengths that pass through.

(5)

The medical observation device according to any of (1) to (4), wherein a position detection sensor configured to detect a rotation position of the element holding frame is provided, and image processing according to the optical element positioned on the optical axis is performed based on a detection result of the position detection sensor.

(6)

The medical observation device according to any of (1) to (5), wherein a support housing in which the element holding frame is supported to be freely rotatable is provided, a stopper-receiving part is provided in the element holding frame, and a stopper part of the support housing is configured to hold the element holding frame at a rotation end in contacting with the stopper-receiving part.

(7)

The medical observation device according to (6), wherein an urging spring configured to press the stopper-receiving part toward the stopper part is provided.

(8)

The medical observation device according to (7), wherein a first stopper part configured to hold the element holding frame at one rotation end and a second stopper part configured to hold the element holding frame at the other rotation end are provided as the stopper part, a first stopper-receiving part brought into contact with the first stopper part and a second stopper-receiving part brought into contact with the second stopper part are provided as the stopper-receiving part, and the urging spring presses the first stopper-receiving part toward the first stopper part at the one rotation end and presses the second stopper-receiving part toward the second stopper part at the other rotation end.

(9)

The medical observation device according to (7) or (8), wherein a manipulation lever configured to be manipulated to cause the element holding frame to rotate is provided, and an urging force of the urging spring is applied to the element holding frame via the manipulation lever.

(10)

The medical observation device according to any of (1) to (9), wherein a support housing in which the element holding frame is supported to be freely rotatable is provided, two fixed lens groups are mounted in the support housing separately from each other in the optical axis direction, and the element holding frame is positioned between the two fixed lens groups.

(11)

The medical observation device according to any of (1) to (10), wherein a support housing formed in a box shape in which the element holding frame is supported to be freely rotatable is provided, and the element holding frame is positioned inside the support housing.

(12)

The medical observation device according to any of (1) to (11), wherein the imaging optical system is provided as a binocular optical system, and the optical elements are positioned across the two optical axes of the binocular optical system.

(13)

The medical observation device according to any of (1) to (12), wherein the imaging optical system is provided as a binocular optical system, and a light shielding wall is provided between two optical axes in the optical holding frame.

(14)
A lens barrel of a medical observation device including:
an imaging optical system configured to capture an image of a subject;
an image sensor configured to photoelectrically convert the image of the subject captured by the imaging optical system; and
an element holding frame configured to hold a plurality of optical elements and to be capable of being rotated around a rotation shaft,
wherein an axial direction of the rotation shaft is set to a direction orthogonal to an optical axis direction that is a direction of a line from the imaging optical system to the image sensor, and
the element holding frame is rotated and thus at least one of the optical elements among the plurality of optical elements is positioned on an optical axis.

REFERENCE SIGNS LIST 1 medical observation device
10 lens barrel
91 rear support housing
96e first stopper part
96f second stopper part
106 manipulation lever
111 urging spring
115 first position detection sensor
116 second position detection sensor
118 element holding frame
119a first stopper-receiving part
119b second stopper-receiving part
123 light shielding wall
127 first optical element
128 second optical element
129 third optical element
132 optical element
133 optical element
134 optical element
135 optical element
136 optical element

The invention claimed is:
1. A medical observation device, comprising:
an imaging optical system configured to capture an image of a subject;
an image sensor configured to photoelectrically convert the image of the subject; and
an element holding frame configured to hold a plurality of optical elements, wherein
the element holding frame is rotatable around a rotation shaft,
an axial direction of the rotation shaft is orthogonal to an optical axis direction,
the optical axis direction is a direction of a line from the imaging optical system to the image sensor,
at least a first optical element of the plurality of optical elements is on an optical axis based on a rotation of the element holding frame around the rotation shaft,
the first optical element is in a first plane and a second optical element of the plurality of optical elements is in a second plane,
the second optical element is in parallel with the optical axis based on the rotation of the element holding frame around the rotation shaft, and
the first plane is perpendicular to the second plane.

2. The medical observation device according to claim 1, wherein the plurality of optical elements includes at least three optical elements.

3. The medical observation device according to claim 1, wherein
the plurality of optical elements includes a plurality of optical filters,
the plurality of optical filters includes at least one of an infrared cut-off filter, a first fluorochrome light observation filter, or a second fluorochrome light observation filter, and
each of the plurality of optical filters has different selectivity of wavelengths.

4. The medical observation device according to claim 1, further comprising a position detection sensor configured to detect a rotation position of the element holding frame, wherein
an image processing process corresponding to the first optical element is executable based on a detection result of the position detection sensor.

5. The medical observation device according to claim 1, further comprising a support housing configured to support the element holding frame, wherein
the element holding frame is freely rotatable,
the element holding frame comprises a stopper-receiving part, and
the support housing comprises a stopper part configured to hold the element holding frame at a rotation end in contact with the stopper-receiving part.

6. The medical observation device according to claim 5, further comprising an urging spring configured to press the stopper-receiving part toward the stopper part.

7. The medical observation device according to claim 6, wherein
the stopper part includes a first stopper part and a second stopper part,
the first stopper part is configured to hold the element holding frame at a first rotation end,
the second stopper part is configured to hold the element holding frame at a second rotation end,
the stopper-receiving part includes a first stopper-receiving part and a second stopper-receiving part,
the first stopper-receiving part is in contact with the first stopper part based on a movement of the first stopper-receiving part,
the second stopper-receiving part is in contact with the second stopper part based on a movement of the second stopper-receiving part, and
the urging spring is further configured to:
press the first stopper-receiving part toward the first stopper part at the first rotation end; and
press the second stopper-receiving part toward the second stopper part at the second rotation end.

8. The medical observation device according to claim 6, further comprising a manipulation lever, wherein
the rotation of the element holding frame is based on manipulation of the manipulation lever, and
an urging force of the urging spring is applicable to the element holding frame via the manipulation lever.

9. The medical observation device according to claim 1, further comprising:
a support housing configured to support the element holding frame,
wherein the element holding frame is freely rotatable; and
two fixed lens groups mounted in the support housing separately from each other in the optical axis direction, wherein the element holding frame is between the two fixed lens groups.

10. The medical observation device according to claim 1, further comprising a support housing in a box shape, wherein
   the support housing is configured to support the element holding frame,
   the element holding frame is freely rotatable, and
   the element holding frame is inside the support housing.

11. The medical observation device according to claim 1, wherein
   the imaging optical system is a binocular optical system, and
   the plurality of optical elements is across two optical axes of the binocular optical system.

12. The medical observation device according to claim 1, wherein
   the imaging optical system is a binocular optical system, and
   the element holding frame comprises a light shielding wall between two optical axes in the element holding frame.

13. A lens barrel of a medical observation device, the lens barrel comprising:
   an imaging optical system configured to capture an image of a subject;
   an image sensor configured to photoelectrically convert the image of the subject; and
   an element holding frame configured to hold a plurality of optical elements, wherein
      the element holding frame is rotatable around a rotation shaft,
      an axial direction of the rotation shaft is orthogonal to an optical axis direction,
      the optical axis direction is a direction of a line from the imaging optical system to the image sensor,
      at least a first optical element of the plurality of optical elements is on an optical axis based on a rotation of the element holding frame around the rotation shaft,
      the first optical element is in a first plane and a second optical element of the plurality of optical elements is in a second plane,
      the second optical element is in parallel with the optical axis based on the rotation of the element holding frame around the rotation shaft, and
      the first plane is perpendicular to the second plane.

* * * * *